US011634444B2

(12) United States Patent
Pan et al.

(10) Patent No.: US 11,634,444 B2
(45) Date of Patent: Apr. 25, 2023

(54) METAL ORGANIC COMPLEX, HIGH POLYMER, COMPOSITION, AND ORGANIC ELECTRONIC COMPONENT

(71) Applicant: GUANGZHOU CHINARAY OPTOELECTRONIC MATERIALS LTD., Guangdong (CN)

(72) Inventors: Junyou Pan, Guangdong (CN); Chao Shi, Guangdong (CN)

(73) Assignee: GUANGZHOU CHINARAY OPTOELECTRONIC MATERIALS LTD., Guangdong (CN)

( * ) Notice: Subject to any disclaimer, the term of this patent is extended or adjusted under 35 U.S.C. 154(b) by 909 days.

(21) Appl. No.: 16/463,500

(22) PCT Filed: Nov. 23, 2017

(86) PCT No.: PCT/CN2017/112700
§ 371 (c)(1),
(2) Date: May 23, 2019

(87) PCT Pub. No.: WO2018/095379
PCT Pub. Date: May 31, 2018

(65) Prior Publication Data
US 2019/0367544 A1   Dec. 5, 2019

(30) Foreign Application Priority Data

Nov. 23, 2016 (CN) .......................... 201611047053.4

(51) Int. Cl.
| | | |
|---|---|---|
| *H01L 51/50* | (2006.01) | |
| *C07F 15/00* | (2006.01) | |
| *C07D 401/04* | (2006.01) | |
| *C07D 409/04* | (2006.01) | |
| *C07F 1/08* | (2006.01) | |
| *H01L 51/00* | (2006.01) | |

(52) U.S. Cl.
CPC ........ *C07F 15/0033* (2013.01); *C07D 401/04* (2013.01); *C07D 409/04* (2013.01); *C07F 1/08* (2013.01); *H01L 51/0007* (2013.01); *H01L 51/0067* (2013.01); *H01L 51/0068* (2013.01); *H01L 51/0085* (2013.01); *H01L 51/0091* (2013.01); *H01L 51/5016* (2013.01); *H01L 51/5056* (2013.01); *H01L 51/5092* (2013.01)

(58) Field of Classification Search
None
See application file for complete search history.

(56) References Cited

U.S. PATENT DOCUMENTS

| | | |
|---|---|---|
| 4,769,292 A | 9/1988 | Tang et al. |
| 5,121,029 A | 6/1992 | Hosokawa et al. |
| 5,130,603 A | 7/1992 | Tokailin et al. |
| 6,020,078 A | 2/2000 | Chen et al. |
| 6,251,531 B1 | 6/2001 | Enokida et al. |
| 6,824,895 B1 | 11/2004 | Sowinski et al. |
| 6,830,828 B2 | 12/2004 | Thompson et al. |
| 6,835,469 B2 | 12/2004 | Kwong et al. |
| 7,029,766 B2 | 4/2006 | Huo et al. |
| 7,250,532 B2 | 7/2007 | Iwakuma et al. |
| 2001/0053462 A1 | 12/2001 | Mishima |
| 2002/0131984 A1 | 9/2002 | Blake et al. |

(Continued)

FOREIGN PATENT DOCUMENTS

| | | |
|---|---|---|
| CN | 1583691 A | 2/2005 |
| CN | 101035877 | 9/2007 |

(Continued)

OTHER PUBLICATIONS

Yeh et.al., Synthesis and electroluminescent property of bis{2-(naphtha[3,4]imidazol-2-yl)quinolinato} zinc; Materials Letters 59 (2005) 2911-2914 (Year: 2005).*
PCT/CN2017/112700, "International Search Report", dated Feb. 22, 2018, 3 pages.
Endo et al., "Thermally Activated Delayed Fluorescence from $Sn^{4+}$-Porphyrin Complexes and Their Application to Organic Light-Emitting Diodes—A Novel Mechanism for Electroluminescence", Adv Mater, vol. 21, 2009, pp. 4802-4806.
Li et al., Highly Efficient Organic Light-Emitting Diode Based on a Hidden Thermally Activated Delayed Fluorescence Channel in a Heptazine Derivative, Adv Mater, vol. 25, 2013, pp. 1-5.

(Continued)

*Primary Examiner* — Gregory D Clark
(74) *Attorney, Agent, or Firm* — PV IP PC; Wei Te Chung; Ude Lu

(57) ABSTRACT

An metal organic complex has the following general formula (I):

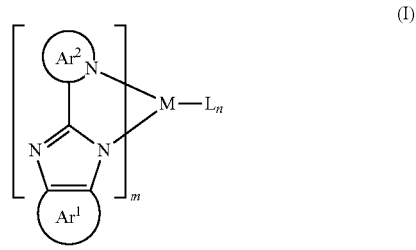

(I)

$Ar^1$, selected from at least one of aromatic hydrocarbyl, $R^1$-substituted aromatic hydrocarbyl, heterocyclic aromatic hydrocarbyl and $R^1$-substituted heterocyclic aromatic hydrocarbyl; and $Ar^2$, selected from one of heterocyclic aromatic hydrocarbyl containing N atoms and $R^1$-substituted heterocyclic aromatic hydrocarbyl containing N atoms; M being a transitional group metal element; L being selected from one of a monodentate neutral ligand, a monodentate anionic ligand, a bidentate neutral ligand and a bidentate anionic ligand; m being any integer ranging from 1 to 3; and n being any integer ranging from 1 to 2.

16 Claims, No Drawings

(56) References Cited

U.S. PATENT DOCUMENTS

| | | | |
|---|---|---|---|
| 2002/0134984 | A1 | 9/2002 | Igarashi |
| 2004/0091738 | A1* | 5/2004 | Psai ............... H01L 51/0085 |
| | | | 252/301.16 |
| 2005/0258742 | A1 | 11/2005 | Tsai et al. |
| 2006/0210830 | A1 | 9/2006 | Funahashi et al. |
| 2006/0222886 | A1 | 10/2006 | Kwong et al. |
| 2007/0087219 | A1 | 4/2007 | Ren et al. |
| 2007/0092753 | A1 | 4/2007 | Begley et al. |
| 2007/0252517 | A1 | 11/2007 | Owczarczyk et al. |
| 2008/0027220 | A1 | 1/2008 | Stossel et al. |
| 2008/0048254 | A1 | 2/2008 | Saka |
| 2008/0113101 | A1 | 5/2008 | Inoue et al. |
| 2008/0248329 | A1* | 10/2008 | Igarashi ............ H05B 33/14 |
| | | | 428/704 |
| 2009/0061681 | A1 | 3/2009 | McMunigal et al. |
| 2009/0134784 | A1 | 5/2009 | Lin et al. |
| 2009/0236974 | A1* | 9/2009 | Tamaru ............ H05B 33/20 |
| | | | 313/504 |
| 2012/0004407 | A1 | 1/2012 | Stoessel et al. |
| 2012/0217869 | A1 | 8/2012 | Adachi et al. |

FOREIGN PATENT DOCUMENTS

| | | |
|---|---|---|
| CN | 102282150 A | 12/2011 |
| CN | 103483332 A | 1/2014 |
| DE | 102005058557 A1 | 6/2007 |
| EP | 1191613 B1 | 3/2006 |
| EP | 1957606 A1 | 8/2008 |
| EP | 1191614 B1 | 5/2009 |
| EP | 1191612 B1 | 9/2009 |
| JP | 2913116 B2 | 6/1999 |
| JP | 2005255890 A | 9/2005 |
| JP | 2008053397 A | 3/2008 |
| KR | 20090077332 A | 7/2009 |
| TW | 201309696 A | 3/2013 |
| TW | 201309778 A | 3/2013 |
| TW | 201343874 A | 11/2013 |
| TW | 201350558 A | 12/2013 |
| WO | 200070655 A2 | 11/2000 |
| WO | 2001021729 A1 | 3/2001 |
| WO | 200141512 A1 | 6/2001 |
| WO | 200202714 A2 | 1/2002 |
| WO | 200215645 A1 | 2/2002 |
| WO | 2005019373 A2 | 3/2005 |
| WO | 2005033244 A1 | 4/2005 |
| WO | 2006/000388 A1 | 1/2006 |
| WO | 2006/000389 A1 | 1/2006 |
| WO | 2006/058737 A1 | 6/2006 |
| WO | 2006087521 | 8/2006 |
| WO | 2006/122630 A1 | 11/2006 |
| WO | 2007/065549 A1 | 6/2007 |
| WO | 2007095118 A2 | 8/2007 |
| WO | 2007/115610 A1 | 10/2007 |
| WO | 2007/140847 A1 | 12/2007 |
| WO | 2008/006449 A1 | 1/2008 |
| WO | 2009118087 A1 | 10/2009 |
| WO | 2009146770 A2 | 12/2009 |
| WO | 2010015307 A1 | 2/2010 |
| WO | 2010031485 A1 | 3/2010 |
| WO | 2010054728 A1 | 5/2010 |
| WO | 2010054731 A1 | 5/2010 |
| WO | 2010086089 A1 | 8/2010 |
| WO | 2010099852 A1 | 9/2010 |
| WO | 2010102709 A1 | 9/2010 |
| WO | 2010135519 A1 | 11/2010 |
| WO | 2011110277 A1 | 9/2011 |
| WO | 2011141110 A2 | 11/2011 |
| WO | 2011157339 A1 | 12/2011 |
| WO | 2012007086 A1 | 1/2012 |
| WO | 2012007087 A1 | 1/2012 |
| WO | 2012007088 A1 | 1/2012 |
| WO | 2013133359 A1 | 9/2013 |
| WO | 2013154064 A1 | 10/2013 |

OTHER PUBLICATIONS

Dias et al., "Triplet Harvesting with 100% Efficiency by Way of Thermally Activated Delayed Fluorescence in Charge Transfer OLEO Emitters", Adv Mater, vol. 25, 2013, pp. 3707-3714.

Mehes et al., "Enhanced Electroluminescence Efficiency in a Spiro-Acridine Derivative through Thermally Activated Delayed Fluorescence", Angew Chem Int Ed, vol. 51, 2012, pp. 11311-11315.

Endo et al, "Efficient up-conversion of triplet excitons into a singlet state and its application for organic light emitting diodes", Appl Phys Lett, vol. 98, 2011, pp. 083302-1-083302-3.

Lee et al, "High-efficiency organic light-emitting diodes utilizing thermally activated delayed fluorescence from triazinebased donor-acceptor hybrid molecules", Appl Phys Lett, vol. 101, 2012, pp. 093306-1-093306-4.

Nakagawa et al, "Electroluminescence based on thermally activated delayed fluorescence generated by a spirobifluorene donor-acceptor structure" Chem Commun, vol. 48, 2012, pp. 9580-9582.

Tanaka et al, "Efficient green thermally activated delayed fluorescence (TADF) from a phenoxazine-triphenyltriazine (PXZ-TRZ) derivative", Chem Commun, vol. 48, 2012, pp. 11392-11394.

Nasu et al, "A highly luminescent spiro-anthracenone-based organic light-emitting diode exhibiting thermally activated delayed fluorescence", Chem Commun, vol. 49, 2013, pp. 1-3.

Komino et al, "Suppression of Efficiency Roll-Off Characteristics in Thermally Activated Delayed Fluorescence Based Organic Light-Emitting Diodes Using Randomly Oriented Host Molecules", Chem Mater, vol. 25, 2013, pp. 3038-3047.

Tanaka et al, "Twisted Intramolecular Charge Transfer State for Long-Wavelength Thermally Activated Delayed Fluorescence", Chem Mater, vol. 25, 2013, pp. 3766-3771.

Zhang et al, "Design of Efficient Thermally Activated Delayed Fluorescence Materials for Pure Blue Organic Light Emitting Diodes", J Am Chem Soc, vol. 134, 2012, pp. 14706-14709.

Lee et al, "Oxadiazole- and triazole-based highly-efficient thermally activated delayed fluorescence emitters for organic light-emitting diodes", J Mater Chem C, vol. 1, 2013, pp. 1-6.

Ishimatsu, "Solvent Effect on Thermally Activated Delayed Fluorescence by 1,2,3,5-Tetrakis(carbazol-9-yl)-4,6-dicyanobenzene", J Phys Chem A, vol. 117, 2013, pp. 5607-5612.

Goushi et al., "Organic light-emitting diodes employing efficient reverse intersystem crossing for triplet-to-singlet state conversion", Nature Photonics, vol. 6, Apr. 2012, pp. 253-258.

Uoyama et al., "Highly efficient organic light-emitting diodes from delayed fluorescence", Nature, vol. 492, Dec. 2012, 234-238.

Adachi et al., "High-efficiency red electrophosphorescence devices", Appl Phys Lett vol. 78 (2001), pp. 1622-1624.

Baldo et al "High-efficiency fluorescent organic light-emitting devices using a phosphorescent sensitizer", Nature, vol. 403, (2000), pp. 750-753.

Kido et al., "Bright red lightemitting organic electroluminescent devices having a europium complex as an emitter", Appl Phys Lett, vol. 65, 1994, pp. 2124-2126.

Johnson et al., "Luminescent Iridium(I), Rhodium(I), and Platinum(II) Dithiolate Complexes", JAGS, vol. 105, 1983, pp. 1795-1802.

Kido et al., "Electroluminescence in a Terbium Complex", Chem Lett (1990), pp. 657-660.

Ma et al, "Electroluminescence from triplet metal-ligand charge-transfer excited state of transition metal complexes" Synth Metals, vol. 94, 1998, pp. 245-248.

Wrighton et al, "The Nature of the Lowest Excited State in Tricarbonylchloro-1,10-phenanthrolinerhenium(I) and Related Complexes", JAGS vol. 96, 1974, pp. 998-1003.

Kipphan (Handbook of Print Media: Technologies and Production Methods), ISBN 3-540-67326-1, Chapter 1.3, pp. 40-67, Chapter 1.5, pp. 117-144, Chapter 5.5, pp. 711-730.

Newkome, et al., Dendrimers and Dendrons, Wiley-VCH Verlag GmbH & Co. KGaA, (2002) pp. 1-21, 51-76, 76-102, 102-118, 191-234, 234-282, 282-309, 331-365, 366-393, 395-431, 431-455.

Bulovic et.al. "Transparent light-emitting devices" Nature, vol. 380, (1996) p. 29.

(56) References Cited

OTHER PUBLICATIONS

Gu et al., "Transparent organic light emitting devices" Appl. Phys. Lett.1996, vol. No. 19, 68, pp. 2606-2608.

First Office Action issued for Chinese Patent Application No. 201780059736.8, dated Jan. 8, 2021, 18 pages.

Liang et al., "Application of heteroleptic iridium complexes with fluorenyl-modified 1-phenylisoquinoline ligand for high-efficiency red polymer light-emitting devices", Journal of Organometallic Chemistry, vol. 694, (2009), pp. 3172-3178.

Gong et al., Cyclometalated Ir(III) complexes containing quinoline-benzimidazole-based NAN ancillary ligands: structural and luminescence modulation by varying substituent group or protonation/deprotonation state of imidazole unit, Dalton Transactions, The Royal Society of Chemistry, vol. 46, (2016), pp. 1-12.

Yeh, "Synthesis and electroluminescent property of bis (2-(benzimidazol-2-yl) quinolinato) zinc", Materials Letters, vol. 59, (2005), pp. 1811-1814.

Yue, et al. "Synthesis and Photoelectrical Properties of Room-Temperature Phosphorescent (ppy)2Ir(pybi) Complex" Acta Physico-Chimica Sinica, vol. 28, (2012), pp. 1593-1598.

* cited by examiner

METAL ORGANIC COMPLEX, HIGH POLYMER, COMPOSITION, AND ORGANIC ELECTRONIC COMPONENT

CROSS-REFERENCE TO RELATED APPLICATIONS

The present application is the national phase of International Application PCT/CN2017/112700, filed on Nov. 23, 2017, which claims priority to Chinese Application No. 201611047053.4, filed on Nov. 23, 2016, both of which are incorporated herein by reference in their entireties.

TECHNICAL FIELD

The present disclosure relates to the field of organic electronic devices, and more particularly to a metal organic complex, a polymer, a formulation and an organic electronic device.

BACKGROUND

Organic light-emitting diodes (OLEDs) show great potentials in the applications of optoelectronic devices (such as flat-panel displays and lighting) due to the synthetic diversities, relatively low manufacturing costs, and excellent optical and electrical properties of organic semiconductive materials.

In order to improve the emitting efficiency of the organic light-emitting diodes, various light-emitting materials based on fluorescent and phosphorescent materials have been developed. The organic light-emitting diodes based on fluorescent materials have high reliability, but their internal electroluminescence quantum efficiency is limited to 25% under electric field excitation, since the probability ratio of the exciton generating a singlet excited state to a triplet excited state is 1:3. In 1999, Professor Thomson of the University of Southern California and Professor Forrest of Princeton University successfully prepared green electrophosphorescence devices by incorporating tris (2-phenylpyridine) iridium (Ir (ppy)$_3$) into N, N-dicarbazole biphenyl (CBP), which aroused great interests in complex phosphorescent materials. The introduction of heavy metals improves the molecular spin orbit coupling, shortens the phosphorescence lifetime and enhances the intersystem crossing of molecules, so that phosphorescence can be successfully emitted. Moreover, since the reactions of this kind of complexes are mild, it is easy to alter the structure and the substituent groups of the complexes, to adjust the emission wavelength, to obtain electrophosphorescent materials with excellent properties. So far, the internal quantum efficiency of the phosphorescent OLED is close to 100%. However, most of phosphorescent materials concentrate on iridium and platinum complexes, and the types of complexes are simple.

SUMMARY

Based on the above, a novel metal organic complex is provided.

In addition, a polymer, a formulation and an organic electronic device are also provided.

A metal organic complex having the following general formula is provided:

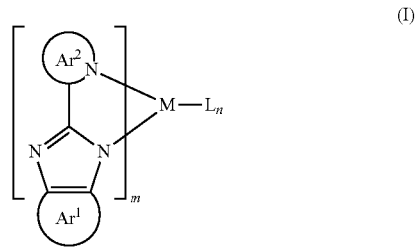

wherein, $Ar^1$ is selected from one of the group consisting of aromatic hydrocarbyl, $R^1$-substituted aromatic hydrocarbyl, heteroaromatic cyclic hydrocarbyl and $R^1$-substituted heteroaromatic cyclic hydrocarbyl;

$Ar^2$ is selected from one of the group consisting of heteroaromatic cyclic hydrocarbyl containing N atoms and $R^1$-substituted heteroaromatic cyclic hydrocarbyl containing N atoms;

$R^1$ is selected from one of the group consisting of H, F, Cl, Br, I, D, CN, $NO_2$, $CF_3$, $B(OR^2)_2$, $Si(R^2)_3$, linear alkyl, $R^2$-substituted linear alkyl, alkyl ether group, $R^2$-substituted alkyl ether group, alkyl thioether group, $R^2$-substituted alkyl thioether group, branched alkyl, $R^2$-substituted branched alkyl, cyclic alkyl, and $R^2$-substituted cyclic alkyl; $R^2$ is selected from one of the group consisting of H, D, aliphatic alkyl, aromatic group, aromatic cyclic group and heteroaromatic group;

M is a transitional metal element;

L is selected from one of the group consisting of a monodentate neutral ligand, a monodentate anionic ligand, a bidentate neutral ligand and a bidentate anionic ligand;

m is any integer from 1 to 3;

n is any integer from 0 to 2;

A polymer comprising a repeating unit comprising the above metal organic complex is also provided.

A formulation comprising one of the above metal organic complex and the above polymer is further provided.

An organic electronic device comprising one of the above metal organic complex, the above polymer, and the above formulation is further provided.

The details of one or more embodiments of the present disclosure are set forth in the accompanying drawings and the description below. Other features, objects and advantages of the present disclosure will become apparent from the description, the accompanying drawings, and the claims.

DETAILED DESCRIPTION OF THE EMBODIMENTS

The present disclosure provides a metal organic complex, a polymer, a formulation and an organic electronic device. In order to make the purpose, technical solution and effects of the present disclosure clearer and more specific, the present disclosure will be further described in detail below. It should be noted that, the specific embodiments illustrated herein are merely for the purpose of explanation, and should not be deemed to limit the disclosure.

A metal organic complex according to one embodiment has the following general formula:

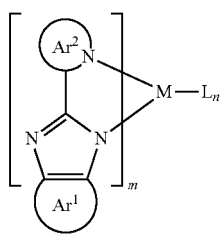

(I)

wherein, $Ar^1$ is selected from one of the group consisting of aromatic hydrocarbyl, $R^1$-substituted aromatic hydrocarbyl, heteroaromatic cyclic hydrocarbyl, $R^1$-substituted heteroaromatic cyclic hydrocarbyl, non-aromatic cyclic group, and $R^1$-substituted non-aromatic cyclic group. Wherein, $Ar^1$ contains 5 to 22 C atoms, further 5 to 18 C atoms, and still further 5 to 12 C atoms. Wherein, C atoms refer to carbon atoms (the same below).

$Ar^2$ is selected from one of heteroaromatic cyclic hydrocarbyl containing N atoms and $R^1$-substituted heteroaromatic cyclic hydrocarbyl containing N atoms. Wherein, $Ar^2$ contains 5 to 22 C atoms, further, $Ar^2$ contains 5 to 20 C atoms, still further, $Ar^2$ contains 5 to 18 C atoms, and even further, $Ar^2$ contains 5 to 12 C atoms.

$R^1$ is selected from one of the group consisting of H, F, Cl, Br, I, D, CN, $NO_2$, $CF_3$, $B(OR^2)_2$, $Si(R^2)_3$, linear alkyl, $R^2$-substituted linear alkyl, alkyl ether group, $R^2$-substituted alkyl ether group, alkyl thioether group, $R^2$-substituted alkyl thioether group, branched alkyl, $R^2$-substituted branched alkyl, cyclic alkyl, and $R^2$-substituted cyclic alkyl.

In one embodiment, one or more non-adjacent methylene groups in the linear alkyl, $R^2$-substituted linear alkyl, cyclic alkyl and $R^2$-substituted cyclic alkyl are substituted by at least one of $R^2C=CR^2$, $C≡C$, $Si(R^2)_2$, $Ge(R^2)_2$, $Sn(R^2)_2$, $C=O$, $C=S$, $C=Se$, $C=N(R^2)$, O, S, —COO— and $CONR^2$.

Specifically, H atoms in $B(OR^2)_2$, $Si(R^2)_3$, linear alkyl, $R^2$-substituted linear alkyl, alkyl ether group, $R^2$-substituted alkyl ether group, alkyl thioether group, $R^2$-substituted alkyl thioether group, branched alkyl, $R^2$-substituted branched alkyl, cyclic alkyl, and $R^2$-substituted cyclic alkyl are substituted by one of D, F, Cl, Br, I, CN, $NO_2$, $R^2$, aromatic amino substituted by aromatic group or heteraromatic cyclic group, carbazolyl and $R^1$-substituted carbazolyl.

$R^2$ and $R^3$ are each selected from one of the group consisting of H, D, aliphatic alkyl, aromatic group, aromatic cyclic group and heteroaromatic group. Wherein, the heteroaromatic group includes substituted and unsubstituted heteroaromatic groups.

M is a transitional metal element.

L is selected from one of the group consisting of a monodentate neutral ligand, a monodentate anionic ligand, a bidentate neutral ligand and a bidentate anionic ligand.

m is any integer from 1 to 3.

n is any integer from 0 to 2.

The aromatic group refers to a hydrocarbyl comprising at least one aromatic ring, including monocyclic group and polycyclic ring system. The heteroaromatic group refers to a hydrocarbyl comprising at least one heteroaromatic ring (containing heteroatoms), including monocyclic group and polycyclic ring system. Such polycyclic rings may have two or more rings, wherein two carbon atoms are shared by two adjacent rings, i.e., fused ring. At least one of such polycyclic rings is aromatic or heteroaromatic. Wherein, aromatic or heteroaromatic groups in the aromatic or heteroaromatic cyclic groups may be interrupted by short non-aromatic units. Wherein, the non-aromatic units are less than 10% of non-H atoms (hydrogen atoms), and further, the non-aromatic units are less than 5% of non-H atoms (hydrogen atoms). For example, the non-aromatic units are C (carbon), N (nitrogen), or O (oxygen) atoms. Therefore, ring systems such as 9,9'-spirobifluorene, 9,9-diarylfluorene, triarylamine, diaryl ether and the like are also considered to be aromatic ring systems.

Specifically, the aromatic group is selected from one of the group consisting of benzene, derivatives of benzene, naphthalene, derivatives of naphthalene, anthracene, derivatives of anthracene, phenanthrene, derivatives of phenanthrene, perylene, derivatives of perylene, tetracene, derivatives of tetracene, pyrene, derivatives of pyrene, benzopyrene, derivatives of benzopyrene, triphenylene, derivatives of triphenylene, acenaphthene, derivatives of acenaphthene, fluorene, and derivatives of fluorene.

Specifically, the heteroaromatic group is selected from one of the group consisting of furan, derivatives of furan, benzofuran, derivatives of benzofuran, thiophene, derivatives of thiophene, benzothiophene, derivatives of benzothiophene, pyrrole, derivatives of pyrrole, pyrazole, derivatives of pyrazole, triazole, derivatives of triazole, imidazole, derivatives of imidazole, oxazole, derivatives of oxazole, oxadiazole, derivatives of oxadiazole, thiazole, derivatives of thiazole, tetrazole, derivatives of tetrazole, indole, derivatives of indole, carbazole, derivatives of carbazole, pyrroloimidazole, derivatives of pyrroloimidazole, pyrrolopyrrole, derivatives of pyrrolopyrrole, thienopyrrole, derivatives of thienopyrrole, thienothiophene, derivatives of thienothiophene, furopyrrole, derivatives of furopyrrole, furofuran, derivatives of furofuran, thienofuran, derivatives of thienofuran, benzisoxazole, derivatives of benzisoxazole, benzisothiazole, derivatives of benzisothiazole, benzimidazole, derivatives of benzimidazole, pyridine, derivatives of pyridine, pyrazine, derivatives of pyrazine, pyridazine, derivatives of pyridazine, pyrimidine, derivatives of pyrimidine, triazine, derivatives of triazine, quinoline, derivatives of quinoline, isoquinoline, derivatives of isoquinoline, cinnoline, derivatives of cinnoline, quinoxaline, derivatives of quinoxaline, phenanthridine, derivatives of phenanthridine, perimidine, derivatives of perimidine, quinazoline, derivatives of quinazoline, quinazolinone and derivatives of quinazolinone.

In one embodiment, $Ar^1$ is selected from one of non-aromatic cyclic group containing 2 to 20 carbon atoms and R-substituted non-aromatic cyclic group containing 2 to 20 carbon atoms, so that the triplet energy level of the metal organic complex can be increased, thereby it is easy to obtain green or blue light emitters.

In some embodiment, the ring of the non-aromatic cyclic group contains 1 to 10 carbon atoms, and further, the ring of the non-aromatic cyclic group contains 1 to 6 carbon atoms. The non-aromatic cyclic group includes saturated and unsaturated ring systems, and further, the ring system of the non-aromatic cyclic group is substituted by group R.

R includes at least one heteroatom selected from Si, N, P, O, S and Ge, further, R includes at least one heteroatom selected from Si, N, P, O and S. Wherein, R is selected from one of cyclohexyl-like group, piperidinyl-like group, and cyclooctadienyl-like cyclic group.

In another embodiment, R may also be selected from one of the group consisting of $C_1$ to $C_{10}$ alkyl, $C_1$ to $C_{10}$ alkoxy, $C_2$ to $C_{10}$ aryl, and $C_2$ to $C_{10}$ heteroaryl.

Wherein, $C_1$ to $C_{10}$ alkyl is selected from one of the group consisting of methyl, ethyl, n-propyl, isopropyl, cyclopropyl, n-butyl, isobutyl, sec-butyl, tert-butyl, cyclobutyl, 2-methylbutyl, n-pentyl, n-hexyl, cyclohexyl, n-heptyl, cycloheptyl, n-octyl, cyclooctyl, 2-ethylhexyl, trifluoromethyl, pentafluoromethyl, 2,2,2-trifluoroethyl, vinyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl and octynyl.

Wherein, $C_1$ to $C_{10}$ alkoxy is selected from one of the group consisting of methoxy, ethoxy, n-propoxy, isopropoxy, n-butoxy, isobutoxy, sec-butoxy tert-butoxy and 2-methyl butoxy.

Wherein, $C_2$ to $C_{10}$ aryl or heteroaryl may be selected to be monovalent or divalent depending on whether the metal organic complex is used as a red emitter or a green emitter.

Specifically, $C_2$ to $C_{10}$ aryl or heteroaryl is selected from one of the group consisting of benzene, naphthalene, anthracene, pyrene, dihydropyrene, chrysene, pyrenyl, fluoranthene, naphthacene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthalimidazole, phenamidazole, pyridinimidazole, pyrazinoimidazole, quinoxalinimidazole, oxazole, benzoxazole, naphthoxazole, anthraoxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, 1,5-naphthyridine, N-carbazole, benzoporphyrin, phenanthroline, 1,2,3-triazole, 1,2,4-triazole, benzotriazole, 1,2,3-oxadiazole, 1,2, 4-oxadiazole, 1,2,5-oxadiazole, 1,3,4-oxadiazole, 1,2,3-thiadiazole, 1,2,4-thiadiazole, 1,2, 5-thiadiazole, 1,3,4-thiadiazole, 1,3, 5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole In other embodiments, the aromatic cyclic group and the heteroaromatic cyclic group may further be selected from one of the group consisting of biphenylene, terphenyl, fluorene, spirobifluorene, dihydrophenanthrene, tetrahydropyrene, and cis and trans indenofluorenes.

Wherein $Ar^1$ is selected from one of the following general formulas:

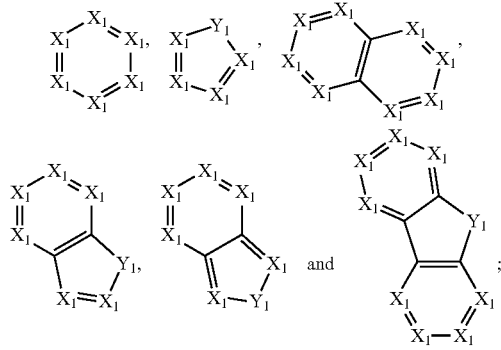

wherein, a plurality of $X_1$ are each independently selected from $CR^4$ or N;

$Y_1$ is selected from $CR^4R^5$, $SiR^4R^5$, $NR^4$, $C(=O)$, S or O;

$R^4$ and $R^5$ are each independently selected from at least one of the group consisting of H, D, linear alkyl containing 1 to 20 C atoms, alkoxy containing 1 to 20 C atoms, thioalkoxy containing 1 to 20 C atoms, branched alkyl containing 3 to 20 C atoms, cyclic alkyl containing 3 to 20 C atoms, silyl containing 3 to 20 C atoms, substituted keto containing 1 to 20 C atoms, alkoxycarbonyl containing 2 to 20 C atoms, aryloxycarbonyl containing 7 to 20 C atoms, cyano, carbamoyl, halocarbonyl, formyl, isocyano, isocyanate group, thiocyanate group, isothiocyanate group, hydroxyl, nitryl, $CF_3$ group, Cl, Br, F, crosslinkable group, aromatic cyclic group containing 5 to 40 C atoms, heteroaromatic cyclic group containing 5 to 40 C atoms, aryloxy containing 5 to 40 C atoms and heteroaryloxy containing 5 to 40 C atoms. Wherein, $R^4$ and $R^5$ may form aliphatic or aromatic cyclic groups by bonding with each other, and $R^4$ and $R^{53}$ may also form aliphatic or aromatic cyclic groups by bonding with themselves, respectively. Wherein, the crosslinkable groups refer to functional groups containing unsaturated bonds such as alkenyl and alkynyl.

Further, $R^4$ and $R^5$ are each selected from at least one of the group consisting of H, D, linear alkyl containing 1 to 10 C atoms, alkoxy containing 1 to 10 C atoms, thioalkoxy group containing 1 to 10 C atoms, branched alkyl containing 3 to 10 C atoms, cyclic alkyl containing 3 to 10 C atoms, silyl group containing 3 to 10 C atoms, substituted keto containing 1 to 10 C atoms, alkoxycarbonyl containing 2 to 10 C atoms, aryloxycarbonyl containing 7 to 10 C atoms, cyano group, carbamoyl group, halocarbonyl group, formyl group, isocyano group, isocyanate group, thiocyanate group, isothiocyanate group, hydroxyl group, nitryl group, $CF_3$ group, Cl, Br, F, crosslinkable group, aryl containing 5 to 20 C atoms, heteroaromatic cyclic group containing 5 to 20 C atoms, aryloxy containing 5 to 20 C atoms and heteroaryloxy containing 5 to 20 C atoms. Wherein, $R^4$ and $R^5$ may form aliphatic or aromatic cyclic groups by bonding with each other, and $R^4$ and $R^5$ may also form aliphatic or aromatic cyclic groups by bonding with themselves, respectively. Wherein, the crosslinkable groups refer to functional groups containing unsaturated bonds such as alkenyl and alkynyl.

Specifically, $Ar^1$ is selected from one of the following groups:

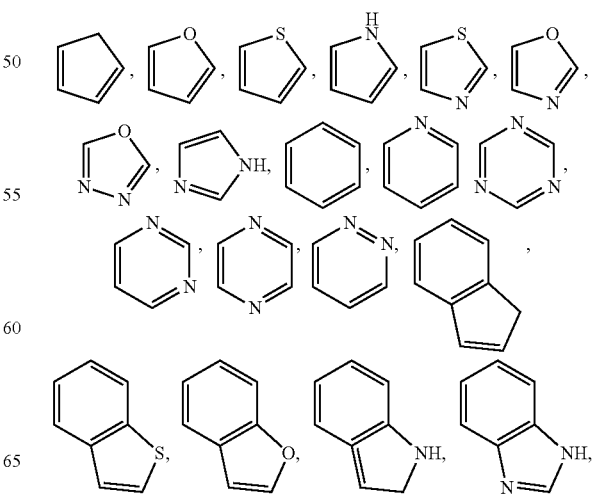

-continued

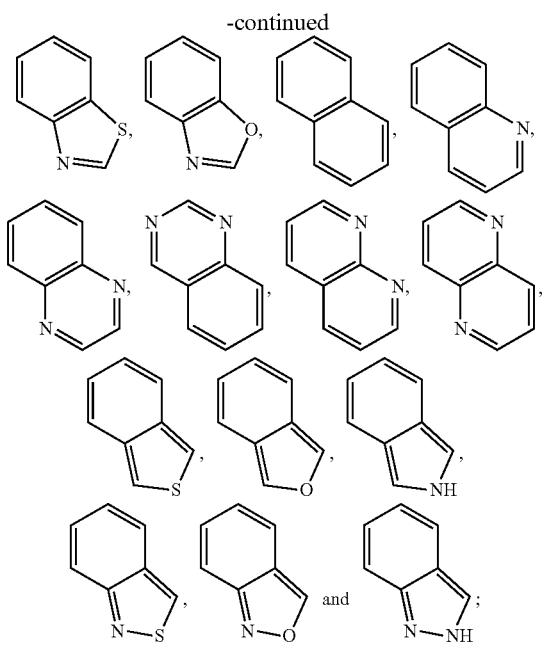

wherein, H in the group may be further substituted.

Wherein, Ar² is selected from one of the following general formulas:

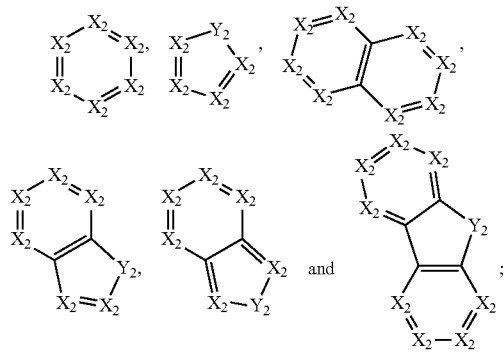

wherein, a plurality of $X_2$ are each independently selected from $CR^6$ or N, and at least one of the plurality of $X_2$ is N;

$Y_2$ is selected from $CR^6R^7$, $SiR^6R^7$, $NR^6$, $C(=O)$, S or O;

$R^6$ and $R^7$ are each selected from at least one of the group consisting of H, D, linear alkyl containing 1 to 20 C atoms, alkoxy containing 1 to 20 C atoms, thioalkoxy containing 1 to 20 C atoms, branched alkyl containing 3 to 20 C atoms, cyclic alkyl containing 3 to 20 C atoms, silyl containing 3 to 20 C atoms, substituted keto containing 1 to 20 C atoms, alkoxycarbonyl containing 2 to 20 C atoms, aryloxycarbonyl containing 7 to 20 C atoms, cyano, carbamoyl, halocarbonyl, formyl, isocyano, isocyanate group, thiocyanate group, isothiocyanate group, hydroxyl, nitryl, $CF_3$ group, Cl, Br, F, crosslinkable group, aromatic cyclic group containing 5 to 40 C atoms, heteroaromatic cyclic group containing 5 to 40 C atoms, aryloxy containing 5 to 40 C atoms and heteroaryloxy containing 5 to 40 C atoms. Wherein, $R^6$ and $R^7$ may form aliphatic or aromatic cyclic groups by bonding with each other, and $R^6$ and $R^7$ may also form aliphatic or aromatic cyclic groups by bonding with themselves, respectively. Wherein, the crosslinkable groups refer to functional groups containing unsaturated bonds such as alkenyl and alkynyl.

Specifically, Ar² is selected from one of the following groups:

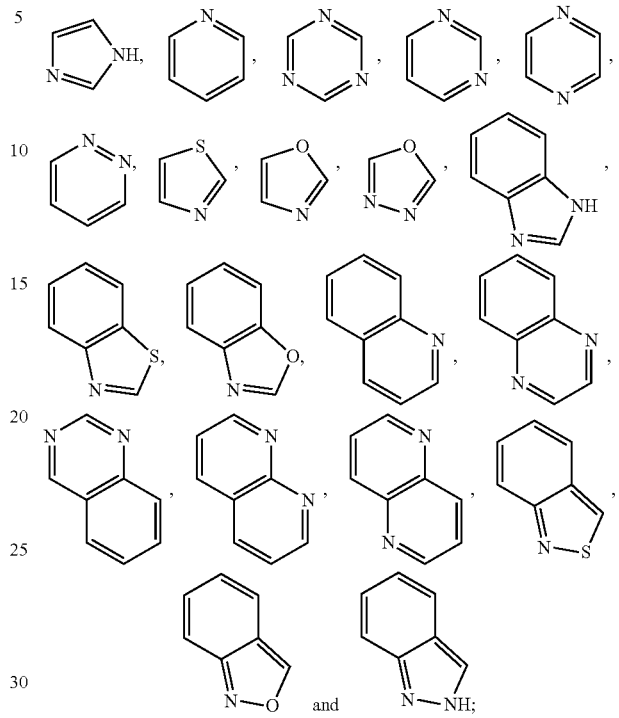

wherein, H in the group may be further substituted.

The metal organic complex of the present embodiment can act as a phosphorescent emitter whose emission wavelength depends on the triplet energy level $T_1$, and the ligand of the metal organic complex has a very important influence on its triplet energy level $T_1$.

The general formula of the ligand L0 of the metal organic complex is as follows, and the triplet energy level of the ligand L0 $T_1 \geq 2.0$ eV, further, $T_1 \geq 2.2$ eV, still further, $T_1 \geq 2.4$ eV, still further, $T_1 \geq 2.6$ eV, and even further, $T_1 \geq 2.7$ eV.

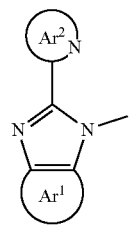

L0

La

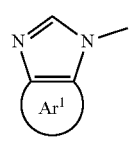

Lb

In the case where the substituent is removed, the number of C atoms of the substructure La of the ligand L0 does not exceed 26, further, the number of C atoms of the substructure La of the ligand L0 does not exceed 22, further, the number of C atoms of the substructure La of the ligand L0 does not exceed 20, and still further, the number of C atoms of the substructure La of the ligand L0 does not exceed 18.

In the case where the substituent is removed, the number of C atoms of the substructure Lb of the ligand L0 does not exceed 30, further, the number of C atoms of the substructure Lb of the ligand L0 does not exceed 26, further, the number of C atoms of the substructure Lb of the ligand L0 does not exceed 22, and still further, the number of C atoms of the substructure Lb of the ligand L0 does not exceed 20.

In an embodiment, S1(La)≥S1(Lb). In another embodiment, S1(Lb)≥S1(La). Wherein, S1(La) represents the first singlet excited state energy level of La, and S1(Lb) represents the first singlet excited state energy level of Lb.

In an embodiment, the metal organic complex is selected from one of the following formulas:

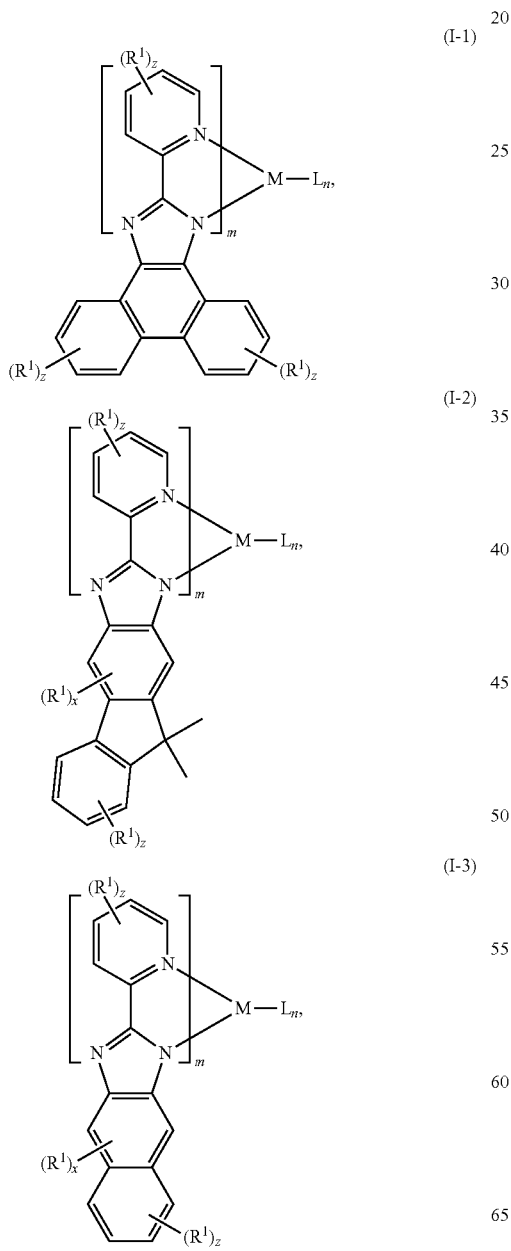

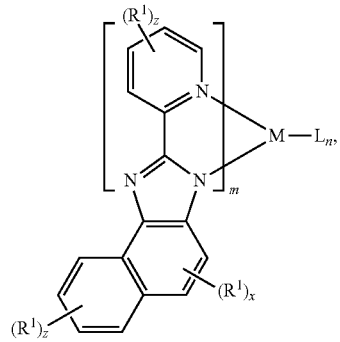

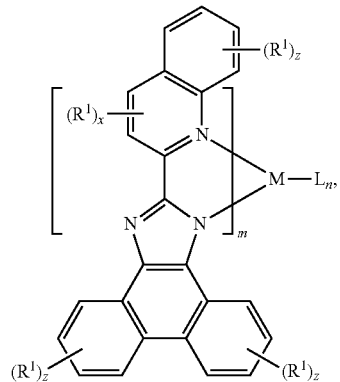

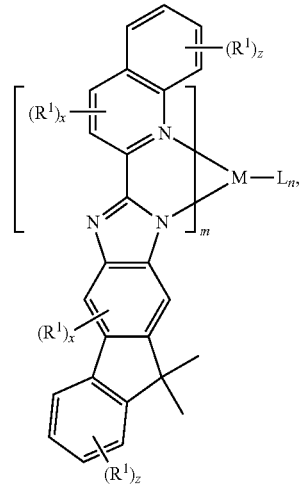

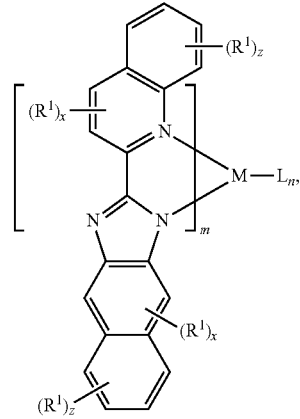

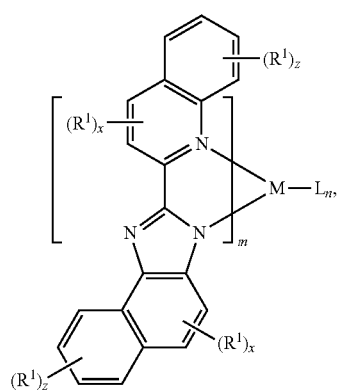
(I-8)
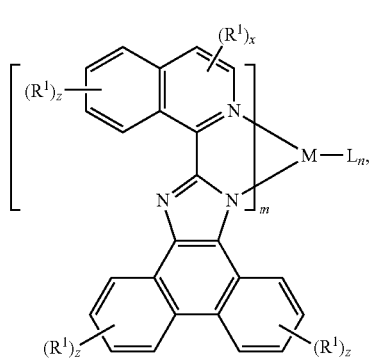
(I-9)
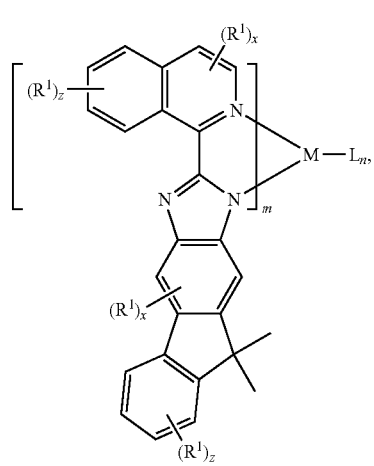
(I-10)
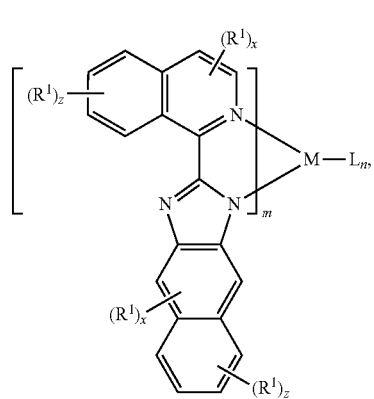
(I-11)
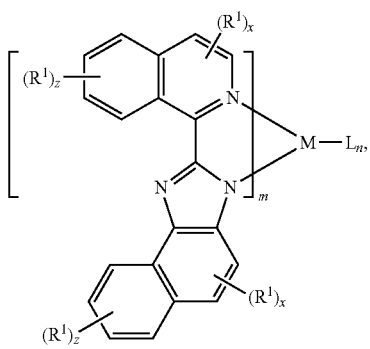
(I-12)
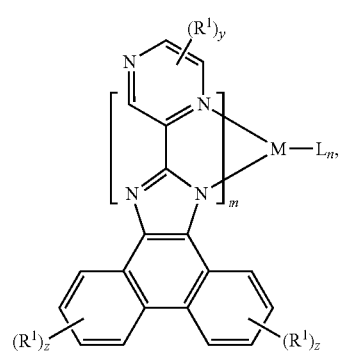
(I-13)
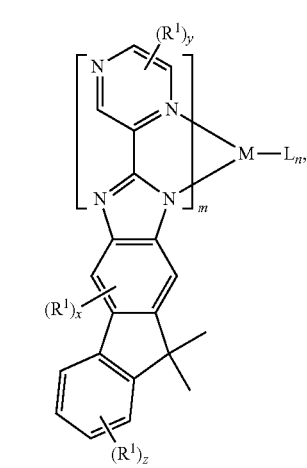
(I-14)
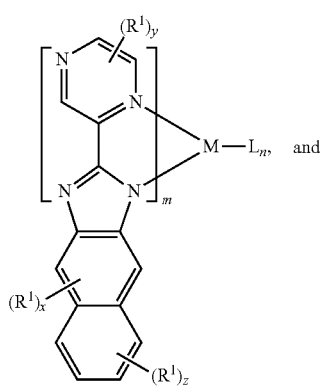
(I-15)
and -continued (I-16)

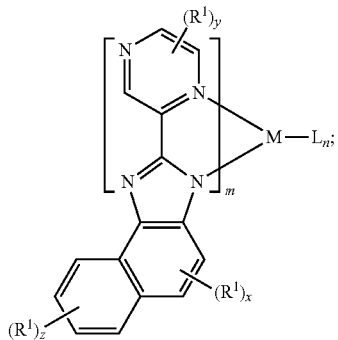

wherein, x is any integer from 0 to 2, y is any integer from 0 to 3, z is any integer from 0 to 4, and m is any integer from 1 to 3, and n is any integer from 0 to 2.

In one embodiment, m is 1. And m is not limited to 1, for example, m is 2. For another example, m is 3, as long as m is any integer from 1 to 3.

Wherein, L is selected from one of the following general formulas:

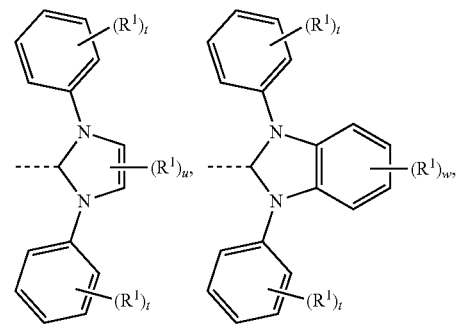

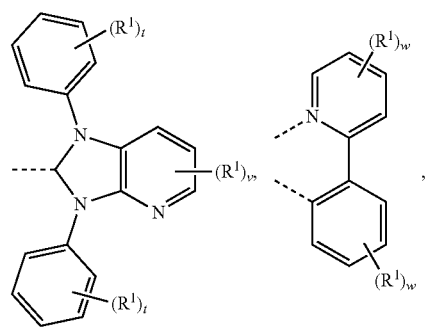

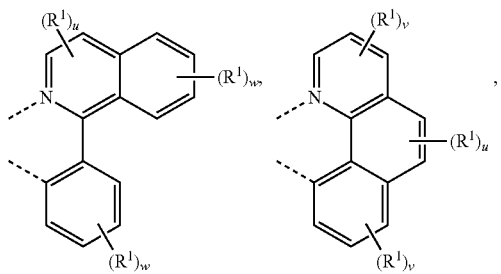

-continued

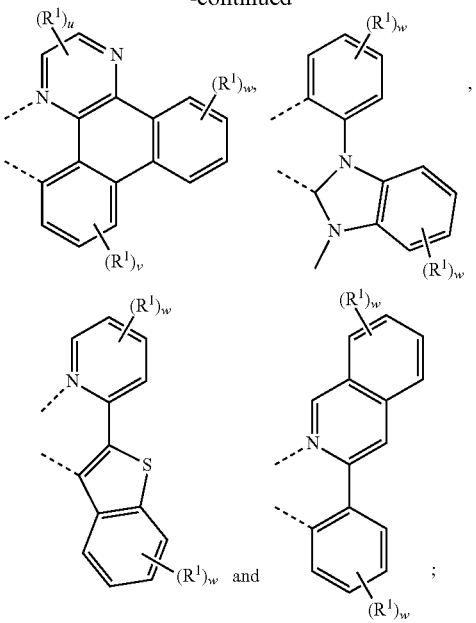

wherein, the dotted line represents the bond directly connected to M, u is any integer from 0 to 2, v is any integer from 0 to 3, w is any integer from 0 to 4, and t is any integer from 0 to 5.

In some embodiment, L is selected from one of the following general formulas:

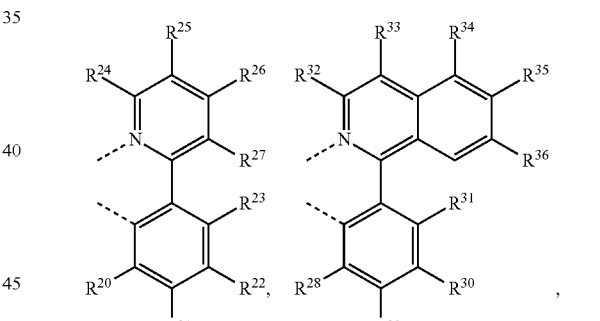

-continued

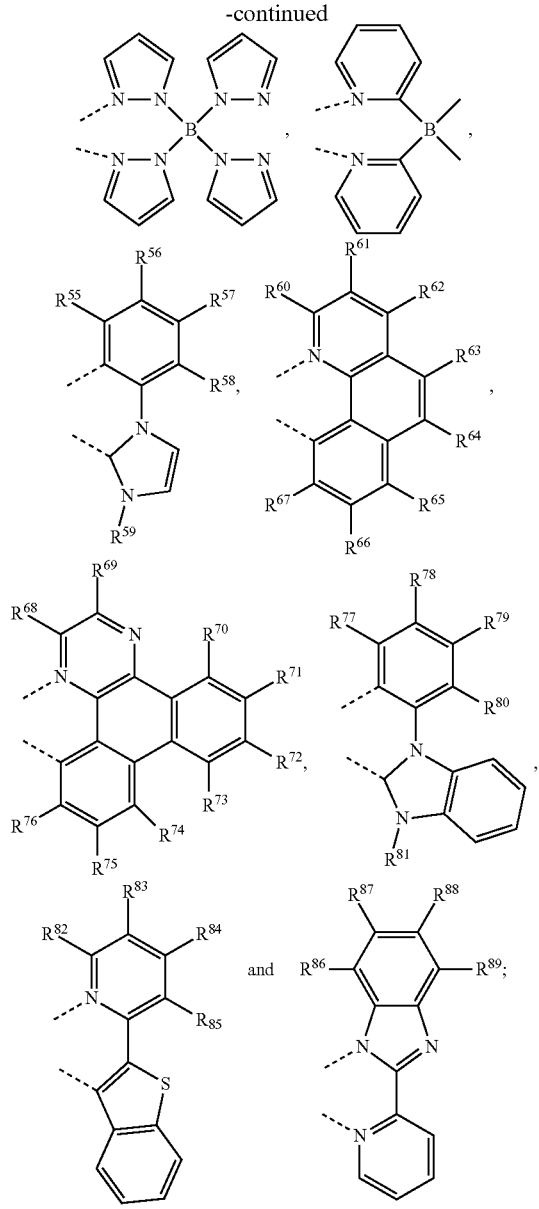

wherein, $R^{20}$ to $R^{89}$ are each selected from one of the group consisting of H, F, Cl, Br, I, D, CN, $NO_2$, $CF_3$, $B(OR^2)_2$, $Si(R^2)_3$, linear alkyl, alkyl ether group, alkyl thioether group containing 1 to 10 carbon atoms, branched alkyl containing 1 to 10 carbon atoms, cyclic alkyl containing 1 to 10 carbon atoms and aryl containing 6 to 10 carbon atoms.

M is a transitional metal element. Specifically, M is selected from one of the group consisting of chromium (Cr), molybdenum (Mo), tungsten (W), ruthenium (Ru), rhodium (Rh), nickel (Ni), silver (Ag), copper (Cu), zinc (Zn), palladium (Pd), gold (Au), osmium (Os), rhenium (Re), iridium (Ir) and platinum (Pt). Specially, M is selected from Cu, Au, Ir or Pt.

In view of the heavy atom effect, M is selected from Ir or Pt, and specially, M is Ir. Since Ir is chemically stable and has a significant heavy atom effect, it can produce high emitting efficiency. In terms of price advantage, M may also be Cu or Au.

Specifically, the metal organic complex is selected from, but not limited to one of the following structures:

(101)

(102)

(103)

(104)

(105)
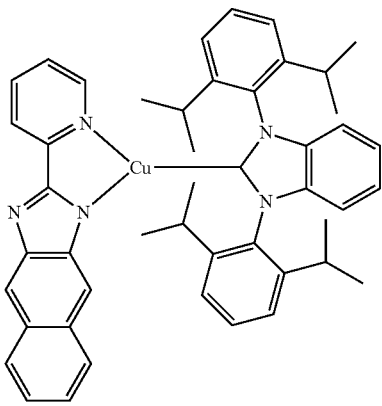
(106)
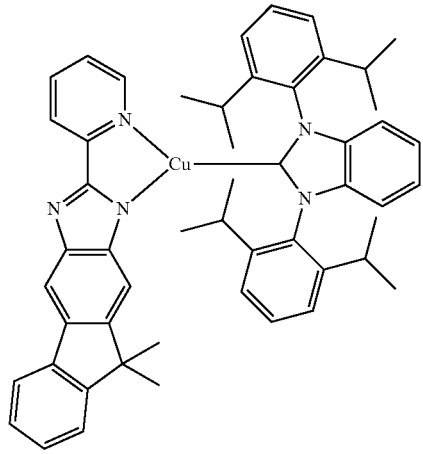
(107)
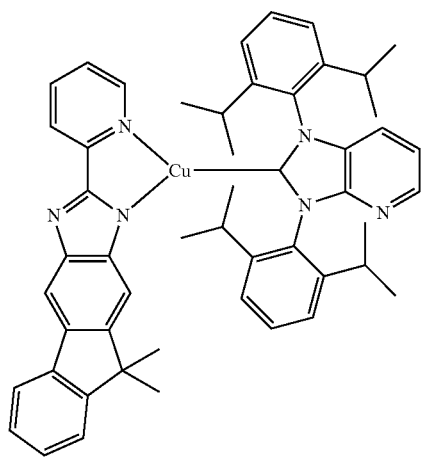
(108)
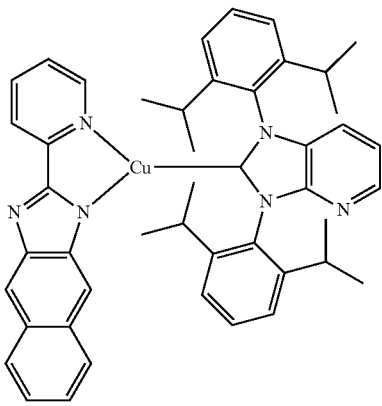
(109)
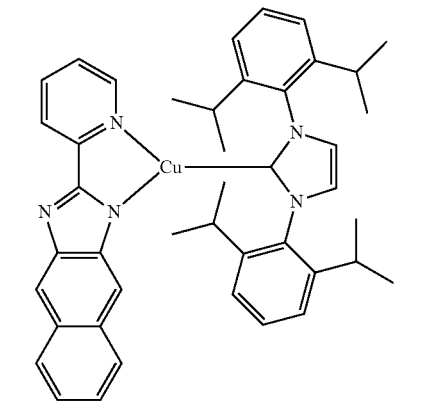
(110)
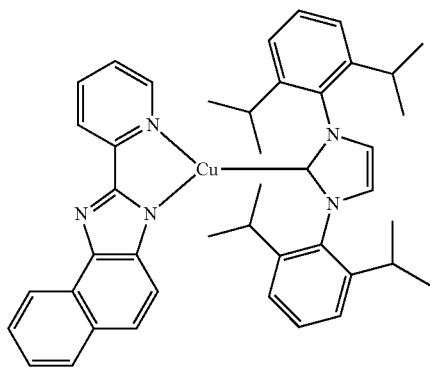
(111)
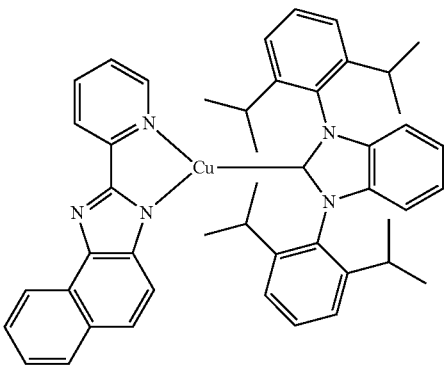

(112)
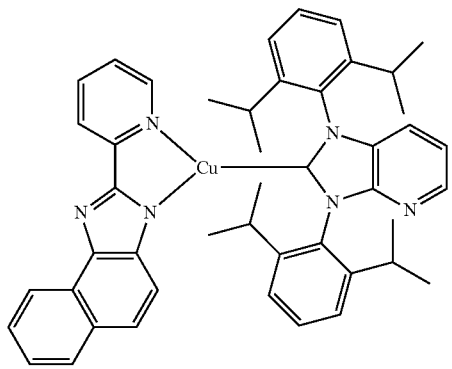
(116)
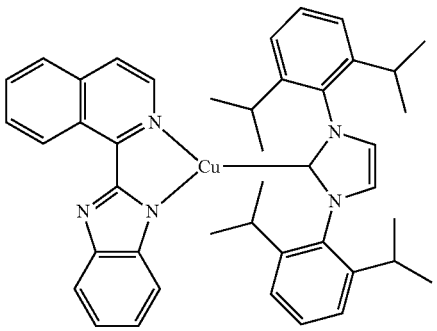
(113)
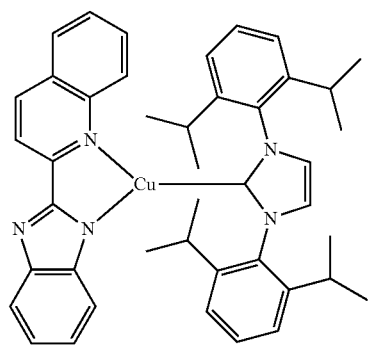
(117)
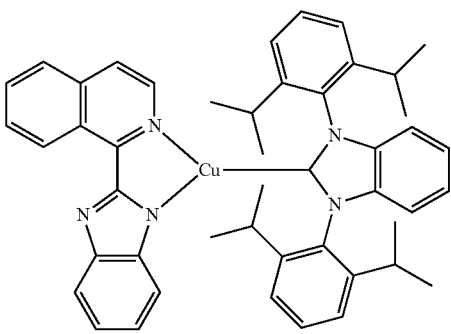
(114)
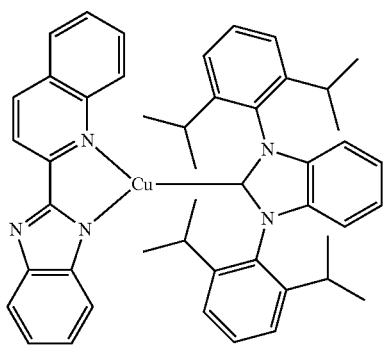
(118)
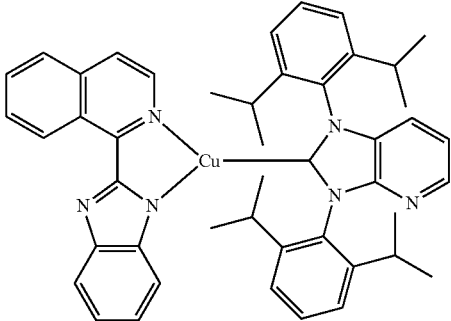
(115)
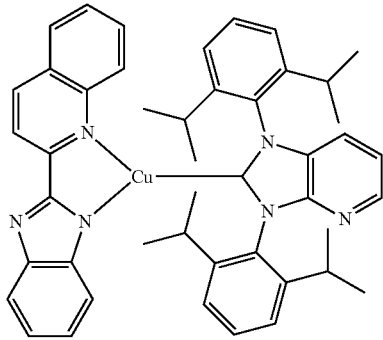
(119)
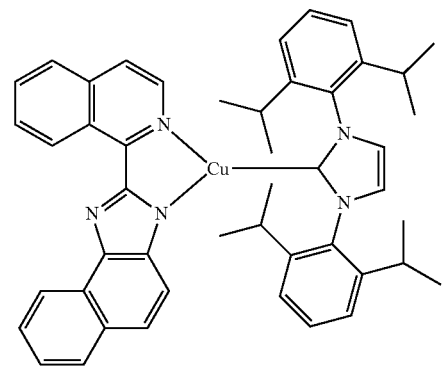

-continued
(120)
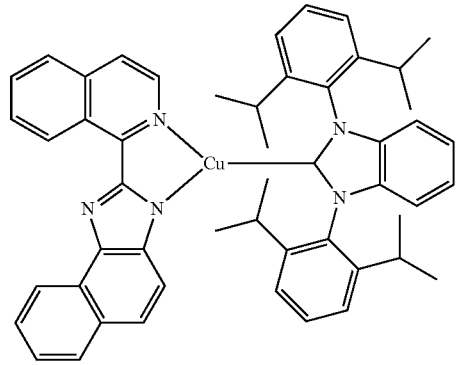
(121)
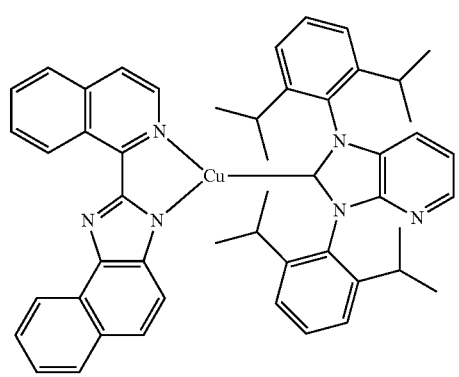
(122)
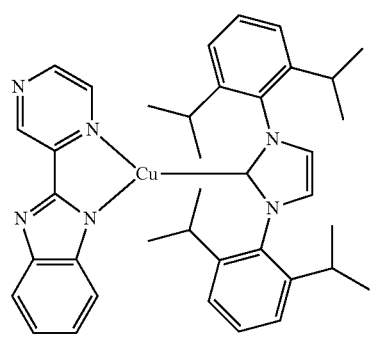
(123)
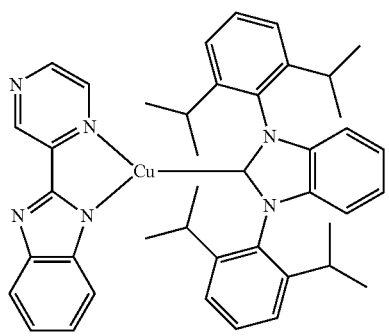
-continued
(124)
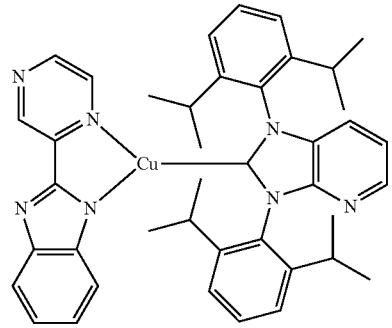
(125)
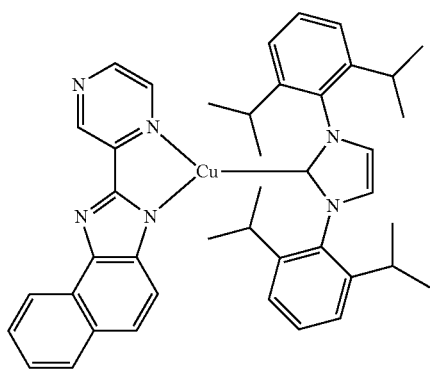
(126)
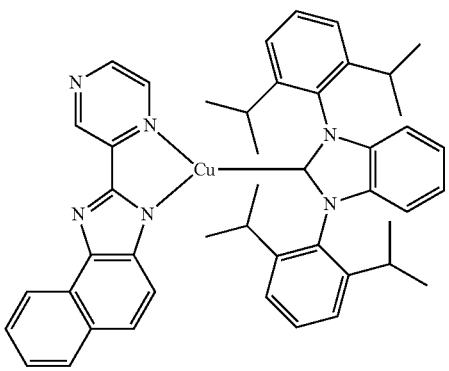
(127)
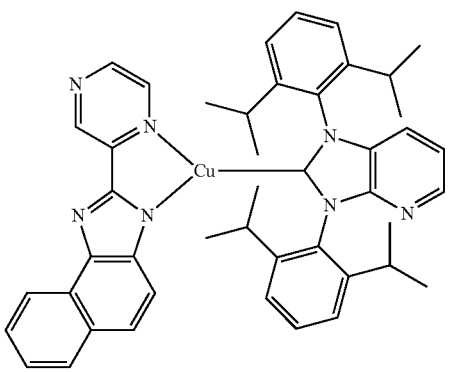

(128) 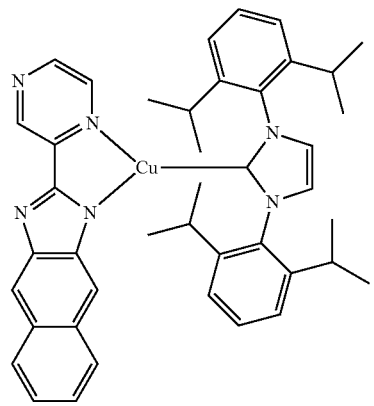
(129) 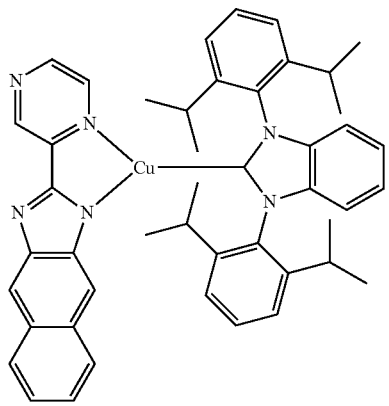
(130) 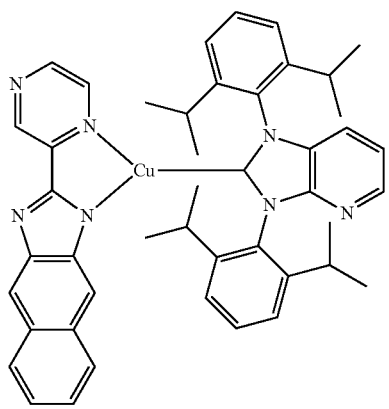
(131) 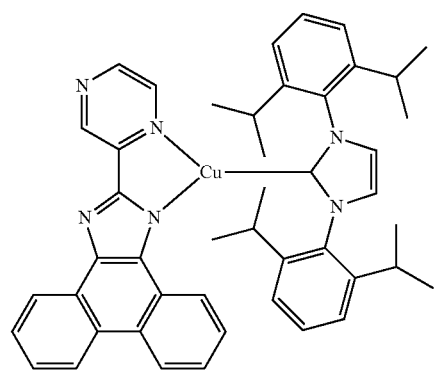
(132) 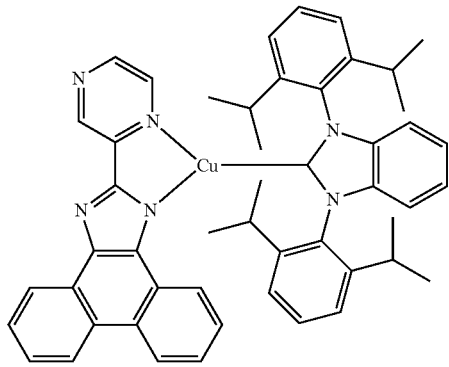
(133) 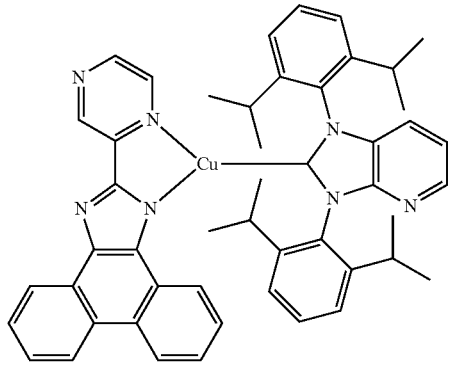
(134) 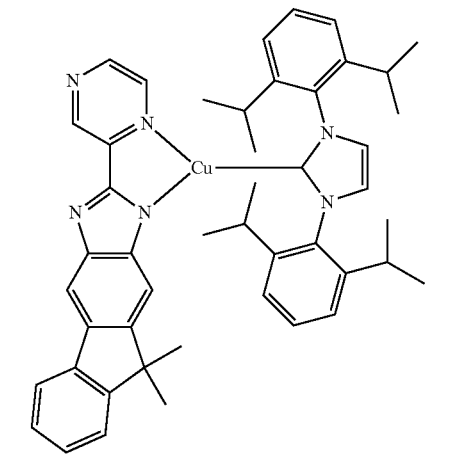
(135) 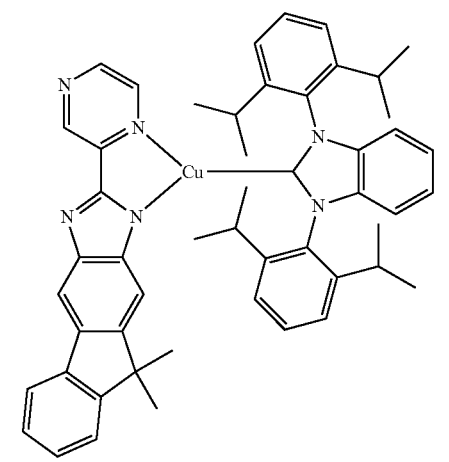

(136)
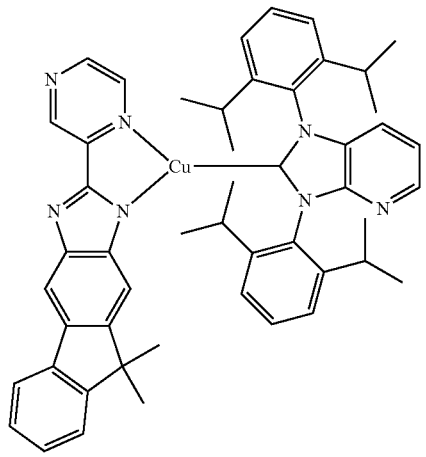
(137)
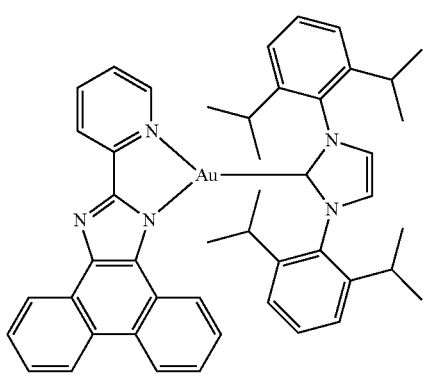
(138)
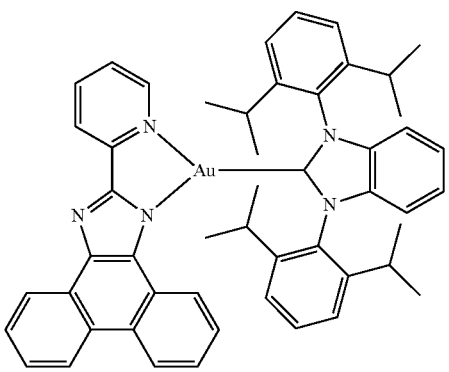
(139)
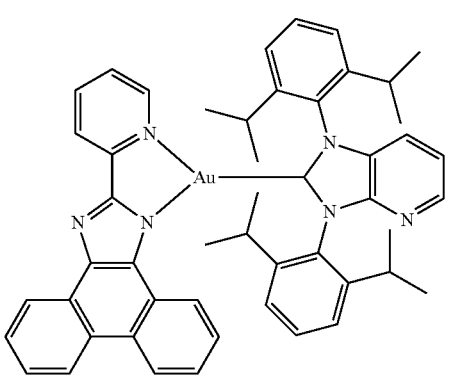
(140)
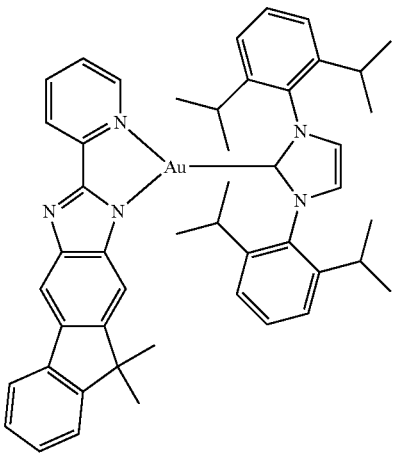
(141)
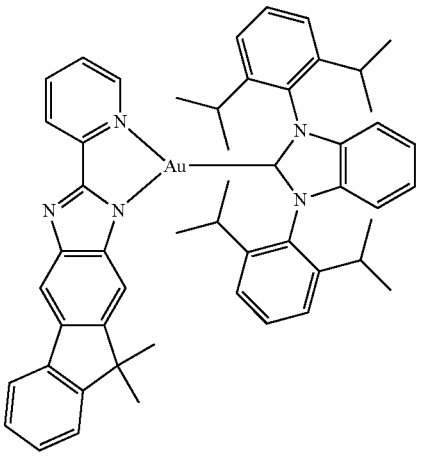
(142)
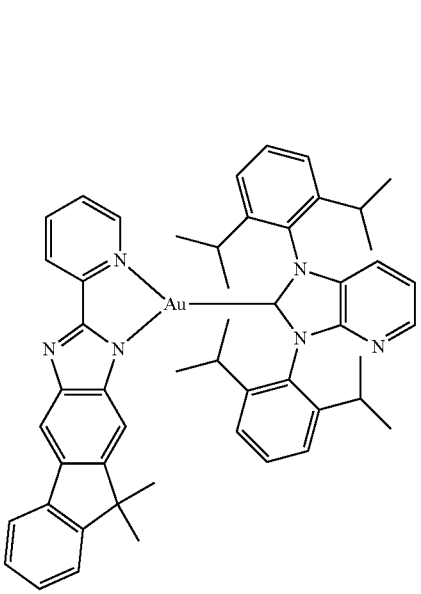

(143)
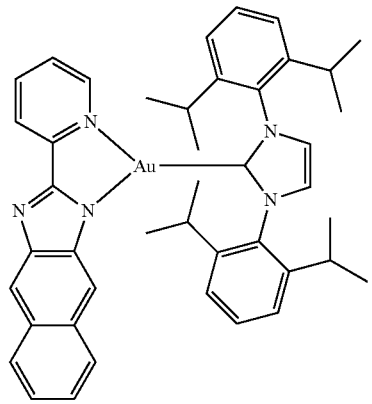
(144)
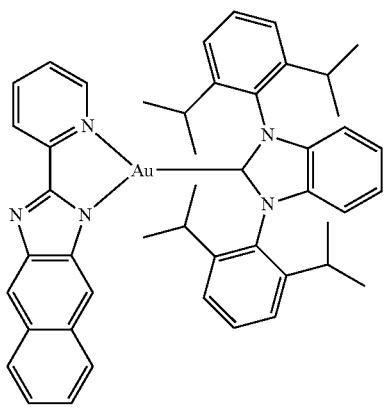
(145)
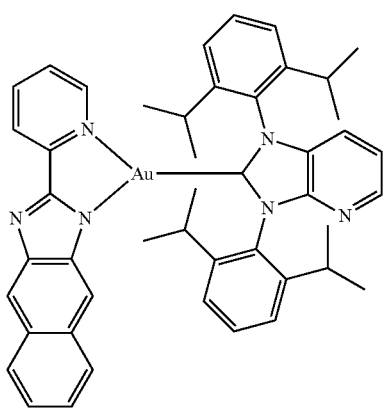
(146)
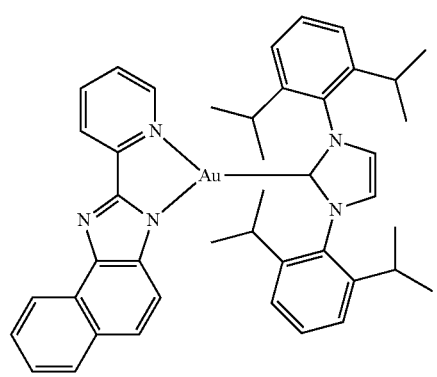
(147)
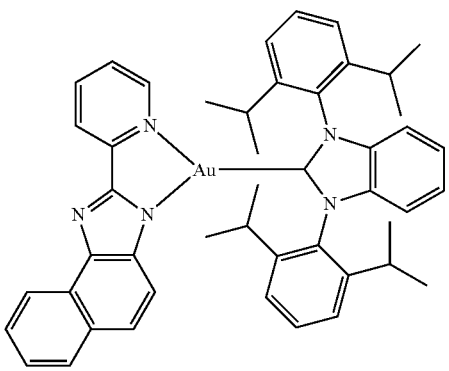
(148)
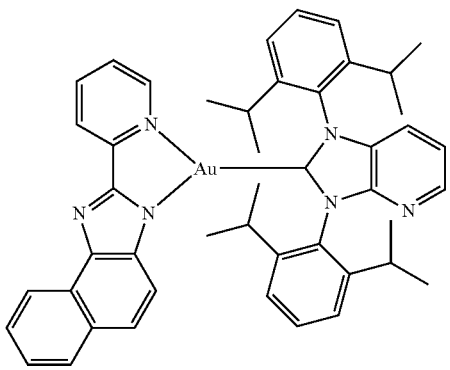
(149)
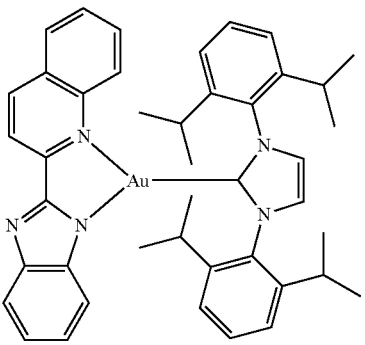
(150)
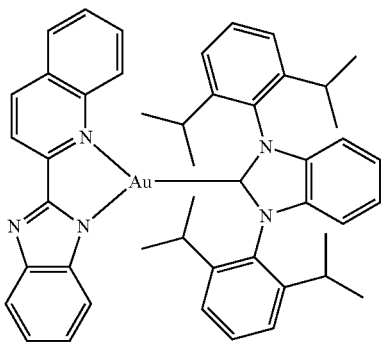

(151) 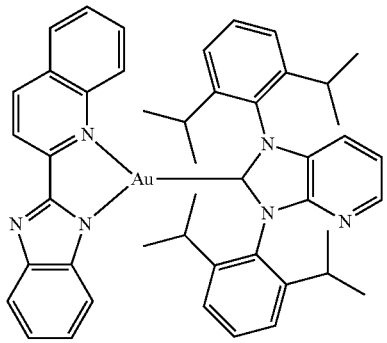
(155) 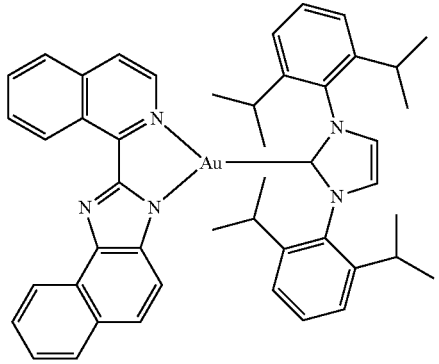
(152) 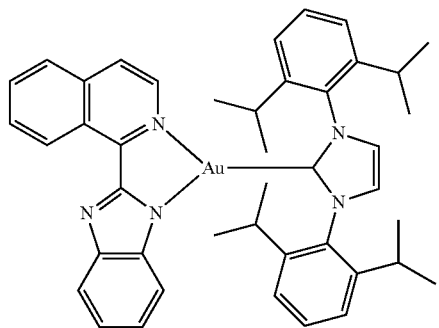
(156) 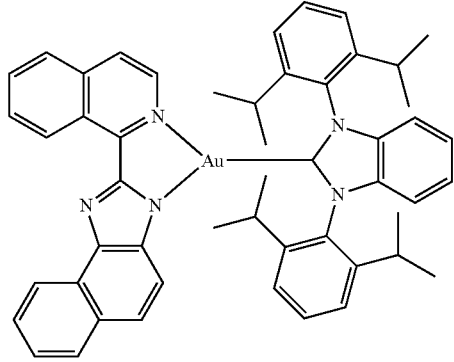
(153) 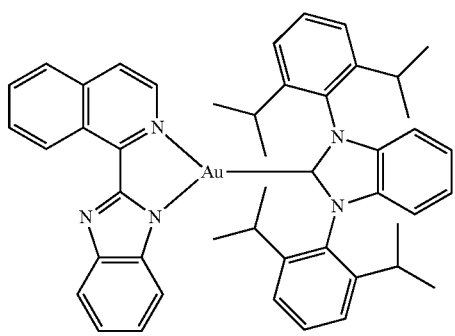
(157) 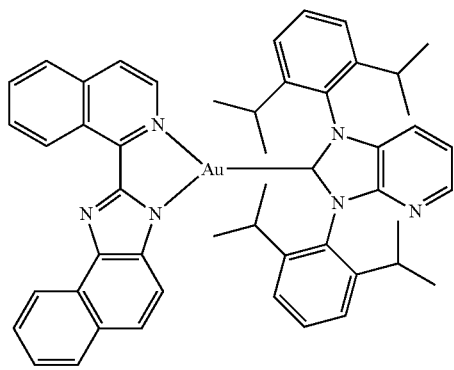
(154) 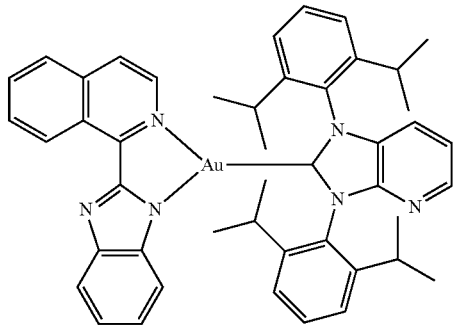
(158) 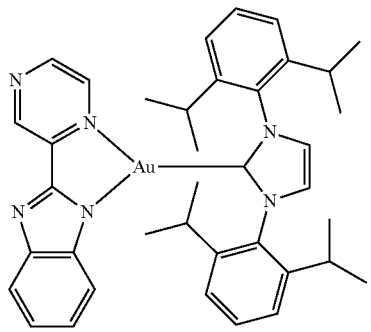

(159)
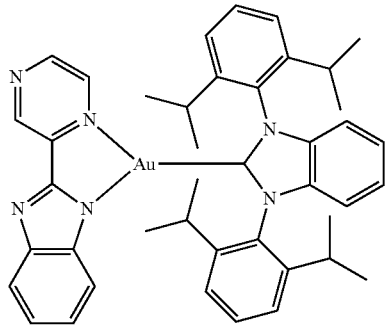
(160)
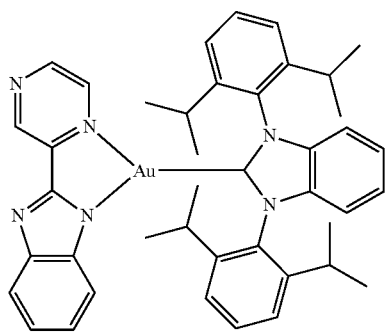
(161)
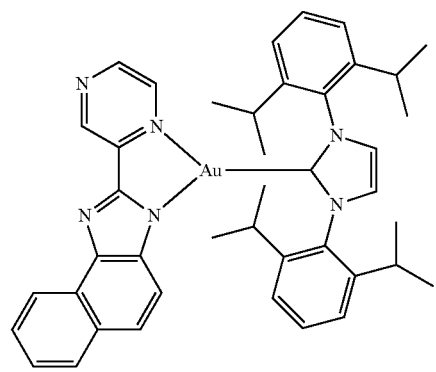
(162)
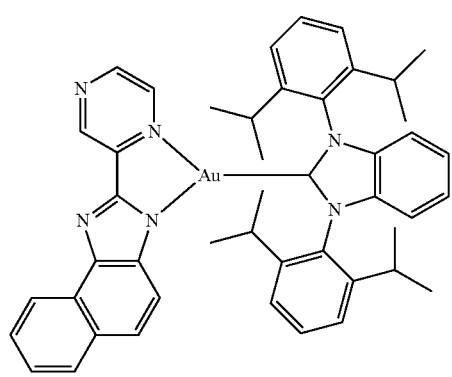
(163)
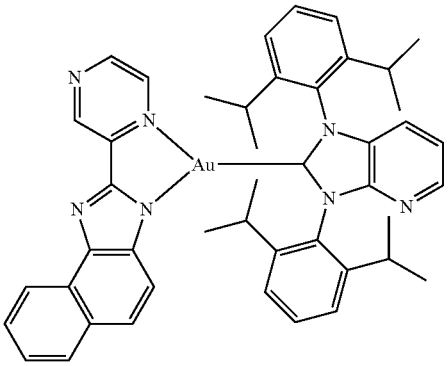
(164)
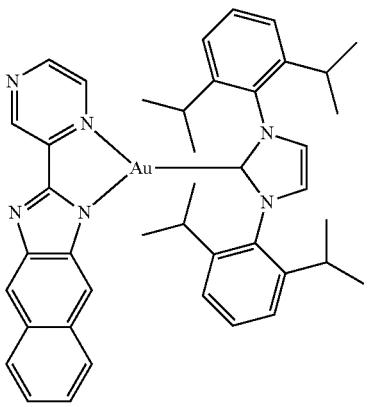
(165)
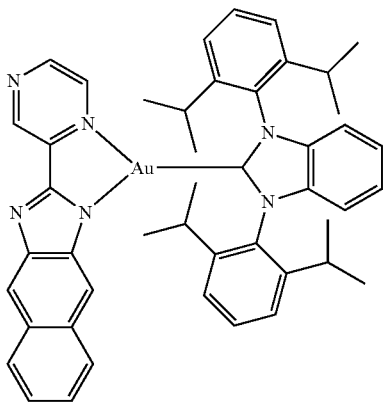
(166)
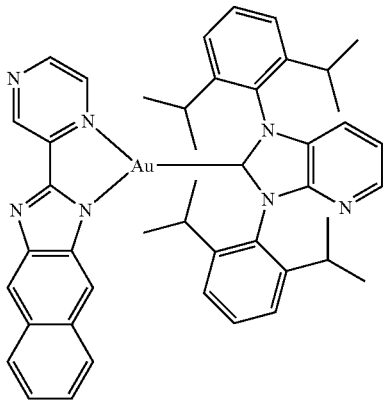

(167)
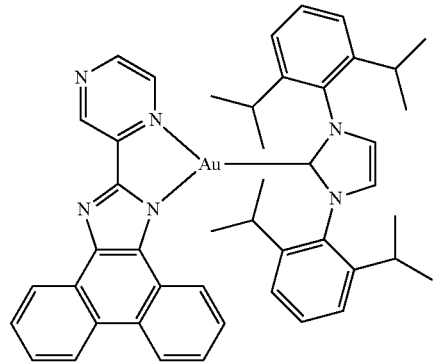
(168)
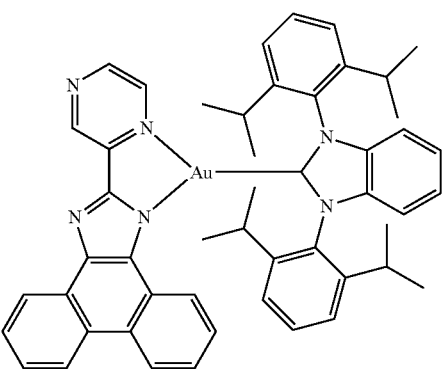
(169)
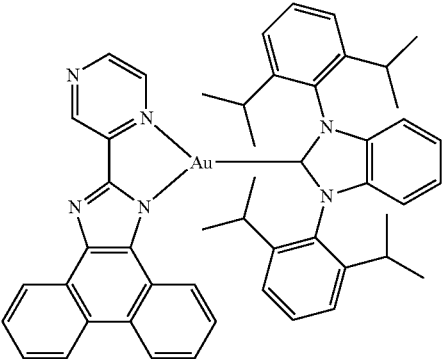
(170)
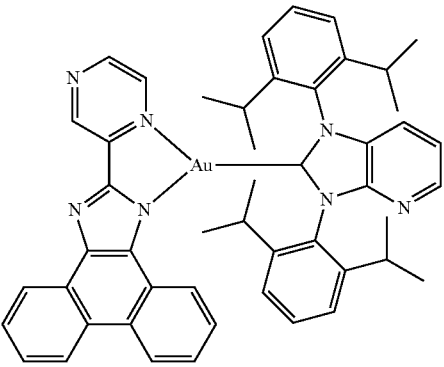
(171)
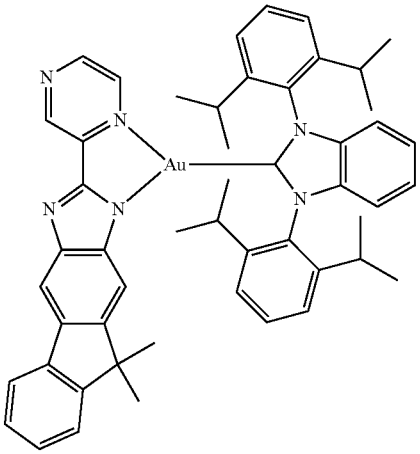
(172)
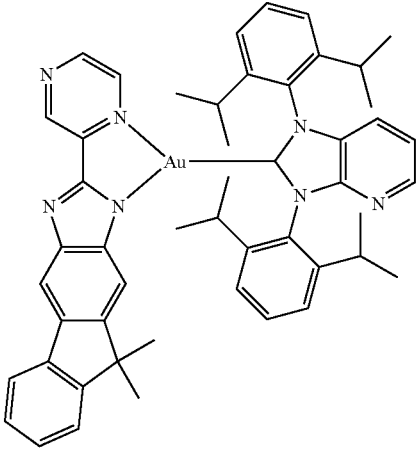
(173)
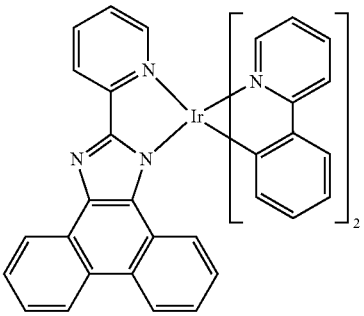
(174)
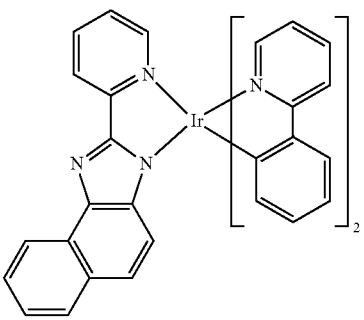
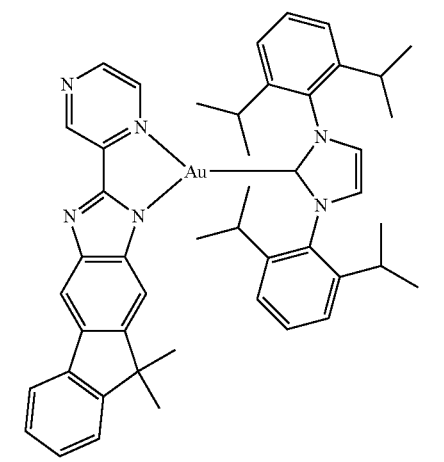

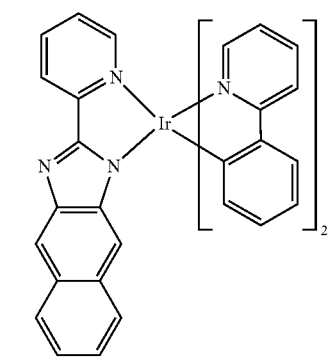
(175)
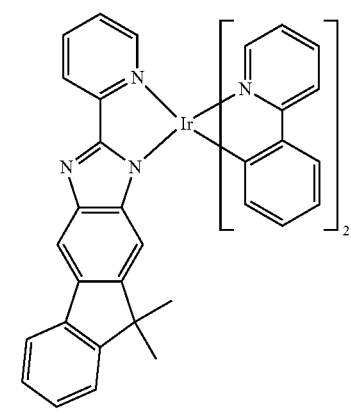
(176)
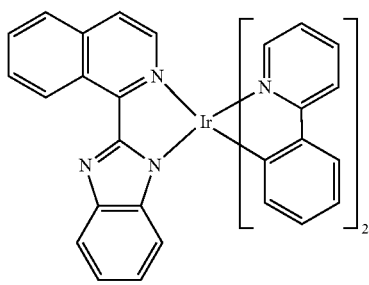
(177)
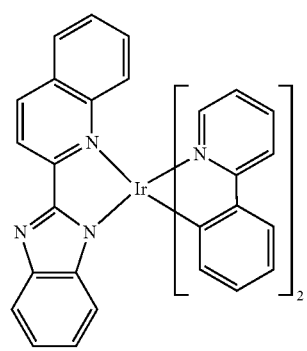
(178)
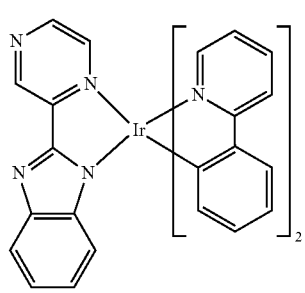
(179)
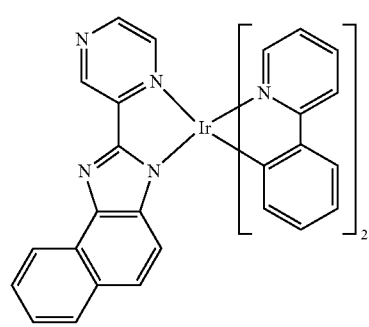
(180)
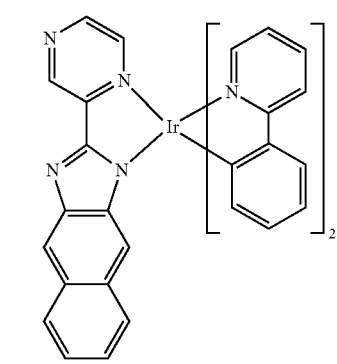
(181)
(182)
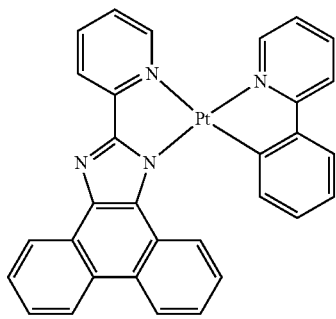
(183)

(184)
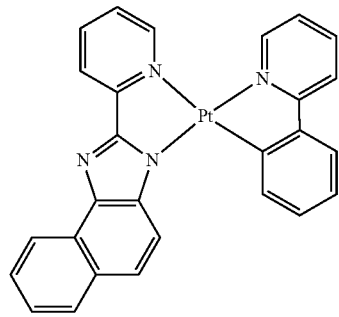
(185)
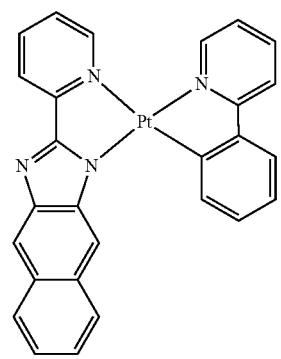
(186)
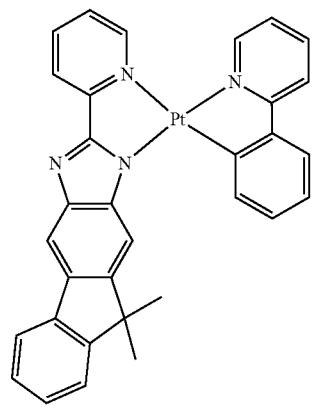
(187)
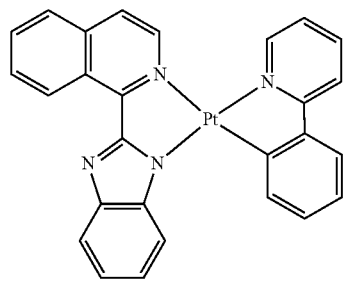
(188)
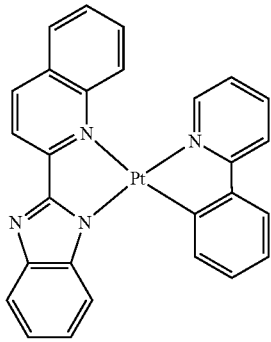
(189)
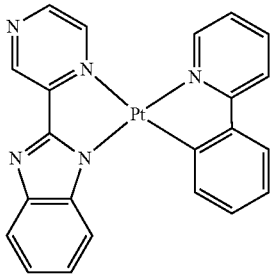
(190)
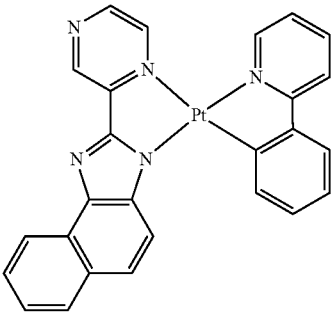
(191)
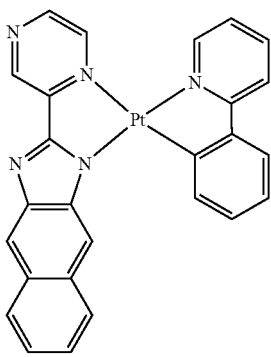
(192)
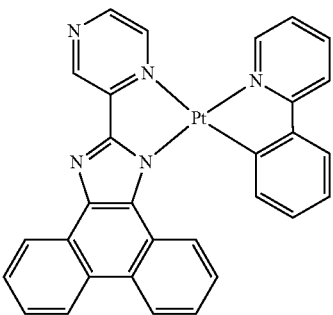

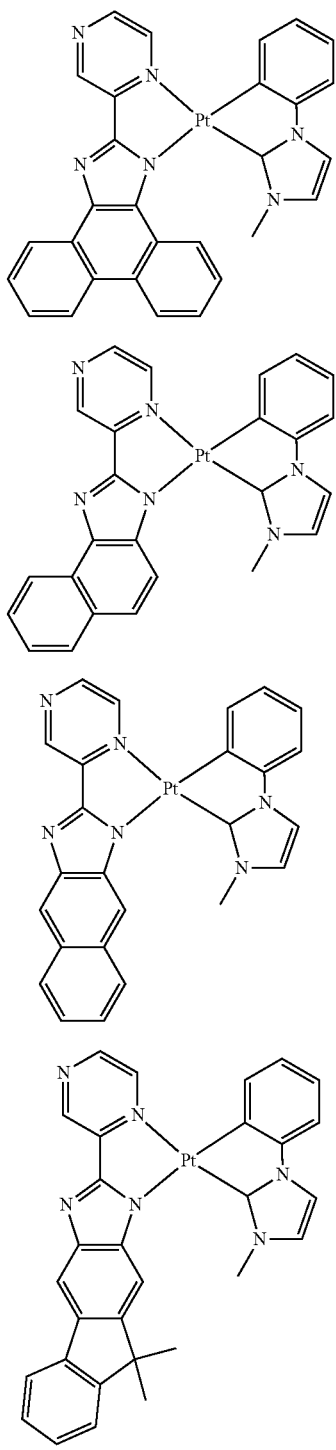

(193)
(194)
(195)
(196)

In an embodiment, when the metal organic complex is used as the material of evaporated OLEDs, the metal organic complex has a molecular weight of 1100 g/mol or less, further, the metal organic complex has a molecular weight of 1000 g/mol or less, still further, the metal organic complex has a molecular weight of 950 g/mol or less, still further, the metal organic complex has a molecular weight of 900 g/mol or less, and even further, the metal organic complex has a molecular weight of 800 g/mol or less.

When the metal organic complex is used as the material of printed OLEDs, the metal organic complex has a molecular weight no less than 700 g/mol, further, the metal organic complex has a molecular weight no less than 800 g/mol, still further, the metal organic complex has a molecular weight no less than 900 g/mol, still further, the metal organic complex has a molecular weight no less than 1000 g/mol, and even further, the metal organic complex has a molecular weight no less than 1100 g/mol.

When the metal organic complex is a light-emitting material, the metal organic complex has an emission wavelength of 300 nm to 1000 nm, further, the metal organic complex has an emission wavelength of 350 nm to 900 nm, and still further, the metal organic complex has an emission wavelength of 400 nm to 800 nm. Wherein, the light-emitting material refers to a photoluminescent material or an electroluminescent material.

In one embodiment, when the metal organic complex is a photoluminescent material, the photoluminescence efficiency of the metal organic complex is no less than 30%, further no less than 40%, still further no less than 50%, and specifically no less than 60%.

It should be noted that, the metal organic complex is not limited to a light-emitting material, and may be a non-luminescent material used as other functional materials such as an electron transport material, a hole transport material, a host material, an organic dye and the like.

The polymer according to one embodiment comprises a repeating unit comprising the above metal organic complex. The polymer comprises a non-conjugated polymer and a conjugated polymer. Particularly, the polymer is a conjugated polymer.

Polymer includes homopolymer, copolymer and block copolymer. In addition, in the present disclosure, the polymer also includes dendrimer. The synthesis and application of dendrimers are described in Dendrimers and Dendrons, Wiley-VCH Verlag GmbH & Co. KGaA, 2002, Ed. George R. Newkome, Charles N. Moorefield, Fritz Vogtle.

Conjugated polymer is a polymer whose backbone is primarily consisted of the $sp^2$ hybrid orbital of C atoms. Taking polyacetylene and poly (phenylene vinylene) as examples, the C atoms on the backbones of which may also be substituted by other non-C atoms, and which are still considered to be conjugated polymers when the $sp^2$ hybridization on the backbones is interrupted by some natural defects. In addition, the conjugated polymer in the present disclosure may also comprise aryl amine, aryl phosphine and other heteroarmotics, organometallic complexes, and the like on the backbone.

A film prepared from the above metal organic complex or the above polymer can be used to prepare organic electronic devices. Specifically, the film is prepared by spin coating.

The formulation according to one embodiment comprises the above metal organic complex and organic functional materials, or comprises the above polymer and organic functional materials. The organic functional materials may be small molecule materials or polymer materials. The small molecule herein refers to a molecule that is not a polymer, oligomer, dendrimer or blend. There are no repeating structures in small molecules. Wherein, the small molecule has a molecular weight of 3000 g/mol or less, further, the small molecule has a molecular weight of 2000 g/mol or less, and still further, the small molecule has a molecular weight of 1500 g/mol or less.

Specifically, the organic functional material is selected from the group consisting of a hole injection material (HIM), a hole transport material (HTM), an electron transport material (ETM), an electron injection material (EIM), an electron blocking material (EBM), a hole blocking material (HBM), a light-emitting material, a host material, and an organic dye.

Wherein, the light-emitting material is a singlet emitter (fluorescent emitter), a thermally activated delayed fluorescent material (TADF) or a triplet emitter (phosphorescent emitter). Further, the phosphorescent emitter is a light-emitting metal organic complex.

Specifically, the organic functional materials may be those disclosed in WO2010135519A1, US20090134784A1 and WO2011110277A1.

When the formulation comprises a metal organic complex and an organic functional material, the metal organic complex of the formulation has a mass percentage of 0.01% to 30%, further, the metal organic complex of the formulation has a mass percentage of 0.5% to 20%, still further, the metal organic complex of the formulation has a mass percentage of 2% to 15%, and specifically the metal organic complex of the formulation has a mass percentage of 5% to 15%.

In one embodiment, when the formulation comprises a metal organic complex and an organic functional material, the organic functional material is a triplet host material.

In another embodiment, when the formulation comprises a metal organic complex and an organic functional material, the organic functional material comprises a triplet host material and a triplet emitter.

In another embodiment, when the formulation comprises a metal organic complex and an organic functional material, the organic functional material is a thermally activated delayed fluorescent material (TADF).

In still another embodiment, when the formulation comprises a polymer and an organic functional material, the organic functional material is a thermally activated delayed fluorescent material (TADF).

The triplet host material, the triplet emitter and the TADF material are described in more detail below.

1. Triplet Host Material:

Any metal complex or organic compound may be used as the host for the triplet host material as long as its triplet energy is higher than that of the emitter, especially higher than that of the triplet emitter (phosphorescent emitter).

Specifically, the metal complex of the triplet host material has the following general formula:

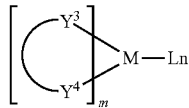

wherein, M is a metal; (Y³-Y⁴) is a bidentate ligand; Y³ and Y⁴ are each independently selected from one of C, N, O, P and S; L is an auxiliary ligand; m is an integer from 1 to the maximum coordination number of M; m+n is the maximum coordination number of M.

In an embodiment, M is selected from one of Cu, Au, Ir and Pt.

Further, the metal complex of the triplet host material has the following general formulas:

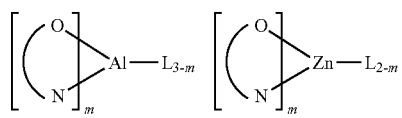

wherein, (O—N) is a bidentate ligand, and the metal is coordinated to the O atom and the N atoms.

Wherein, the organic compound that may be used as the triplet host material is a compound containing a cyclic aromatic hydrocarbyl or a compound containing an aromatic heterocyclic group. Wherein, the compound containing a cyclic aromatic hydrocarbyl includes benzene, biphenyl, triphenyl, benzo, fluorene; the compound containing an aromatic heterocyclic group includes dibenzothiophene, dibenzofuran, dibenzoselenophen, furan, thiophene, benzofuran, benzothiophene, benzoselenophene, carbazole, indolocarbazole, pyridine indole, pyrrole dipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, oxazole, dibenzoxazole, benzisoxazole, benzothiazole, quinoline, isoquinoline, cinnoline, quinazoline, quinoxaline, naphthalene, phthalein, pteridine, xanthene, acridine, phenazine, phenothiazine, phenoxazine, benzofuropyridine, furopyridine, benzothiophene pyridine, thiophene pyridine, benzoselenophenopyridine and selenophenodipyridine.

In addition, the organic compound that may be used as the triplet host material further may comprise a group containing 2-10 rings such as cyclic aromatic hydrocarbyl or aromatic heterocyclic group. Wherein, groups are coupled with each other directly or through at least one of oxygen atom, nitrogen atom, sulfur atom, silicon atom, phosphorus atom, boron atom, chain structure unit and aliphatic cyclic group. Further, each aromatic group (Ar) is substituted by one of hydrogen, alkyl, alkoxy, amino, alkenyl, alkynyl, aralkyl, heteroalkyl, aryl and heteroaryl.

In an embodiment, the organic compound of the triplet host material comprises at least one of the following groups:

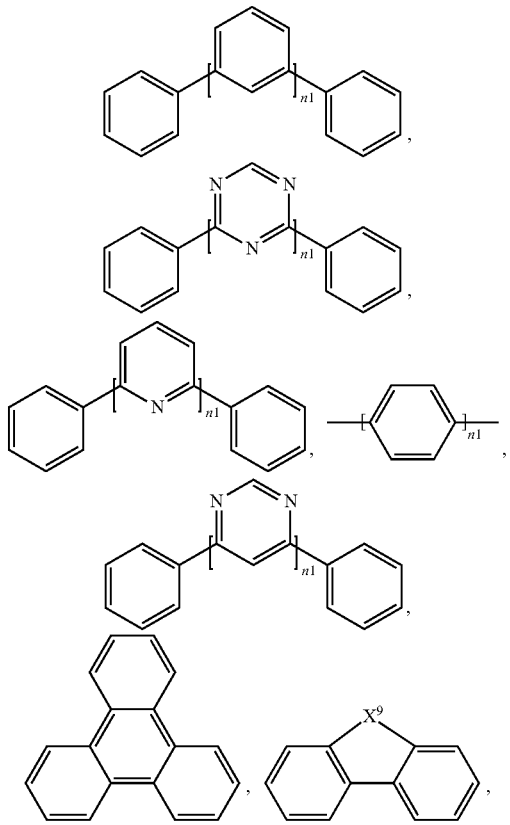

-continued

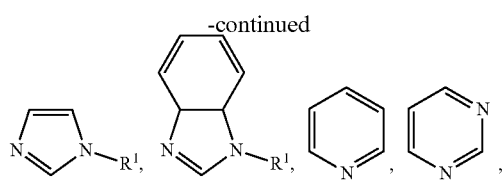

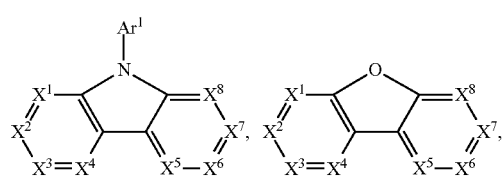

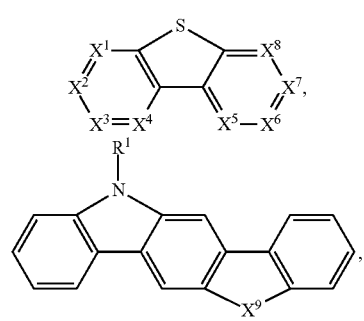

-continued

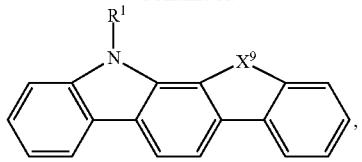

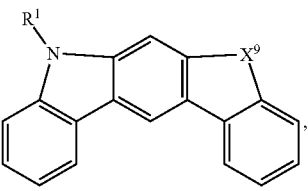

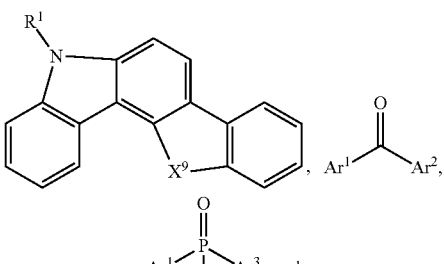

wherein, n1 is any integer from 0 to 20; $X^1$-$X^8$ are each selected from one of $CR_1$ and N; $X^9$ is selected from one of $CR_1R_2$ and $NR_1$; $R_1$-$R_7$ are each independently selected from hydrogen, alkyl, alkoxy, amino, alkenyl, alkynyl, aralkyl, heteroalkyl, aryl and heteroaryl.

Specifically, the triplet host material is selected from one of the following structures:

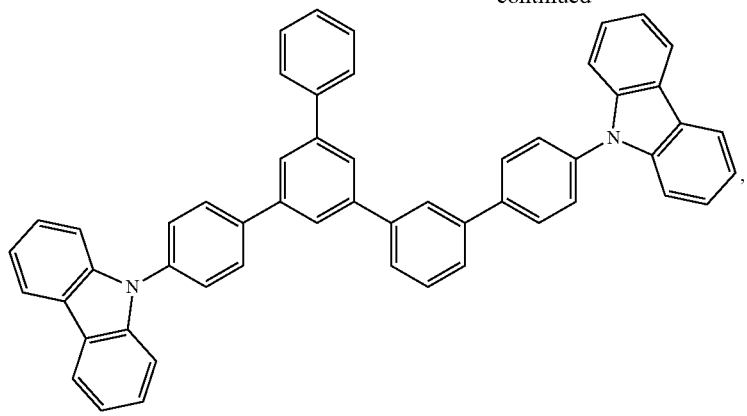

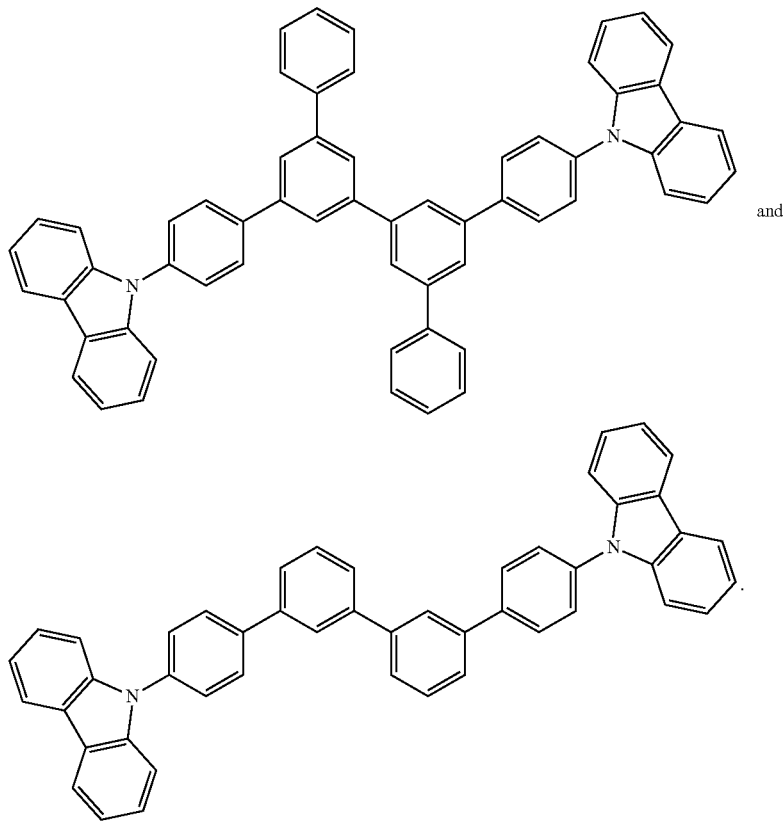

2. Triplet Emitter

Triplet emitters are also called phosphorescent emitters. The triplet emitter is a metal complex having the general formula M(L)n. Wherein M is a metal atom, L is an organic ligand which is bonded or coordinated to M through one or more positions; n is an integer greater than 1 and is particularly selected from 1, 2, 3, 4, 5 or 6.

In some embodiment, the metal complex is attached to a polymer through one or more positions. Specifically, the metal complex is coupled to a polymer through organic ligands.

In some embodiment, M is selected from one of a transitional metal element, a lanthanide element and a lanthanoid element. Specially, M is selected from one of Ir, Pt, Pd, Au, Rh, Ru, Os, Sm, Eu, Gd, Tb, Dy, Re, Cu and Ag. Particularly, M is selected from Os, Ir, Ru, Rh, Cu, Au or Pt.

Wherein, the triplet emitter contains a chelating ligand (i.e., a ligand) that coordinates with the metal through at least two binding sites. Specially, the triplet emitter comprises 2 to 3 bidentate or multidentate ligands. The chelating ligands are helpful to improve the stability of the metal complexes.

The organic ligand is selected from one of the group consisting of phenylpyridine derivatives, 7,8-benzoquinoline derivatives, 2(2-thienyl) pyridine derivatives, 2(1-naphthyl) pyridine derivatives and 2 phenylquinoline derivatives. Further, all of these organic ligands may be substituted, for example, substituted by fluoromethyl or trifluoromethyl. The auxiliary ligand is selected from one of acetylacetone and picric acid.

Specifically, the metal complex of the triplet emitter has the following general formula:

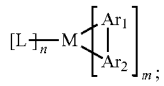

wherein, M is a metal; specially, M is selected from one of a transitional metal element, a lanthanide element and a lanthanoid element;

$Ar^1$ is a cyclic group and comprises at least one donor atom (i.e., an atom having one lone pair of electrons, such as nitrogen or phosphorus) through which the cyclic group is coordinately coupled with metal;

$Ar^2$ is a cyclic group and comprises at least one carbon atom through which the cyclic group is coupled with metal;

$Ar^1$ and $Ar^2$ are covalently bonded together, and each of them may carry one or more substituents, and they may be coupled together by substituents again;

L is an auxiliary ligand, and specially, L is a bidentate chelating ligand, particularly L is a monoanionic bidentate chelating ligand;

m is any integer from 1 to 3, further, m is 2 or 3, still further, m is 3;

n is any integer from 0 to 2, further, n is 0 or 1, still further, n is 0.

Wherein, triplet emitter materials and applications thereof may be those disclosed in the following documents: WO 200070655, WO 200141512, WO 200202714, WO 200215645, EP 1191613, EP 1191612, EP 1191614, WO 2005033244, WO 2005019373, US 2005/0258742, WO 2009146770, WO 2010015307, WO 2010031485, WO 2010054731, WO 2010054728, WO 2010086089, WO 2010099852, WO 2010102709, US 20070087219 A1, US 20090061681 A1, US 20010053462 A1, Baldo, Thompson et al. Nature 403, (2000), 750-753, US 20090061681 A1, US 20090061681 A1, Adachi et al. Appl. Phys. Lett. 78 (2001), 1622-1624, J. Kido et al. Appl. Phys. Lett. 65 (1994), 2124, Kido et al. Chem. Lett. 657, 1990, US 2007/0252517 A1, Johnson et al., JACS 105, 1983, 1795, Wrighton, JACS 96, 1974, 998, Ma et al., Synth. Metals 94, 1998, 245, U.S. Pat. Nos. 6,824,895, 7,029,766, 6,835,469, 6,830,828, US 20010053462 A1, WO 2007095118 A1, US 2012004407A1, WO 2012007088A1, WO2012007087A1, WO 2012007086A1, US 2008027220A1, WO 2011157339A1, CN 102282150A and WO 2009118087A1.

Specifically, the triplet emitter may be selected from one of the following structures:

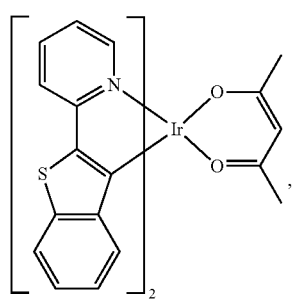

-continued

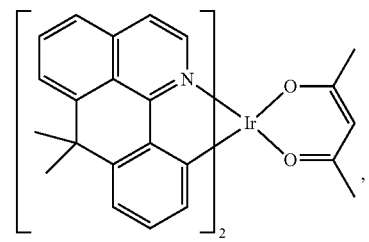

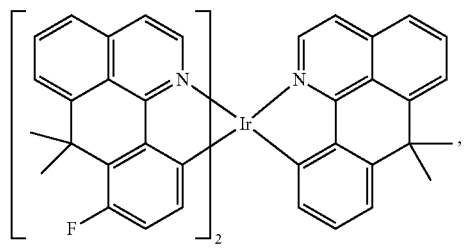

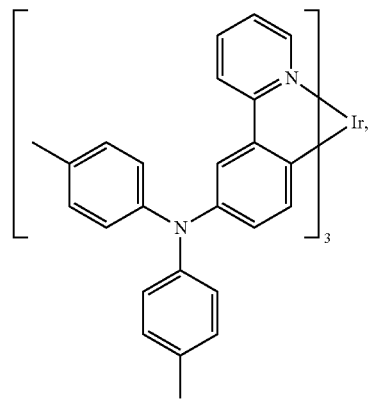

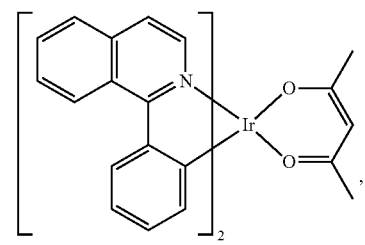

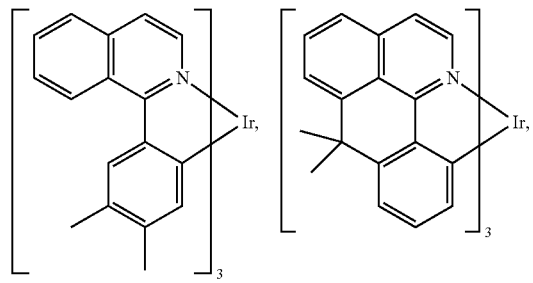

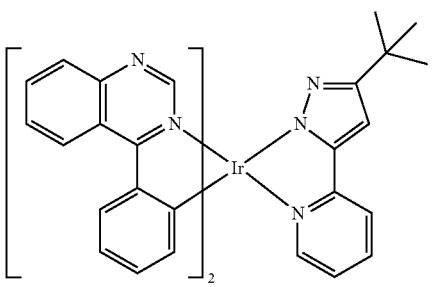

49
-continued
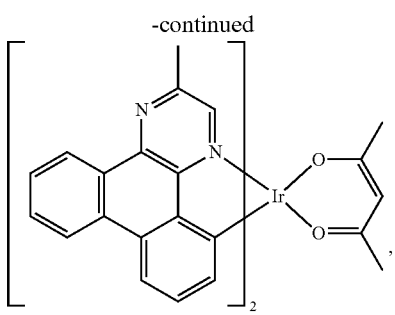
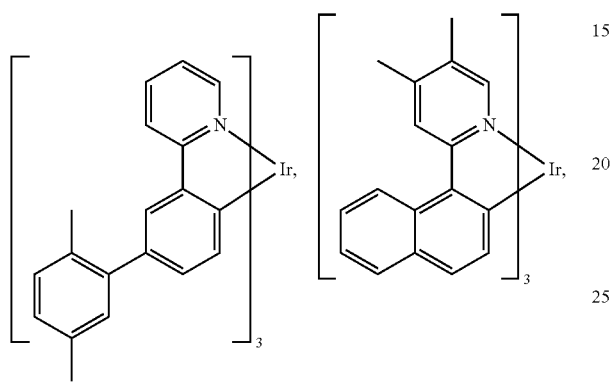
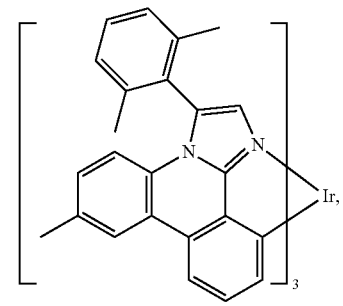
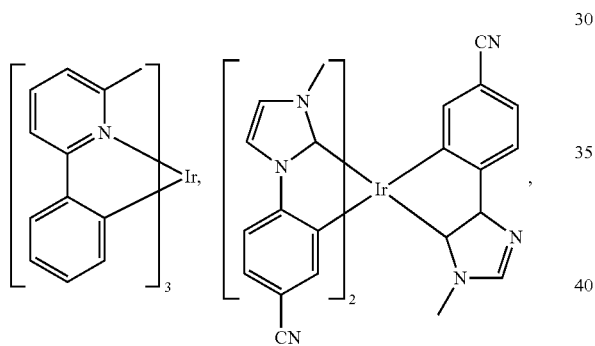
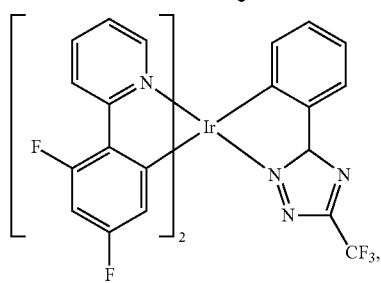
50
-continued
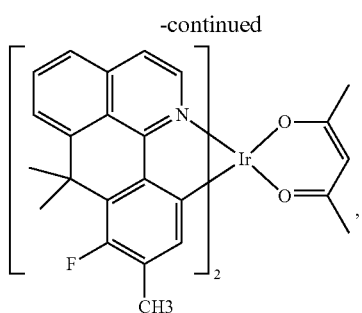
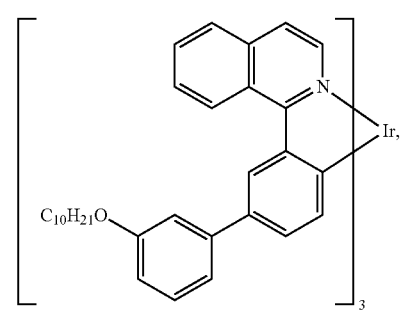
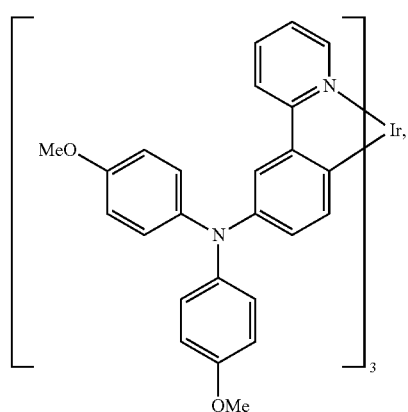
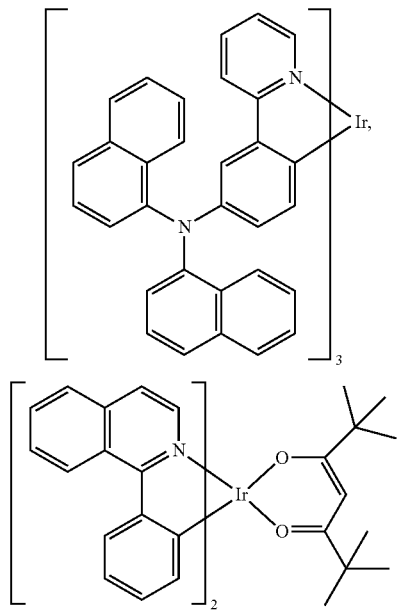

51
-continued
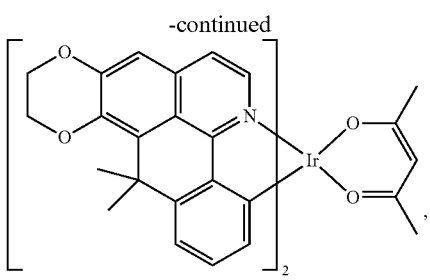
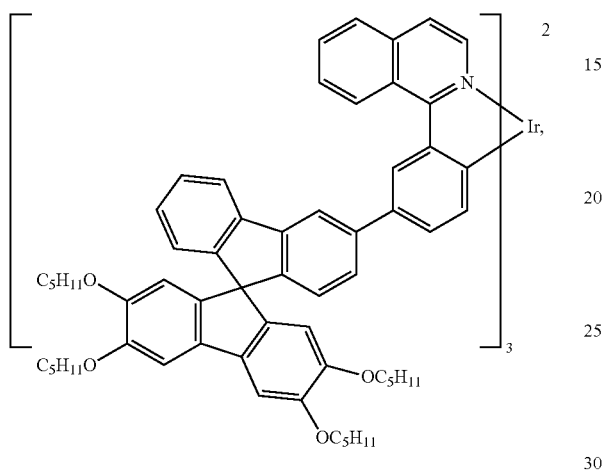
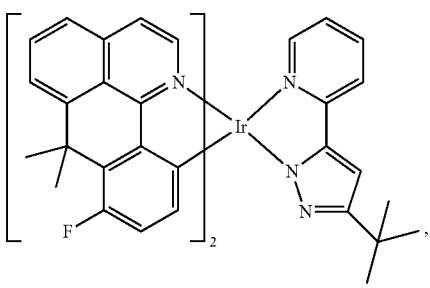
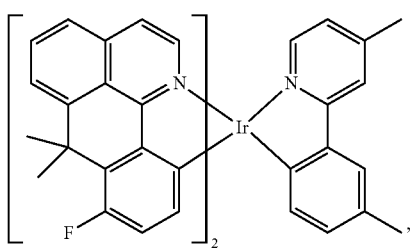
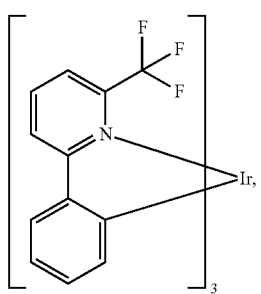
52
-continued
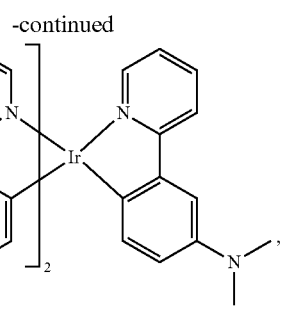
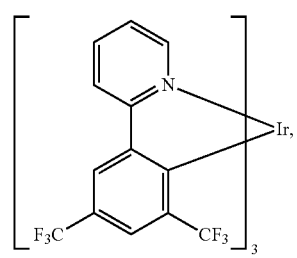
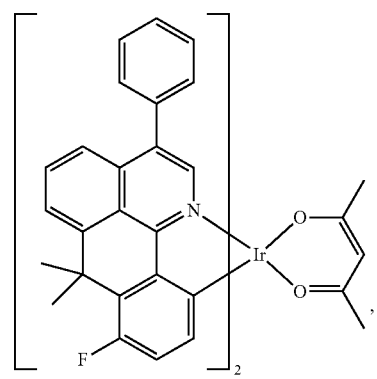
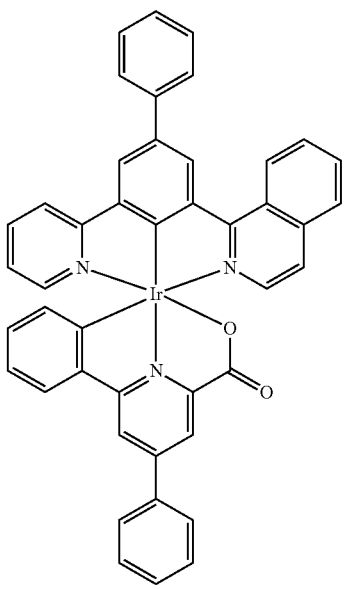

53
-continued
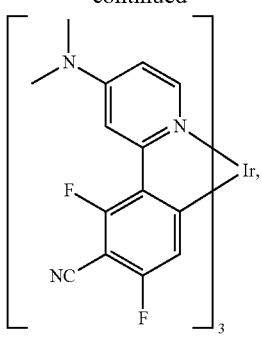
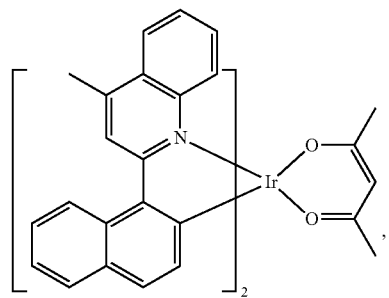
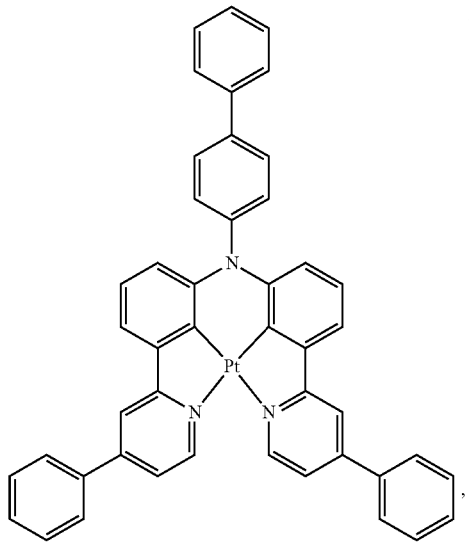
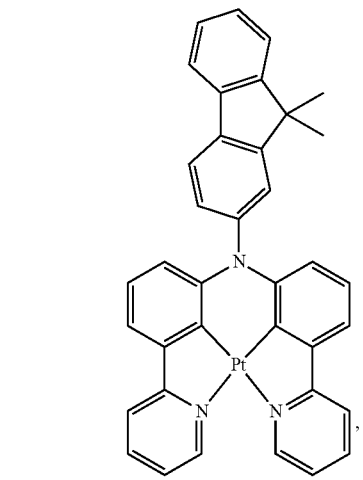
54
-continued
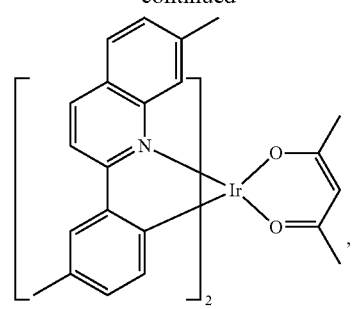
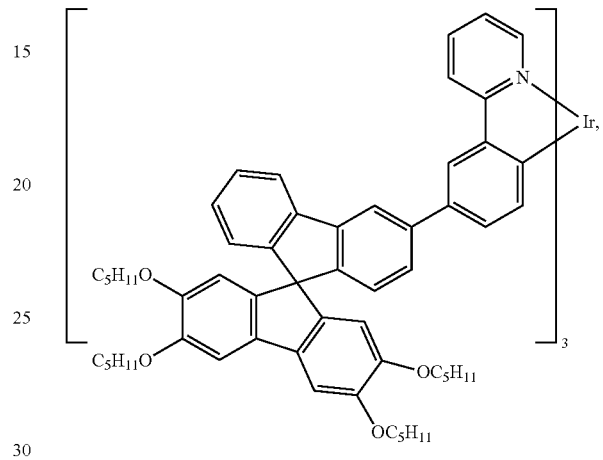
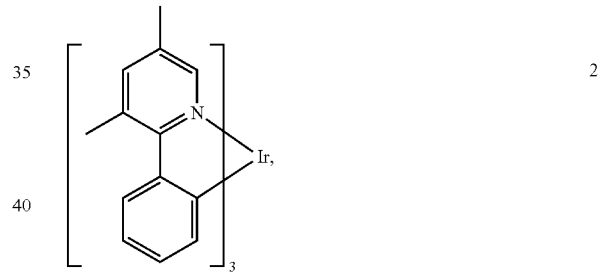
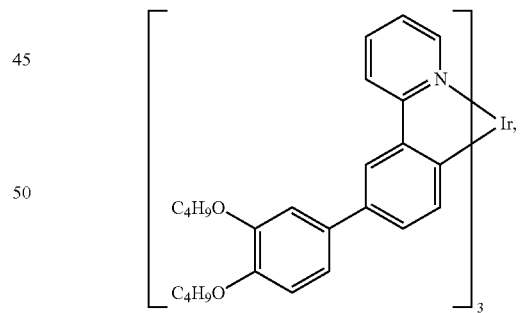
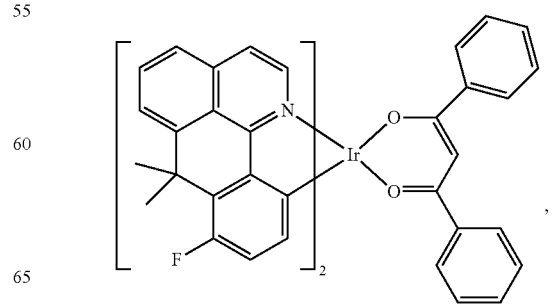

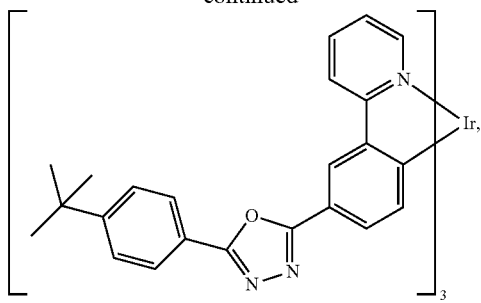

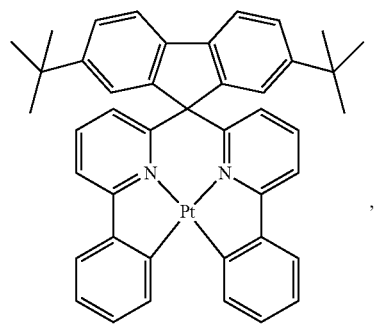

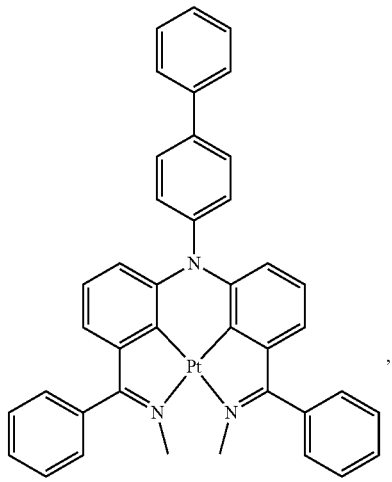

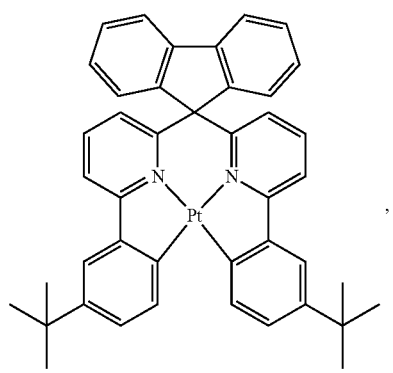

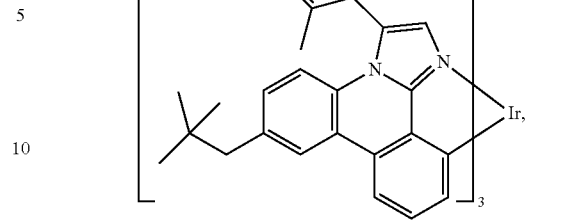

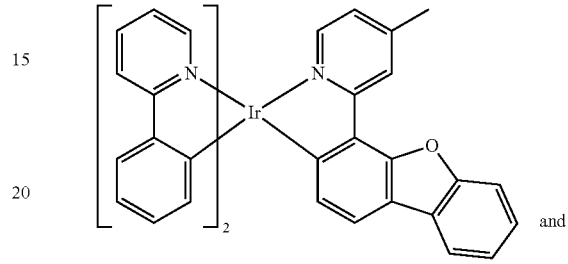

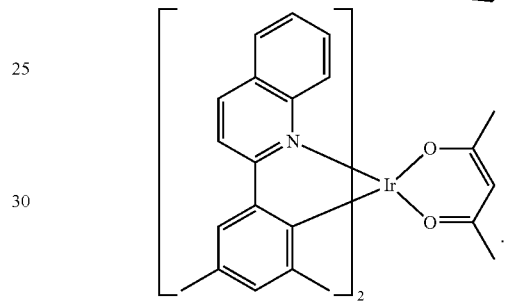

3. Thermally activated delayed fluorescent materials (TADF):

Traditional organic fluorescent materials can only emit light using 25% singlet excitonic luminescence formed by electrical excitation, and the organic electronic devices have relatively low internal quantum efficiency (up to 25%). Since the intersystem crossing is enhanced due to the strong spin-orbit coupling of the heavy atom center, the phosphorescent material can emit light using the singlet and triplet excitons formed by the electric excitation effectively, so that the internal quantum efficiency of the organic electronic device can reach 100%. However, the phosphor materials are expensive, the material stability is poor, and the device efficiency roll-off is a serious problem, which limit its application in OLED.

Thermally-activated delayed fluorescent materials are the third generation of organic light-emitting materials developed after organic fluorescent materials and organic phosphorescent materials. This type of material generally has a small singlet-triplet energy level difference (ΔEst), and triplet excitons can be converted to singlet excitons by anti-intersystem crossing to emit light. This can make full use of the singlet excitons and triplet excitons formed under electric excitation, and thus the organic electronic device can achieve 100% quantum efficiency.

The TADF material needs to have a small singlet-triplet energy level difference (ΔEst), wherein ΔEst of the TADF material <0.3 eV, further ΔEst <0.2 eV, further ΔEst <0.1 eV, and still further ΔEst <0.05 eV.

In an embodiment, the TADF material may be those disclosed in the following documents: CN103483332(A), TW201309696(A), TW201309778(A), TW201343874(A), TW201350558(A), US20120217869(A1), WO2013133359 (A1), WO2013154064(A1), Adachi, et.al. Adv. Mater., 21, 2009, 4802, Adachi, et.al. Appl. Phys. Lett., 98, 2011, 083302, Adachi, et.al. Appl. Phys. Lett, 101, 2012, 093306, Adachi, et.al. Chem. Commun., 48, 2012, 11392, Adachi, et.al. Nature Photonics, 6, 2012, 253, Adachi, et.al. Nature, 492, 2012, 234, Adachi, et.al. J. Am. Chem. Soc, 134, 2012, 14706, Adachi, et.al. Angew. Chem. Int. Ed, 51, 2012, 11311, Adachi, et.al. Chem. Commun., 48, 2012, 9580, Adachi, et.al. Chem. Commun., 48, 2013, 10385, Adachi, et.al. Adv. Mater., 25, 2013, 3319, Adachi, et.al. Adv. Mater., 25, 2013, 3707, Adachi, et.al. Chem. Mater., 25, 2013, 3038, Adachi, et.al. Chem. Mater., 25, 2013, 3766, Adachi, et.al. J. Mater. Chem. C., 1, 2013, 4599 and Adachi, et.al. J. Phys. Chem. A., 117, 2013, 5607.

Specifically, the TADF material is selected from one of the following structures:

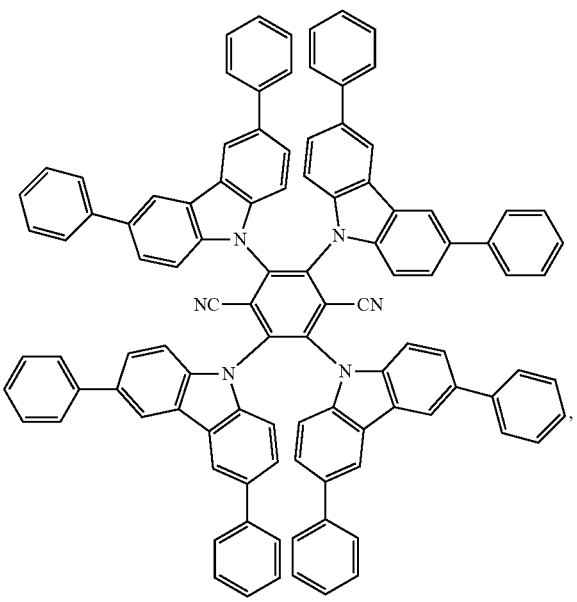

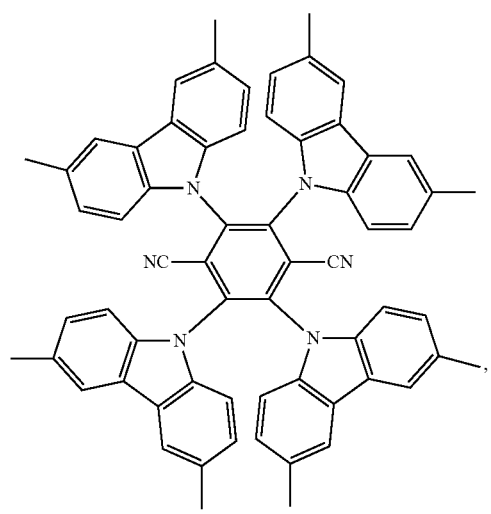

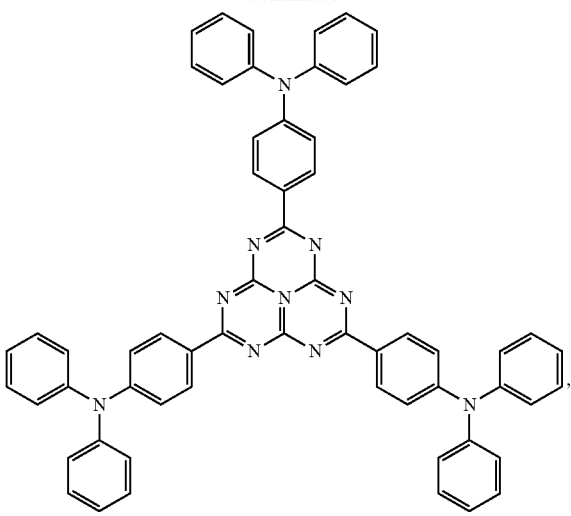

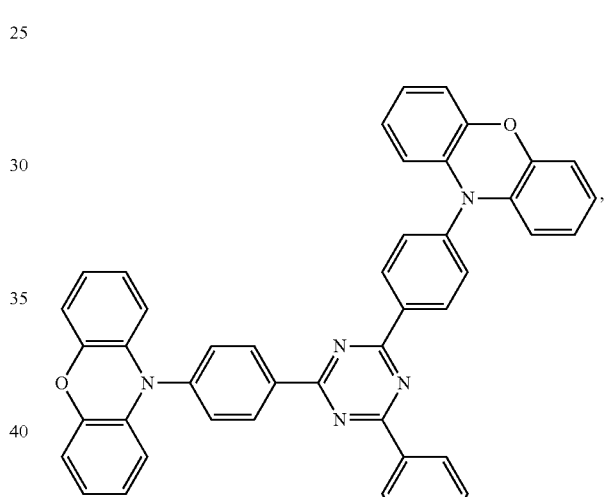

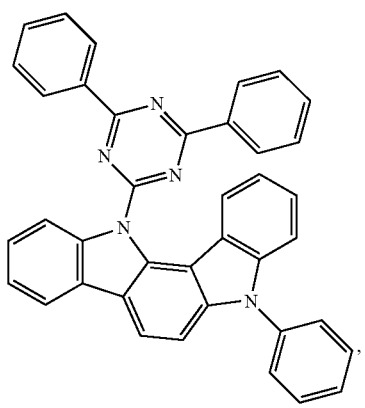

-continued
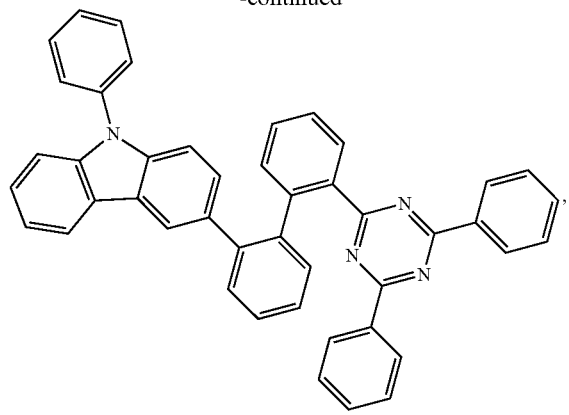
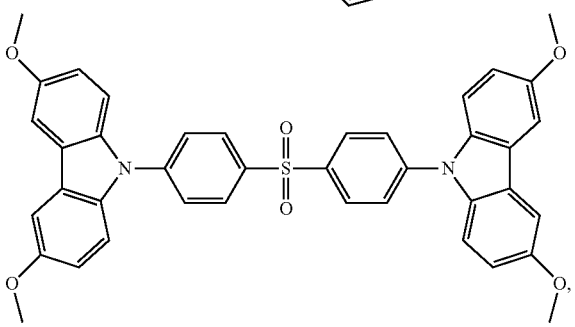
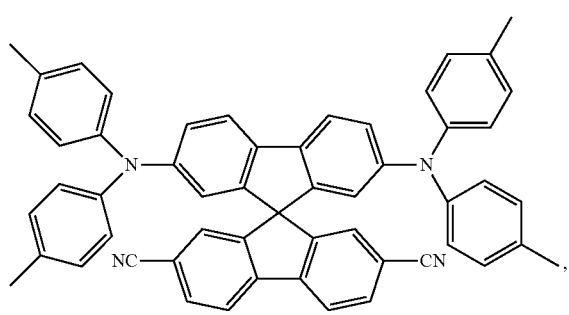
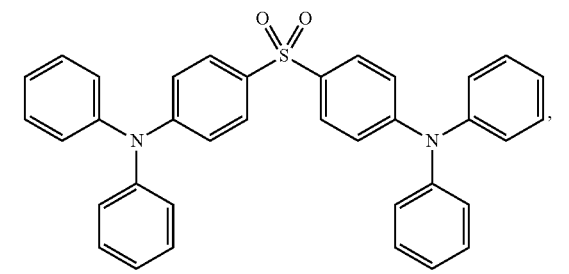
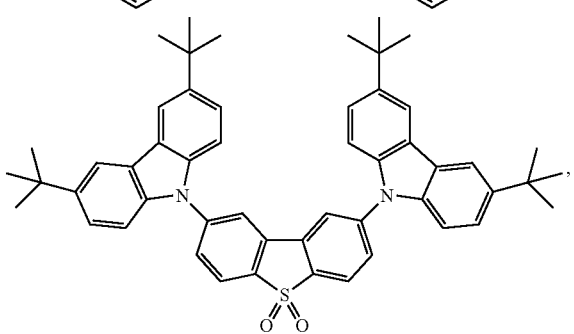
-continued
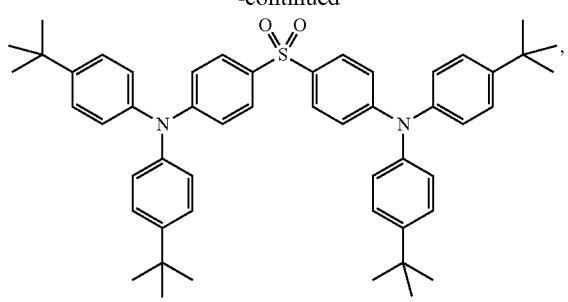
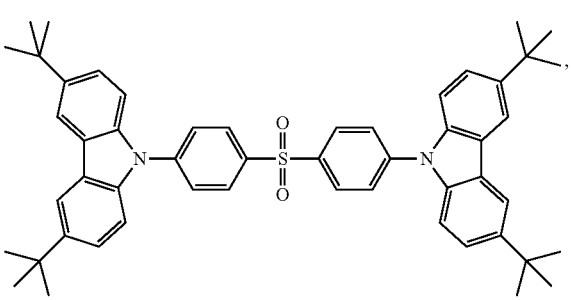
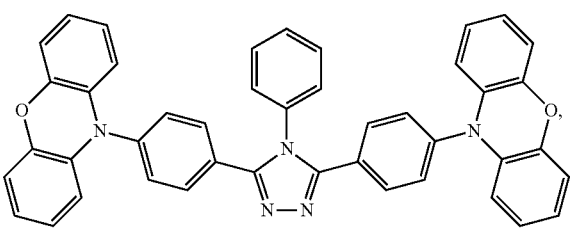
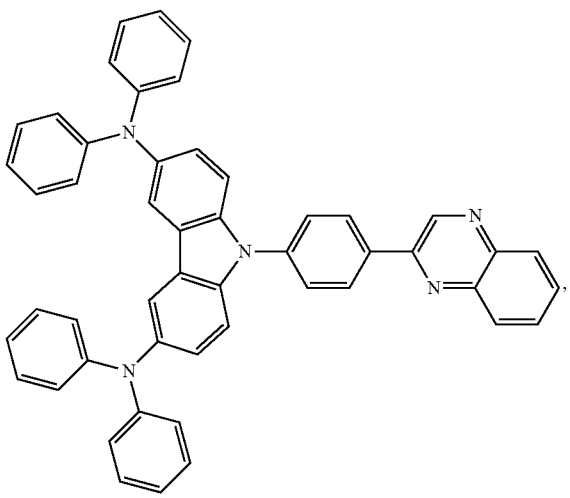
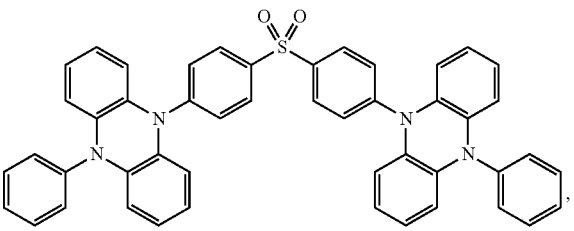

61
-continued
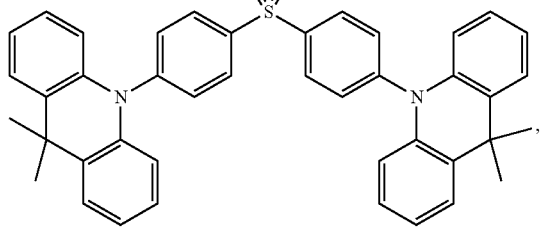
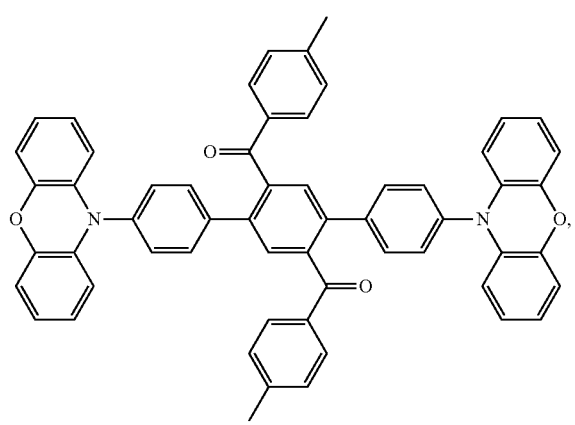
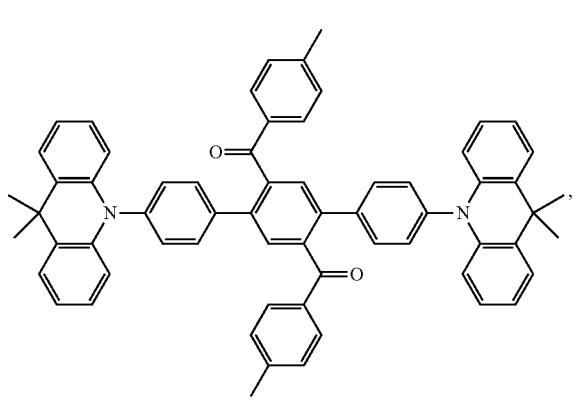
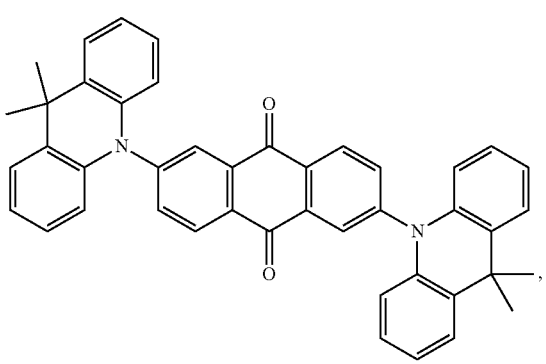
62
-continued
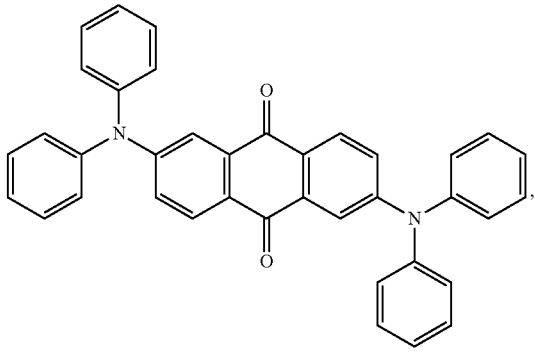
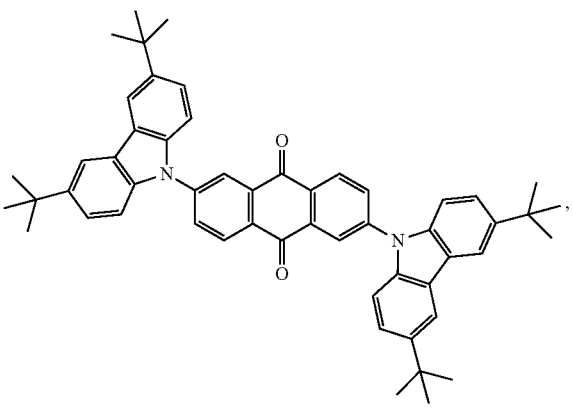
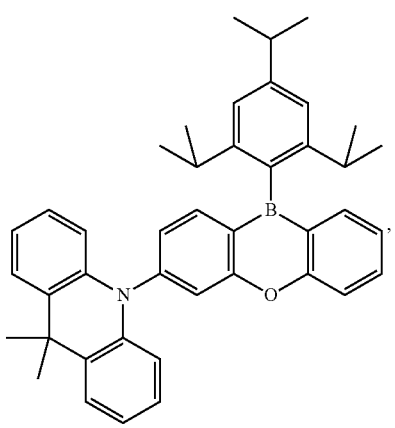
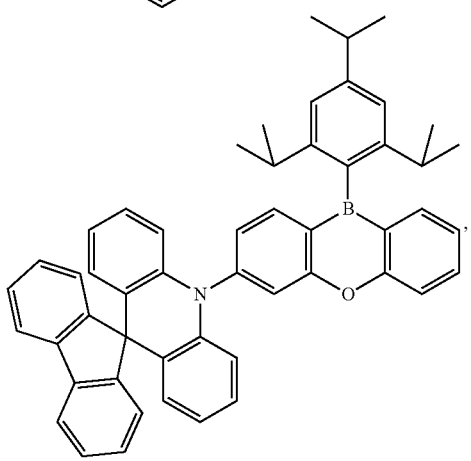

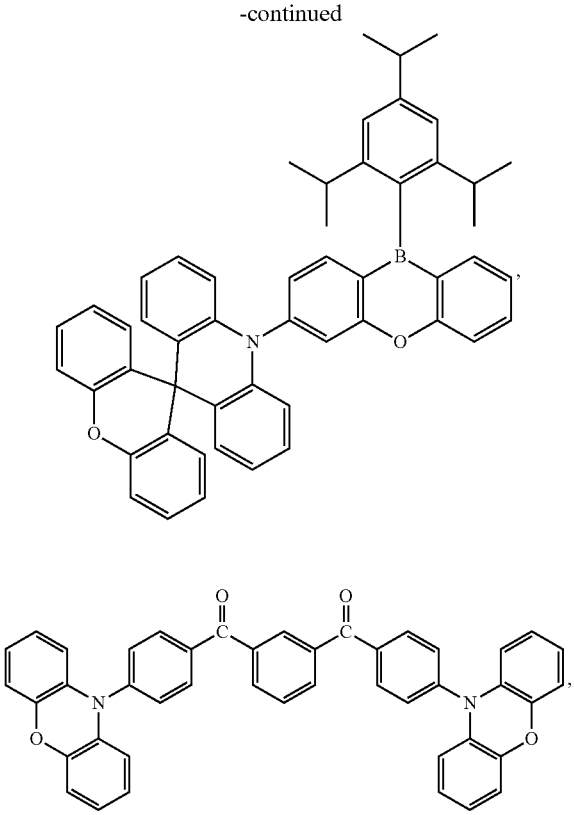
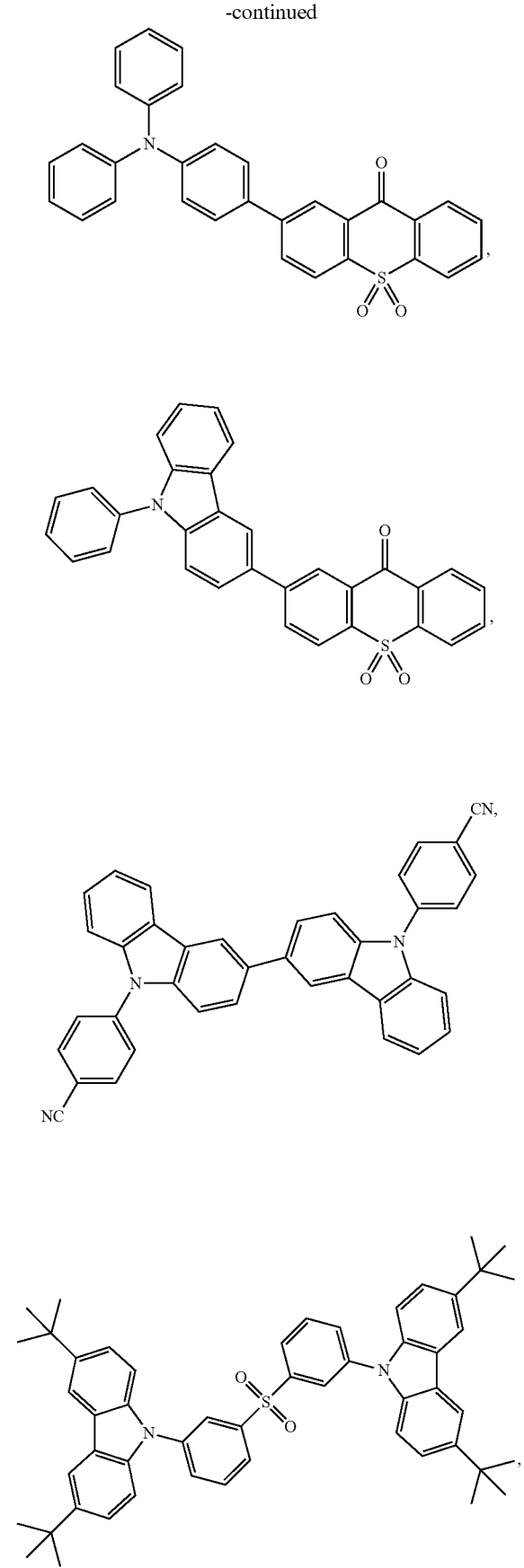

-continued

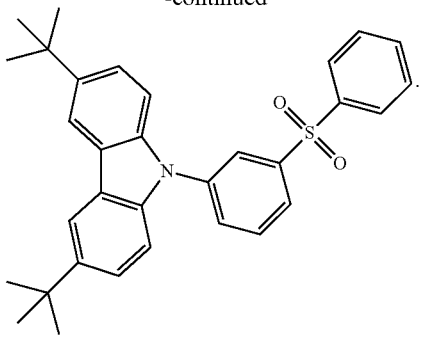

In another embodiment, the formulation comprises the above metal organic complex and an organic solvent, or comprises the above polymer and an organic solvent. In some embodiment, the formulation comprises the above metal organic complex, the above organic functional material and an organic solvent, or comprises the above polymer, the above organic functional material and an organic solvent. Wherein, the organic solvent comprises at least one of aromatic solvents and heteroaromatic solvents. In addition, the organic solvent comprises at least one of aliphatic chain substituted aromatic solvents, aliphatic ring substituted aromatic solvents, aromatic ketone solvents, and aromatic ether solvents.

Specifically, the organic solvent is selected from the solvents based on aromatics or heteroaromatics, such as p-diisopropylbenzene, pentylbenzene, tetrahydronaphthalene, cyclohexyl benzene, chloronaphthalene, 1,4-dimethylnaphthalene, 3-isopropylbiphenyl, p-cymene, dipentylbenzene, tripentylbenzene, pentyltoluene, o-xylene, m-xylene, p-xylene, o-diethylbenzene, m-diethylbenzene, p-diethylbenzene, 1,2,3,4-tetramethylbenzene, 1,2,3,5-tetramethylbenzene, 1,2,4,5-tetramethylbenzene, butylbenzene, dodecylbenzene, dihexylbenzene, dibutylbenzene, p-diisopropylbenzene, 1-methoxynaphthalene, cyclohexylbenzene, dimethylnaphthalene, 3-isopropylbiphenyl, p-cymene, 1-methylnaphthalene, 1,2,4-trichlorobenzene, 1,3-dipropoxybenzene, 4,4-difluorodiphenylmethane, 1,2-dimethoxy-4-(1-propenyl)benzene, diphenylmethane, 2-phenylpyridine, 3-phenylpyridine, N-methyldiphenylamine 4-isopropylbiphenyl, α,α-dichlorodiphenylmethane, 4-(3-phenylpropyl)pyridine, benzylbenzoate, 1,1-di(3,4-dimethylphenyl)ethane, 2-isopropylnaphthalene, dibenzylether, and the like; solvents based on ketones: 1-tetralone, 2-tetralone, 2-(phenylepoxy)tetralone, 6-(methoxyl)tetralone, acetophenone, phenylacetone, benzophenone, and derivatives thereof, such as 4-methylacetophenone, 3-methylacetophenone, 2-methylacetophenone, 4-methylphenylacetone, 3-methylphenylacetone, 2-methylphenylacetone, isophorone, 2,6,8-trimethyl-4-nonanone, fenchone, 2-nonanone, 3-nonanone, 5-nonanone, 2-demayone, 2,5-hexanedione, phorone, di-n-amyl ketone; aromatic ether solvents: 3-phenoxytoluene, butoxybenzene, benzylbutylbenzene, p-anisaldehyde dimethyl acetal, tetrahydro-2-phenoxy-2H-pyran, 1,2-dimethoxy 4-(1-propenyl)benzene, 1,4-benzodioxane, 1,3-dipropylbenzene, 2,5-dimethoxytoluene, 4-ethylphenetole, 1,2,4-trimethoxybenzene, 4-(1-propenyl)-1,2-dimethoxybenzene, 1,3-dimethoxybenzene, glycidyl phenyl ether, dibenzyl ether, 4-tert-butylanisole, trans-p-propenylanisole, 1,2-dimethoxybenzene, 1-methoxynaphthalene, diphenyl ether, 2-phenoxymethyl ether, 2-phenoxytetrahydrofuran, ethyl-2-naphthyl ether, pentyl ether, hexyl ether, dioctyl ether, ethylene glycol dibutyl ether, diethylene glycol diethyl ether, diethylene glycol butyl methyl ether, diethylene glycol dibutyl ether, triethylene glycol dimethyl ether, triethylene glycol ethyl methyl ether, triethylene glycol butyl methyl ether, tripropylene glycol dimethyl ether, tetraethylene glycol dimethyl ether; and ester solvents: alkyl octoate, alkyl sebacate, alkyl stearate, alkyl benzoate, alkyl phenylacetate, alkyl cinnamate, alkyl oxalate, alkyl maleate, alkyl lactone, alkyl oleate, and the like.

Further, the above organic solvent is aliphatic ketones, such as 2-nonanone, 3-nonanone, 5-nonanone, 2-demayone, 2,5-hexanedione, 2,6,8-trimethyl-4-demayone, phorone, di-n-pentyl ketone, and the like; or aliphatic ethers, such as amyl ether, hexyl ether, dioctyl ether, ethylene glycol dibutyl ether, diethylene glycol diethyl ether, diethylene glycol butyl methyl ether, diethylene glycol dibutyl ether, triethylene glycol dimethyl ether, triethyl ether alcohol ethyl methyl ether, triethylene glycol butyl methyl ether, tripropylene glycol dimethyl ether, tetraethylene glycol dimethyl ether, and the like.

Moreover, the above organic solvent further comprises an additional solvent. The additional solvent may be selected from at least one of the group consisting of methanol, ethanol, 2-methoxyethanol, dichloromethane, trichloromethane, chlorobenzene, o-dichlorobenzene, tetrahydrofuran, anisole, morpholine, toluene, o-xylene, m-xylene, p-xylene, 1,4-dioxane, acetone, methyl ethyl ketone, 1,2-dichloroethane, 3-phenoxy toluene, 1,1,1-trichloroethane, 1,1,2,2-tetrachloroethane, ethyl acetate, butyl acetate, dimethylformamide, dimethylacetamide, dimethyl sulfoxide, tetrahydronaphthalene, decalin and indene.

In an embodiment, the formulation is a solution or a suspension when used as a printing ink. Viscosity and surface tension are important parameters of the formulation. The suitable surface tension parameters of formulation are suitable for a specific substrate and a specific printing method.

In one embodiment, the surface tension of the formulation at operating temperature or at 25° C. is in the range of 19 dyne/cm to 50 dyne/cm, further, the surface tension of the formulation at operating temperature or at 25° C. is in the range of 22 dyne/cm to 35 dyne/cm, and still further, the surface tension of the formulation at operating temperature or at 25° C. is in the range of 25 dyne/cm to 33 dyne/cm.

In one embodiment, the solubility of the metal organic complex in toluene solution is no less than 2 mg/ml at 25° C., further, the solubility of the metal organic complex in toluene solution is no less than 3 mg/ml, further, the solubility of the metal organic complex in toluene solution is no less than 4 mg/ml, and still further, the solubility of the metal organic complex in toluene solution is no less than 5 mg/ml.

In another embodiment, when the formulation is used in inkjet printing, the viscosity of the formulation at operating temperature or at 25° C. is in the range of 1 cps to 100 cps, further in the range of 1 cps to 50 cps, further in the range of 1.5 cps to 20 cps, and still further in the range of 4.0 cps to 20 cps.

The viscosity can be adjusted by various methods, such as by selecting solvents and adjusting the concentration of functional materials in the formulation. Wherein, the viscosity of the above formulation can be appropriately adjusted according to the printing method. In the case where the above formulation comprises a metal organic complex, an organic functional material and an organic solvent, or comprises a polymer, an organic functional material and an organic solvent, the organic functional material of the formulation has a mass percentage of 0.3% to 30%, further, the organic functional material of the formulation has a mass percentage of 0.5% to 20%, still further, the organic functional material of the formulation has a mass percentage of 0.5% to 15%, still further, the organic functional material of the formulation has a mass percentage of 0.5% to 10%, and even further, the organic functional material of the formulation has a mass percentage of 1% to 5%.

Organic electronic devices can be produced by a printing or coating method when the above formulation is used as a coating or printing ink. The printing method or coating method includes, but is not limited to inkjet printing, nozzle printing, typography, screen printing, dip coating, spin coating, blade coating, roller printing, twist roller printing, lithography, flexography, rotary printing, spray coating, brush coating, transfer printing, nozzle printing, slot die coating, and the like. Particularly, the printing method or coating method is selected from one of inkjet printing, slot die coating, nozzle printing and intaglio printing.

The above formulation may further include additives which are selected from at least one of the group consisting of a surfactant compound, a lubricant, a wetting agent, a dispersant, a hydrophobic agent, a binder, to adjust the viscosity, film forming property and adhesion property of the formulation.

The detailed information relevant to the printing technology and requirements of the printing technology to the solution, such as solvents, concentration and viscosity, may be referred to Handbook of Print Media: Technologies and Production Methods, Helmut Kipphan, ISBN 3-540-67326-1.

The organic electronic device according to one embodiment comprises one of the above metal organic complex, the above polymer and the above formulation.

The organic electronic devices may be selected from, but not limited to, one of an organic light-emitting diode (OLED), an organic photovoltaic cell (OPV), an organic light-emitting electrochemical cell (OLEEC), an organic field effect transistor (OFET), an organic light-emitting field effect transistor, an organic laser, an organic spintronic device, organic sensor and an organic plasmon emitting diode. Further, the organic electronic device is an OLED. Specifically, the above metal organic complex is used in the light-emitting layer of an OLED device.

In an embodiment, the organic electronic device comprises a functional layer. The material of the functional layer comprises one of the above metal organic complex and the above polymer.

In some embodiment, the organic electronic device comprises a substrate, an anode, a light-emitting layer and a cathode. The substrate can be opaque or transparent. The transparent substrate can be used to make a transparent light-emitting device. The substrate may be that disclosed in Bulovic et al. Nature 1996, 380, p29 and Gu et al. Appl. Phys. Lett. 1996, 68, p2606. The substrate may be rigid or elastic. Further, the substrate is selected from one of plastic, metal, semiconductor wafer and glass. Specifically, the substrate has a smooth surface. More specifically, the surface of the substrate is free from defects.

In an embodiment, the substrate is flexible and is a polymer film or a plastic. Wherein, the glass transition temperature $T_g$ of the substrate is 150° C. or more, further, the glass transition temperature $T_g$ of the substrate is 200° C. or more, still further, the glass transition temperature $T_g$ of the substrate is 250° C. or more, and even further, the glass transition temperature $T_g$ of the substrate is 300° C. or more. Specifically, the flexible substrate is polyethylene terephthalate (PET) and polyethylene 2,6-naphthalate (PEN).

The anode includes one of a conductive metal, a metallic oxide and a conductive polymer.

The anode can inject holes easily into the hole injection layer (HIL), the hole transport layer (HTL), or the light-emitting layer. In an embodiment, the absolute value of the difference between the work function of the anode and the HOMO energy level of the emitter in the light-emitting layer, or the difference between the work function of the anode and the HOMO energy level or the valence band energy level of the p-type semiconductor material as the HIL or HTL or the electron blocking layer (EBL) is smaller than 0.5 eV, further smaller than 0.3 eV, and still further smaller than 0.2 eV.

The anode material includes, but not limited to, Al, Cu, Au, Ag, Mg, Fe, Co, Ni, Mn, Pd, Pt, ITO, aluminum doped zinc oxide (AZO), and the like. The anode material may be deposited by suitable technologies, such as the physical vapor deposition method which includes a radio frequency magnetron sputtering, a vacuum thermal evaporation, an electron beam, and the like.

Wherein, the anode is patterned and structured. A patterned ITO conductive substrate may be purchased from market to prepare the organic electronic device.

The cathode can inject electrons easily into the electron injection layer (EIL) or the electron transport layer (ETL), or directly injected into the light-emitting layer. In an embodiment, the absolute value of the difference between the work function of the cathode and the LUMO energy level of the emitter in the light-emitting layer, or the difference between the work function of the cathode and the LUMO energy level or the valence band energy level of the n-type semiconductor material as the electron injection layer (EIL) or the electron transport layer (ETL) or the hole blocking layer (HBL) is smaller than 0.5 eV.

Further, the absolute value of the difference between the work function of the cathode and the LUMO energy level of the emitter in the light-emitting layer, or the difference between the work function of the cathode and the LUMO energy level or the valence band energy level of the n-type semiconductor material as the electron injection layer (EIL) or the electron transport layer (ETL) or the hole blocking layer (HBL) is smaller than 0.3 eV. Still further, the absolute value of the difference between the work function of the cathode and the LUMO energy level of the emitter in the light-emitting layer, or the difference between the work function of the cathode and the LUMO energy level or the valence band energy level of the n-type semiconductor material as the electron injection layer (EIL) or the electron transport layer (ETL) or the hole blocking layer (HBL) is smaller than 0.2 eV.

In general, all materials may be used as the cathode of the OLED may be used as the cathode material of the organic electronic device. The cathode material is selected from, but not limited to, one of Al, Au, Ag, Ca, Ba, Mg, LiF/Al, Mg/Ag alloy, BaF2/Al, Cu, Fe, Co, Ni, Mn, Pd, Pt and ITO. The cathode material may be deposited by the physical vapor deposition method which includes a radio frequency magnetron sputtering, a vacuum thermal evaporation, an electron beam, and the like.

The OLED may also comprise other functional layers including a hole injection layer (HIL), a hole transport layer (HTL), an electron blocking layer (EBL), an electron injection layer (EIL), an electron transport layer (ETL), a hole blocking layer (HBL), and the like.

The light-emitting layer comprises the above metal organic complex or polymer, further, the light-emitting layer is prepared by a solution processing method.

The emission wavelength of the above light-emitting device is between 300 and 1000 nm, further between 350 and 900 nm, and even further between 400 and 800 nm.

The above organic electronic device may be applied in various electronic equipment including display equipments, lighting equipments, light sources, sensors, and the like.

DETAILED EXAMPLES

Example 1: Synthesis of Compound Ir-1

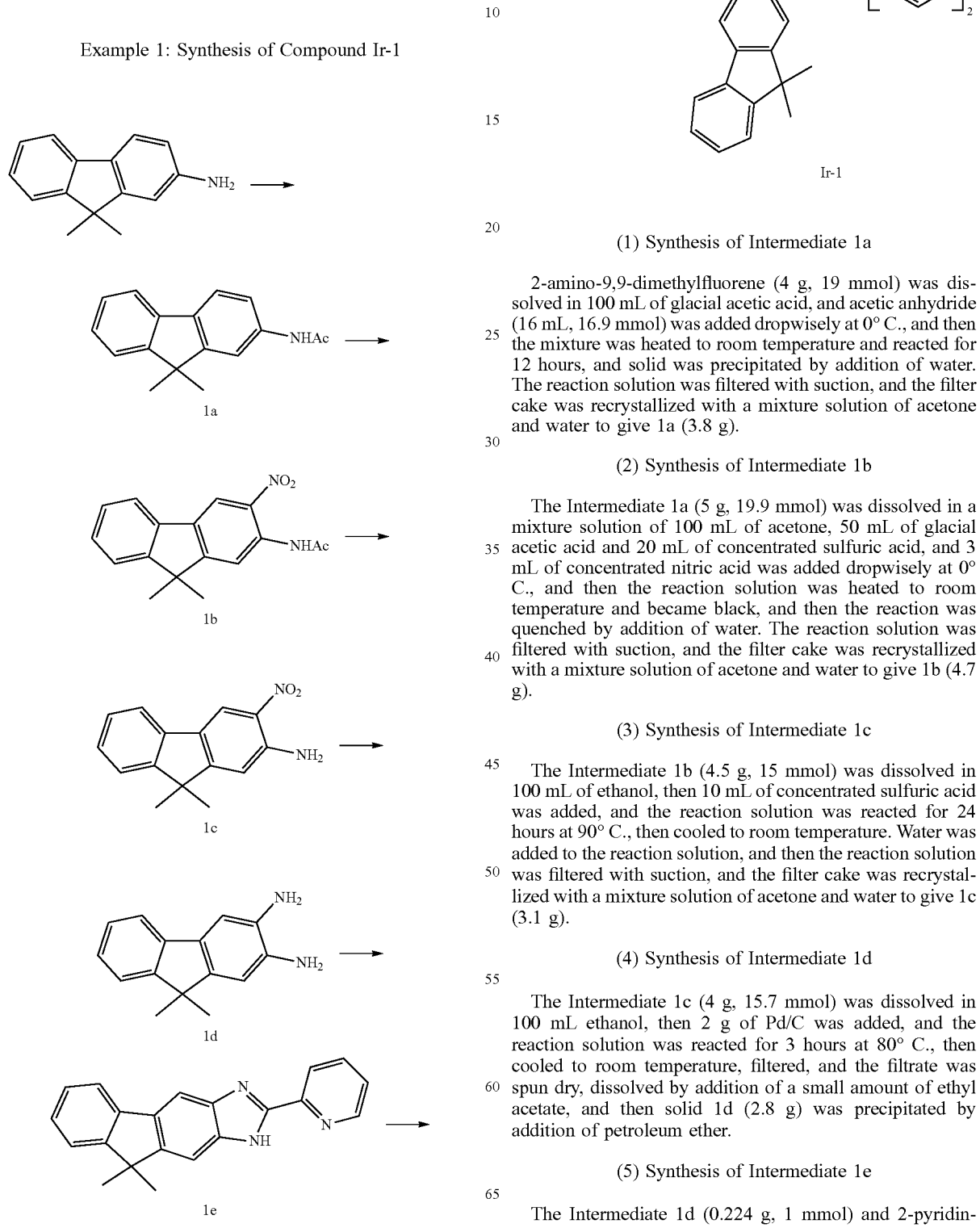

(1) Synthesis of Intermediate 1a 2-amino-9,9-dimethylfluorene (4 g, 19 mmol) was dissolved in 100 mL of glacial acetic acid, and acetic anhydride (16 mL, 16.9 mmol) was added dropwisely at 0° C., and then the mixture was heated to room temperature and reacted for 12 hours, and solid was precipitated by addition of water. The reaction solution was filtered with suction, and the filter cake was recrystallized with a mixture solution of acetone and water to give 1a (3.8 g).

(2) Synthesis of Intermediate 1b

The Intermediate 1a (5 g, 19.9 mmol) was dissolved in a mixture solution of 100 mL of acetone, 50 mL of glacial acetic acid and 20 mL of concentrated sulfuric acid, and 3 mL of concentrated nitric acid was added dropwisely at 0° C., and then the reaction solution was heated to room temperature and became black, and then the reaction was quenched by addition of water. The reaction solution was filtered with suction, and the filter cake was recrystallized with a mixture solution of acetone and water to give 1b (4.7 g).

(3) Synthesis of Intermediate 1c

The Intermediate 1b (4.5 g, 15 mmol) was dissolved in 100 mL of ethanol, then 10 mL of concentrated sulfuric acid was added, and the reaction solution was reacted for 24 hours at 90° C., then cooled to room temperature. Water was added to the reaction solution, and then the reaction solution was filtered with suction, and the filter cake was recrystallized with a mixture solution of acetone and water to give 1c (3.1 g).

(4) Synthesis of Intermediate 1d

The Intermediate 1c (4 g, 15.7 mmol) was dissolved in 100 mL ethanol, then 2 g of Pd/C was added, and the reaction solution was reacted for 3 hours at 80° C., then cooled to room temperature, filtered, and the filtrate was spun dry, dissolved by addition of a small amount of ethyl acetate, and then solid 1d (2.8 g) was precipitated by addition of petroleum ether.

(5) Synthesis of Intermediate 1e

The Intermediate 1d (0.224 g, 1 mmol) and 2-pyridinecarboxaldehyde (0.107 g, 1 mmol) were dissolved in 20 mL of methanol, then 2 mL of phosphoric acid was added, and the reaction solution was reacted for 3 hours at 60° C., concentrated, water was added, and then the reaction solution was extracted with ethyl acetate, and finally solid 1e (0.248 g) was obtained by column chromatography with ethyl acetate:petroleum ether:ethanol=10:2:1. (6) Synthesis of Compound Ir-1

The Intermediate 1e (0.6 g, 1.9 mmol) and 2-phenylpyridinium chloride bridge (1.14 g, 0.95 mmol) were placed in a dry two-necked flask. Then the two-necked flask was evacuated and filled with nitrogen which was repeated three times, followed by the addition of 5 mL of dichloromethane and 5 mL of methanol. The reaction solution was stirred at room temperature overnight, concentrated, and finally Ir-1 (0.46 g) was obtained by column chromatography with methylene chloride/petroleum ether=1:10.

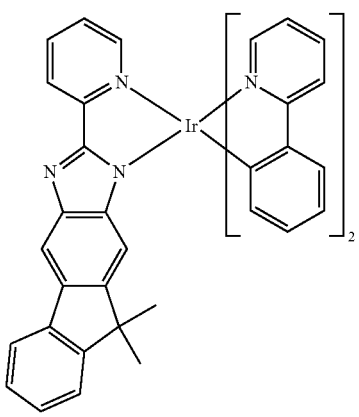

Ir-1

Example 2: Synthesis of Compound Cu-1

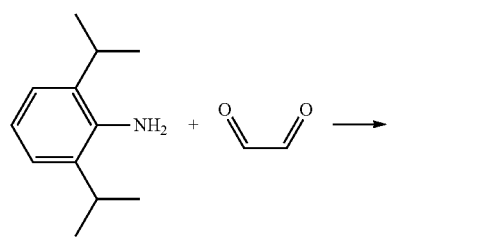

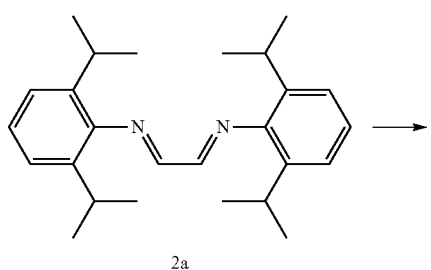

2a

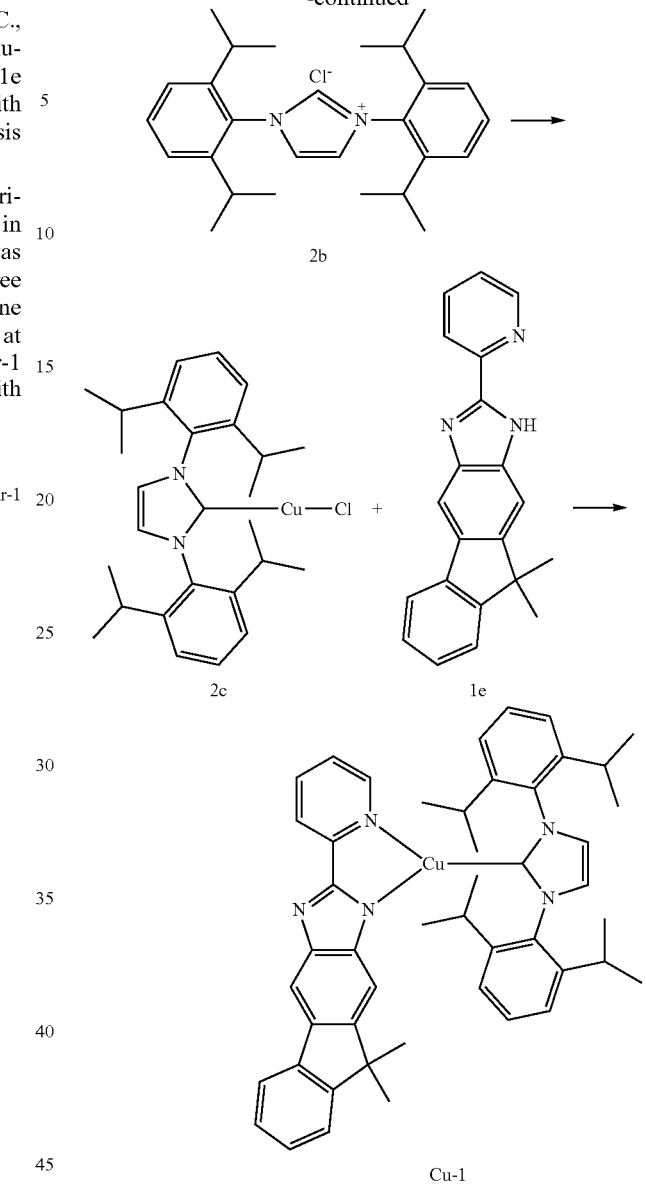

(1) Synthesis of Intermediate 2a 2,6-diisopropylamine (19.7 g, 111 mmol) and glacial acetic acid (1 mL) were dissolved in 50 mL of toluene, stirred at room temperature, and then 50 mL of the methanol solution of glyoxal (5.1 g, 88 mmol) was slowly added dropwisely, and the reaction solution was reacted for 6 hours, then filtered with suction, and the filter cake was washed with methanol and dried in vacuum to give solid 2a (16.6 g).

(2) Synthesis of Intermediate 2b

The Intermediate 2a (4 g, 10.6 mmol) and paraformaldehyde (0.4 g) were dissolved in 80 mL of ethyl acetate, stirred at room temperature for 10 min, then 4 mL of the ethyl acetate solution of trimethylchlorosilane (2 mL) was added dropwisely. After that, the reaction solution was stirred for 2 hours, then cooled to 0° C., filtered with suction, and the filter cake was recrystallized with a mixture solution of methylene chloride and ethyl acetate to give solid 2b (3.5 g).

(3) Synthesis of Intermediate 2c

The Intermediate 2b (0.42 g, 1 mmol), cuprous chloride (0.098 g, 1 mmol) and potassium carbonate (0.28 g, 2 mmol) were placed in a dry reaction flask, then 15 mL of acetone was added, and the reaction solution was reacted under stirring for 24 hours at 60° C., then cooled to room temperature, filtered, and the filtrate was concentrated and recrystallized with n-pentane to give 2c (0.43 g).

(4) Synthesis of Compound Cu-1

Sodium hydride (16 mg, 0.4 mmol, 60% mineral oil) was placed in a dry two-necked flask under nitrogen atmosphere, and 10 mL of dry THF was added. The mixture was stirred at room temperature for 30 minutes, then 10 mL of the tetrahydrofuran solution of 1e (124.6 mg, 0.4 mmol) was added, and the reaction solution was stirred for 1 hour at room temperature, then 2c (195 mg, 0.4 mmol) was added, the reaction solution was further stirred for 3 hours, then filtered, concentrated, and then recrystallized with a mixture solution of methylene chloride and ethyl ether to give solid Cu-1 (0.12 g).

Cu-1

Example 3: Synthesis of Compound Cu-2

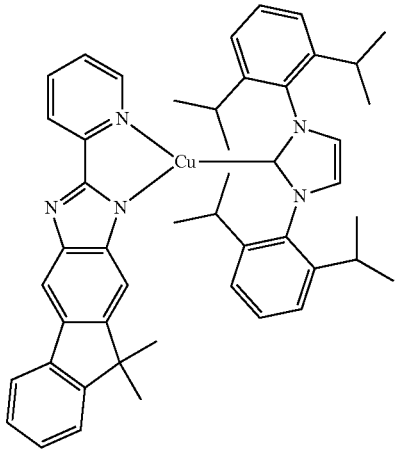

-continued

3a

+

2c

Cu-2

(1) Synthesis of Intermediate 3a

Phenanthrenedione (2.08 g, 10 mmol), pyridine-2-carboxaldehyde (1.07 g, 10 mmol) and ammonium acetate (7.7 g, 100 mmol) were placed in a dry flask, then 2 mL of glacial acetic acid was added, refluxed for 3 h, cooled to room temperature, and aqueous ammonia was added dropwisely, precipitate was precipitated and then recrystallized with ethanol to give solid 3a (1.47 g).

(2) Synthesis of Compound Cu-2

Sodium hydride (16 mg, 0.4 mmol, 60% mineral oil) was placed in a dry two-necked flask under nitrogen atmosphere, and 10 mL of dry THF was added. The reaction solution was stirred at room temperature for 30 minutes, then 10 mL of the tetrahydrofuran solution of 3a (118 mg, 0.4 mmol) was added, and the reaction solution was stirred for 1 hour at room temperature, then 2c (195 mg, 0.4 mmol) was added, the reaction solution was further stirred for 3 hours, then filtered, concentrated, and then recrystallized with a mixture solution of methylene chloride and ethyl ether to give solid Cu-2 (0.1 g).

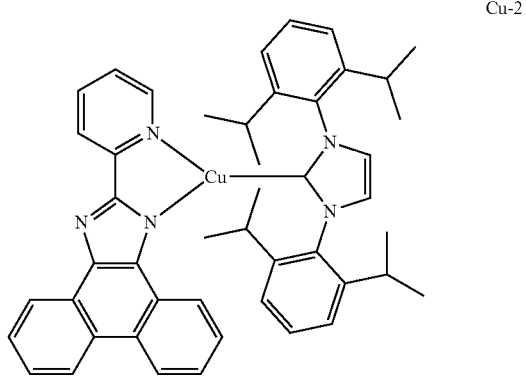

Cu-2

Test:

The energy levels of the metal organic complexes Ir-1, Cu-1 and Cu-2 obtained in Examples 1 to 3 are calculated by quantum calculations, such as using TD-DFT (Time Dependent-Density Functional Theory) by Gaussian03W (Gaussian Inc.), and the specific simulation methods can be found in WO2011141110. Firstly, the molecular geometry is optimized by semi-empirical method "Ground State/Hartree-Fock/Default Spin/LanL2 MB" (Charge 0/Spin Singlet), and then the energy structure of organic molecules is calculated by TD-DFT (time-density functional theory) "TD-SCF/DFT/Default Spin/B3PW91/gen geom=connectivity pseudo=lanl2" (Charge 0/Spin Singlet). The HOMO and LUMO levels are calculated according to the following calibration formulas, S 1 and Ti are used directly.

HOMO(eV)=((HOMO(Gaussian)×27.212)−0.9899)/1.1206

LUMO(eV)=((LUMO(Gaussian)×27.212)−2.0041)/1.385 wherein HOMO(G) and LUMO(G) in the unit of Hartree are the direct calculation results of Gaussian 03W. The results were shown in Table 1.

TABLE 1

| Materials | HOMO [eV] | LUMO [eV] | $T_1$ [eV] | S1 [eV] |
|---|---|---|---|---|
| Ir-1 | −5.11 | −2.67 | 2.28 | 2.49 |
| Cu-1 | −4.93 | −2.16 | 2.61 | 3.06 |
| Cu-2 | −4.88 | −2.15 | 2.50 | 3.07 |

OLED devices were prepared by using the metal organic complexes obtained in Examples 1 to 3, respectively. The specific steps are as follows:

a. Cleaning of conductive glass substrate: in first use, the conductive glass substrate may be cleaned with various solvents such as chloroform, acetone or isopropanol, and then treated with ultraviolet and ozone;

b. HIL (60 nm), EML (45 nm) and ETL (35 nm) were formed by thermal evaporation in high vacuum ($1\times10^{-6}$ mbar).

c. Cathode: LiF/Al (1 nm/150 nm) was formed by thermal evaporation in high vacuum ($1\times10^{-6}$ mbar);

d. Encapsulating: the device was encapsulated with UV-curable resin in a nitrogen glove box.

OLED devices prepared by using the metal organic complexes obtained in Examples 1 to 3 have the following structures, respectively:

(1)OLED-1: ITO/NPD(60 nm)/15% Ir-1: mCP(45 nm)/TPBi(35 nm)/LiF(1 nm)/Al(150 nm)/Cathode;

(2)OLED-2:ITO/NPD(60 nm)/15% Cu-1: mCP(45 nm)/TPBi(35 nm)/LiF(1 nm)/Al(150 nm)/C athode;

(3)OLED-3:ITO/NPD(60 nm)/15% Cu-2: mCP(45 nm)/TPBi(35 nm)/LiF(1 nm)/Al(150 nm)/C athode;

Test:

The current-voltage-luminance (J-V-L) characteristics of each OLED device are characterized by evaporation or spin-on equipment while important parameters such as efficiency and external quantum efficiency were recorded.

As detected, the maximum external quantum efficiencies of OLED-1, OLED-2 and OELD-3 were 15.1%, 10.2% and 8.4%, respectively.

The structure of the device may be further optimized, for example, the combination of HTM, ETM and host material can further improve the properties of the device, especially efficiency, driving voltage and lifetime.

It should be understood that, the application of the present disclosure is not limited to the above-described examples, and those skilled in the art can make modifications and changes in accordance with the above description, all of which are within the scope of the appended claims.

The invention claimed is:

1. An metal organic complex which has the following general formula:

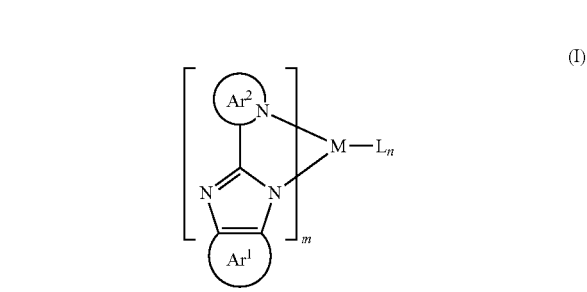

(I)

wherein, $Ar^2$ is selected from one of the following groups:

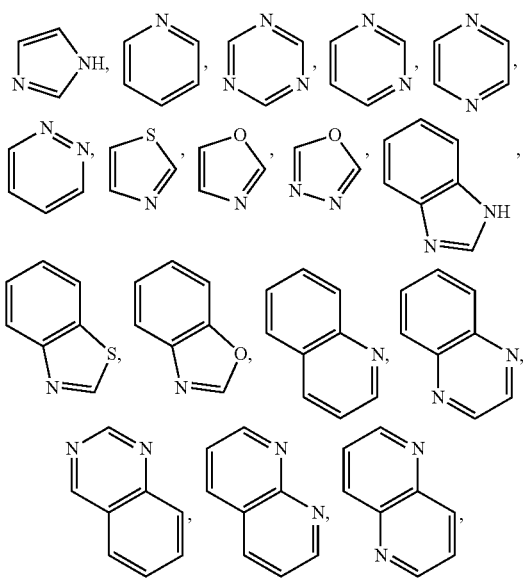

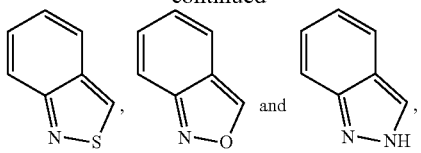

wherein, H in the groups may be further substituted;

Ar¹ is selected from one of the following general formulas:

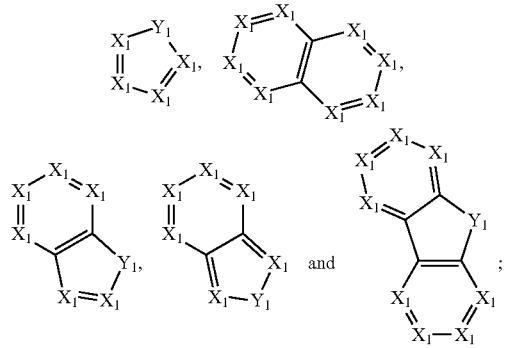

a plurality of $X_1$ are each independently selected from $CR^4$ or N;

$Y_1$ is selected from $CR^4R^5$, $SiR^4R^5$, $NR^4$, $C(=O)$, S or O;

$R^4$ and $R^5$ are each independently selected from at least one of the group consisting of H, D, linear alkyl containing 1 to 20 C atoms, alkoxy containing 1 to 20 C atoms, thioalkoxy containing 1 to 20 C atoms, branched alkyl containing 3 to 20 C atoms, cyclic alkyl containing 3 to 20 C atoms, silyl containing 3 to 20 C atoms, substituted keto containing 1 to 20 C atoms, alkoxycarbonyl containing 2 to 20 C atoms, aryloxycarbonyl containing 7 to 20 C atoms, cyano, carbamoyl, halocarbonyl, formyl, isocyano, isocyanate group, thiocyanate group, isothiocyanate group, hydroxyl, nitryl, $CF_3$ group, Cl, Br, F, crosslinkable group, aromatic cyclic group containing 5 to 40 C atoms, heteroaromatic cyclic group containing 5 to 40 C atoms, aryloxy containing 5 to 40 C atoms and heteroaryloxy containing 5 to 40 C atoms;

wherein, $R^4$ and $R^5$ may form aliphatic or aromatic cyclic groups by bonding with each other, and $R^4$ and $R^5$ may also form aliphatic or aromatic cyclic groups by bonding with themselves, respectively;

M is a transitional metal element, wherein the M is selected from iridium or copper;

L is selected from one of the group consisting of a monodentate neutral ligand, a monodentate anionic ligand, a bidentate neutral ligand and a bidentate anionic ligand;

m is any integer from 1 to 3; and n is any integer from 0 to 2;

wherein the general formula of the ligand L0 of the metal organic complex is as follows, and the number of C atoms of the substructure Lb of the ligand L0 does not exceed 30:

L0

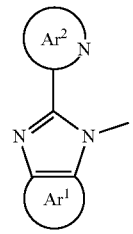

Lb

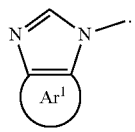

2. The metal organic complex according to claim 1, wherein the general formula of the metal organic complex is selected from the group consisting of:

(I-1)

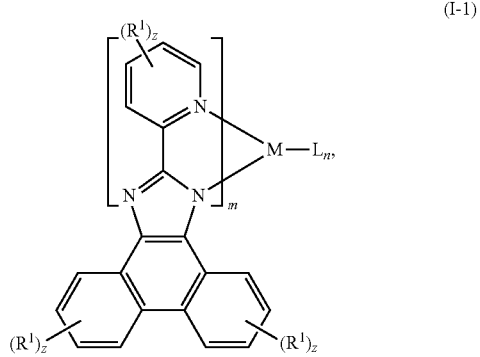

(I-2)

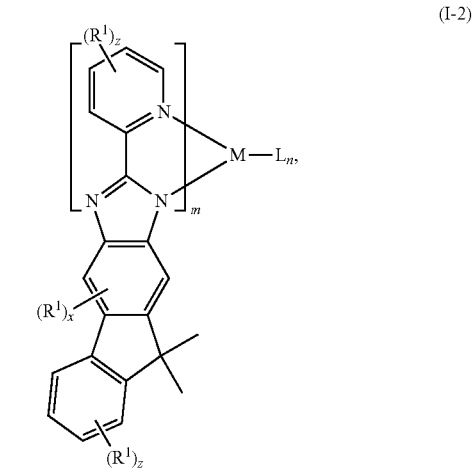

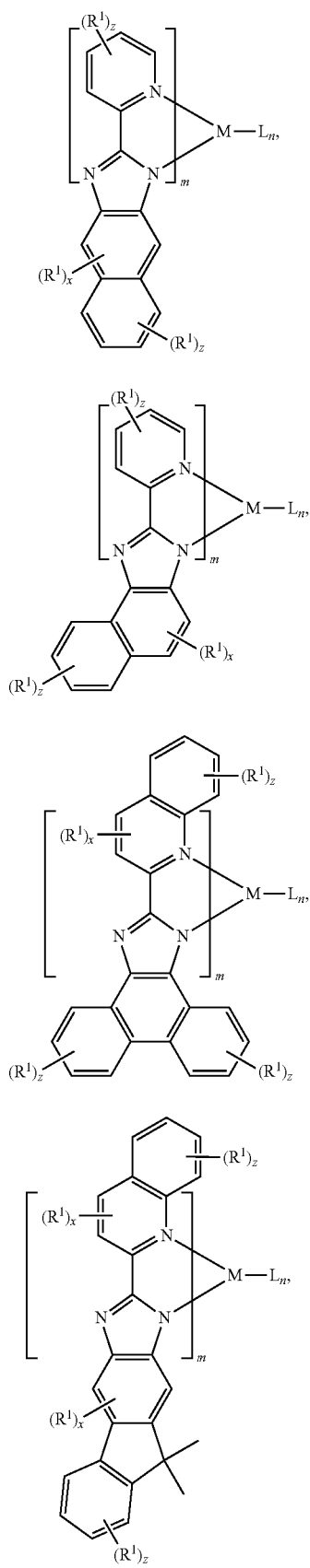
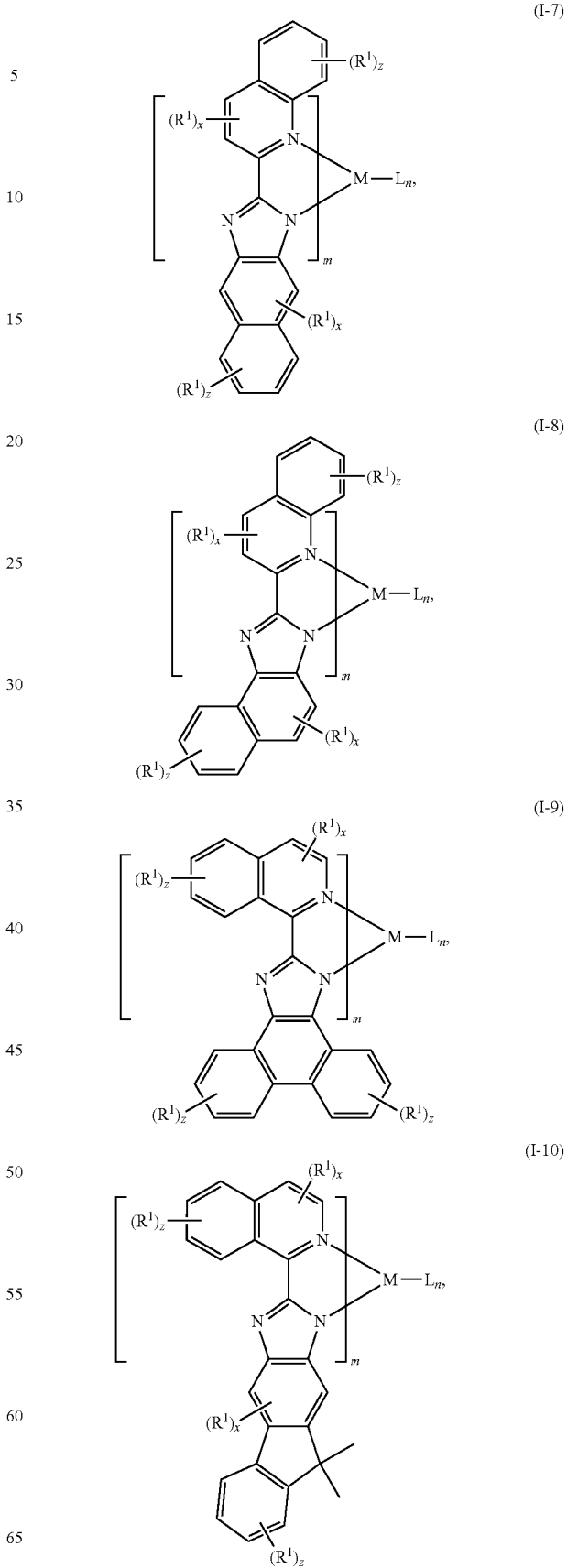

(I-11) 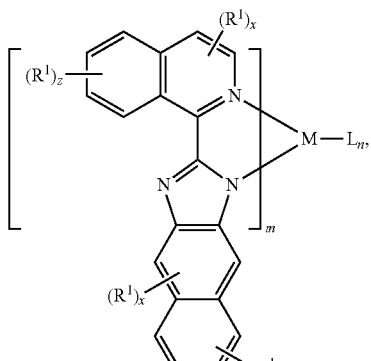

(I-12) 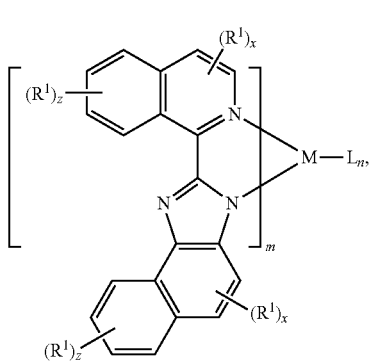

(I-13) 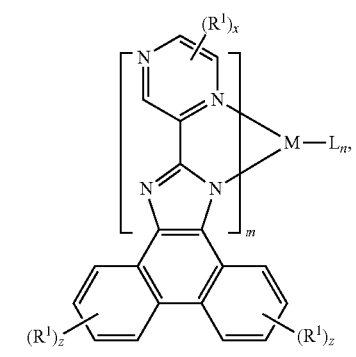

(I-14) 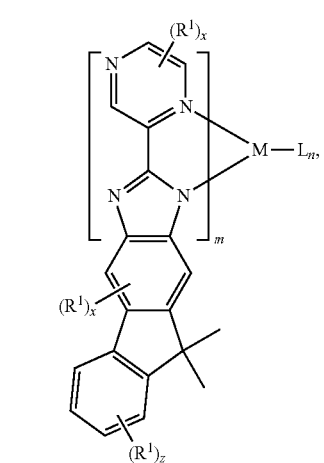

(I-15) 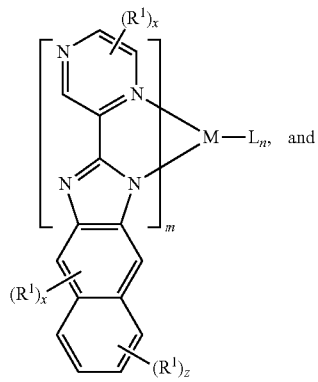

(I-16) 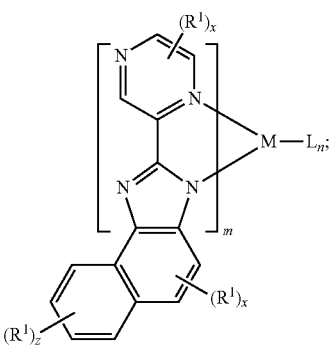

wherein, $R^1$ is selected from one of the group consisting of H, F, Cl, Br, I, D, CN, $NO_2$, $CF_3$, $B(OR^2)_2$, $Si(R^2)_3$, linear alkyl, $R^2$-substituted linear alkyl, alkyl ether group, $R^2$-substituted alkyl ether group, alkyl thioether group, $R^2$-substituted alkyl thioether group, branched alkyl, $R^2$-substituted branched alkyl, cyclic alkyl, and $R^2$-substituted cyclic alkyl;

$R^2$ is selected from one of the group consisting of H, D, aliphatic alkyl, aromatic group, aromatic cyclic group and heteroaromatic group;

x is any integer from 0 to 2, y is any integer from 0 to 3, and z is any integer from 0 to 4.

3. The metal organic complex according to claim 1, wherein $Ar^1$ is selected from one of the following groups:

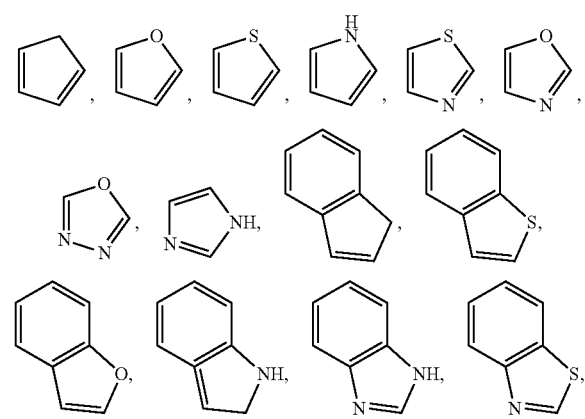

-continued

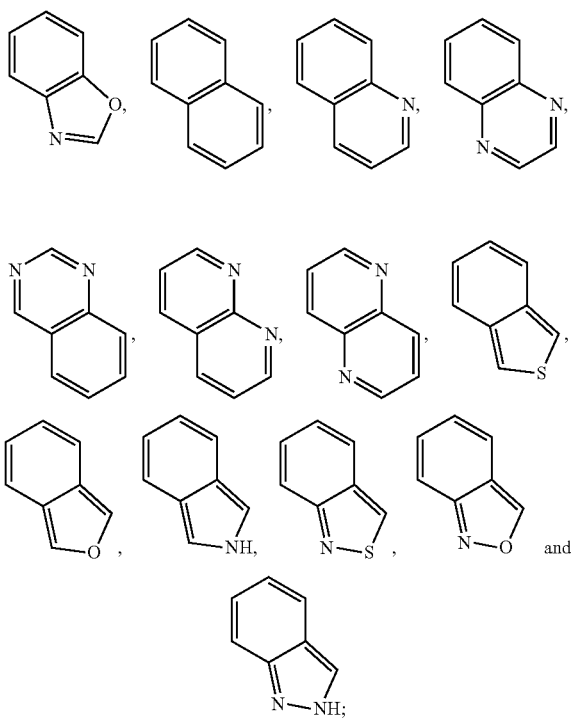

wherein, H in the groups may be further substituted.

4. An metal organic complex which has the following general formula:

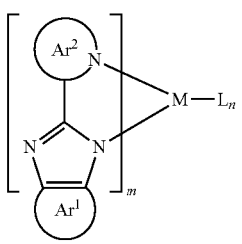

(I)

wherein, Ar² is selected from one of the following groups:

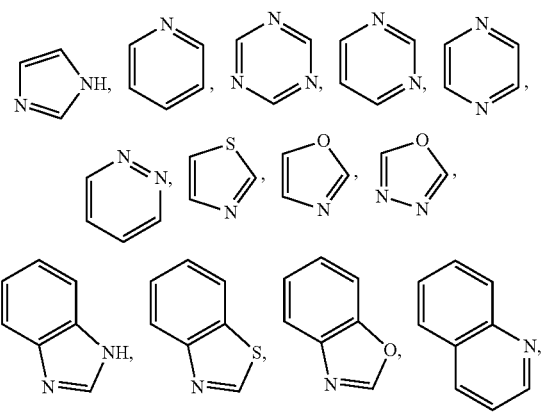

-continued

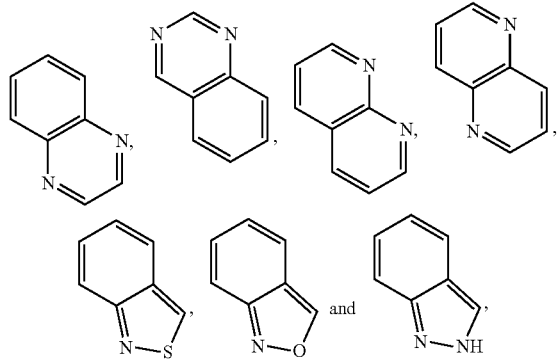

wherein, H in the groups may be further substituted;
Ar¹ is selected from one of the following general formulas:

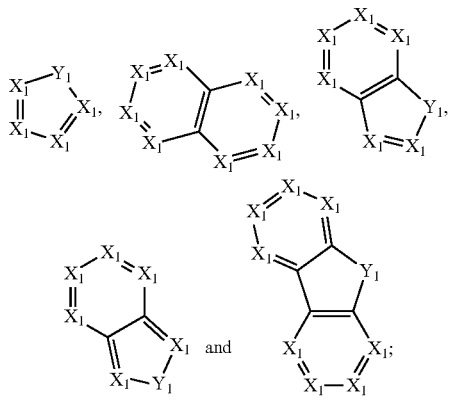

a plurality of $X_1$ are each independently selected from $CR^4$ or N;
$Y_1$ is selected from $CR^4R^5$, $SiR^4R^5$, $NR^4$, C(=O), S or O;
$R^4$ and $R^5$ are each independently selected from at least one of the group consisting of H, D, linear alkyl containing 1 to 20 C atoms, alkoxy containing 1 to 20 C atoms, thioalkoxy containing 1 to 20 C atoms, branched alkyl containing 3 to 20 C atoms, cyclic alkyl containing 3 to 20 C atoms, silyl containing 3 to 20 C atoms, substituted keto containing 1 to 20 C atoms, alkoxycarbonyl containing 2 to 20 C atoms, aryloxycarbonyl containing 7 to 20 C atoms, cyano, carbamoyl, halocarbonyl, formyl, isocyano, isocyanate group, thiocyanate group, isothiocyanate group, hydroxyl, nitryl, $CF_3$ group, Cl, Br, F, crosslinkable group, aromatic cyclic group containing 5 to 40 C atoms, heteroaromatic cyclic group containing 5 to 40 C atoms, aryloxy containing 5 to 40 C atoms and heteroaryloxy containing 5 to 40 C atoms;
wherein, $R^4$ and $R^5$ may form aliphatic or aromatic cyclic groups by bonding with each other, and $R^4$ and $R^5$ may also form aliphatic or aromatic cyclic groups by bonding with themselves, respectively;
M is a transitional metal element;
L is selected from one of the group consisting of a monodentate neutral ligand, a monodentate anionic ligand, a bidentate neutral ligand and a bidentate anionic ligand;
m is any integer from 1 to 3; and n is any integer from 0 to 2;

wherein the general formula of the ligand L0 of the metal organic complex is as follows, and the number of C atoms of the substructure Lb of the ligand L0 does not exceed 30, wherein the ligand L0 has a triplet energy level $T_1 \geq 2.0$ eV:

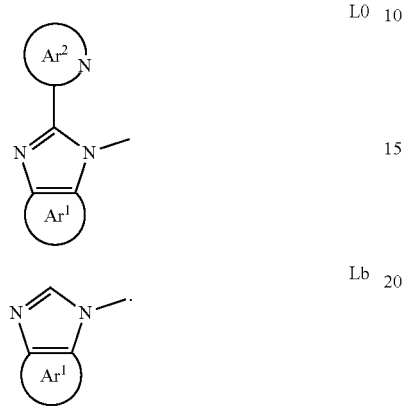

5. The metal organic complex according to claim 1, wherein the M is selected from one of the group consisting of chromium, molybdenum, tungsten, ruthenium, rhodium, nickel, silver, copper, zinc, palladium, gold, osmium, rhenium, iridium and platinum.

6. The metal organic complex according to claim 1, wherein the L is selected from one of the general formulas

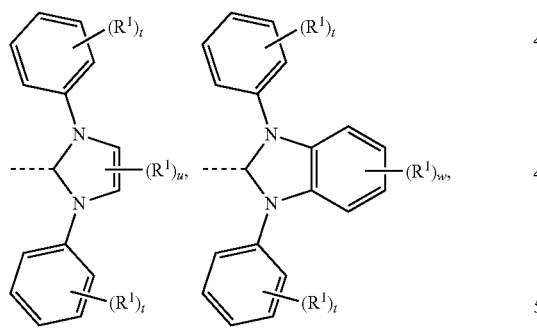

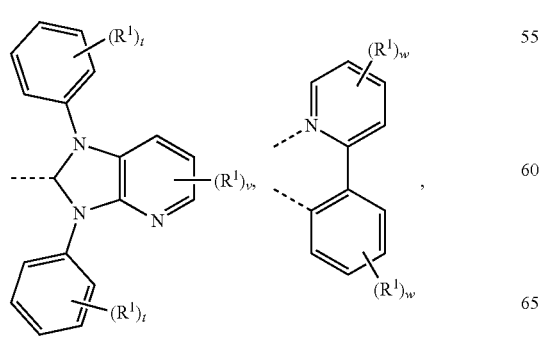

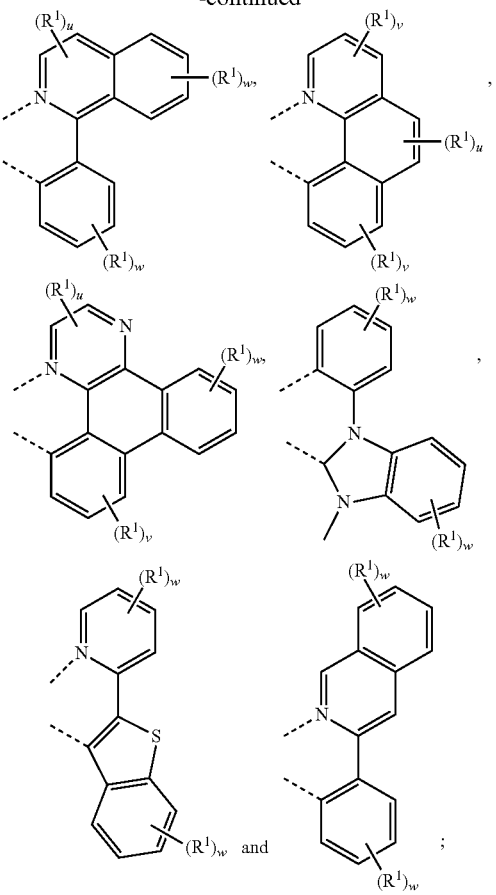

wherein, $R^1$ is selected from one of the group consisting of H, F, Cl, Br, I, D, CN, $NO_2$, $CF_3$, $B(OR^2)_2$, $Si(R^2)_3$, linear alkyl, $R^2$-substituted linear alkyl, alkyl ether group, $R^2$-substituted alkyl ether group, alkyl thioether group, $R^2$-substituted alkyl thioether group, branched alkyl, $R^2$-substituted branched alkyl, cyclic alkyl, and $R^2$-substituted cyclic alkyl;

$R^2$ is selected from one of the group consisting of H, D, aliphatic alkyl, aromatic group, aromatic cyclic group and heteroaromatic group;

the dotted line represents the bond directly connected to the M, u is any integer from 0 to 2, v is any integer from 0 to 3, w is any integer from 0 to 4, and t is any integer from 0 to 5.

7. The metal organic complex according to claim 1, wherein the L is selected from one of

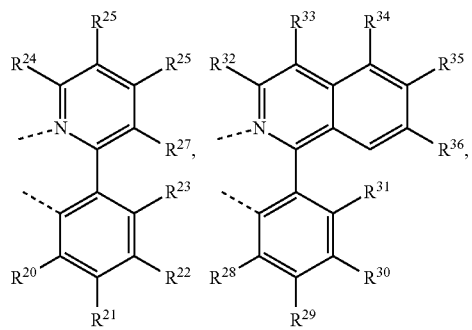

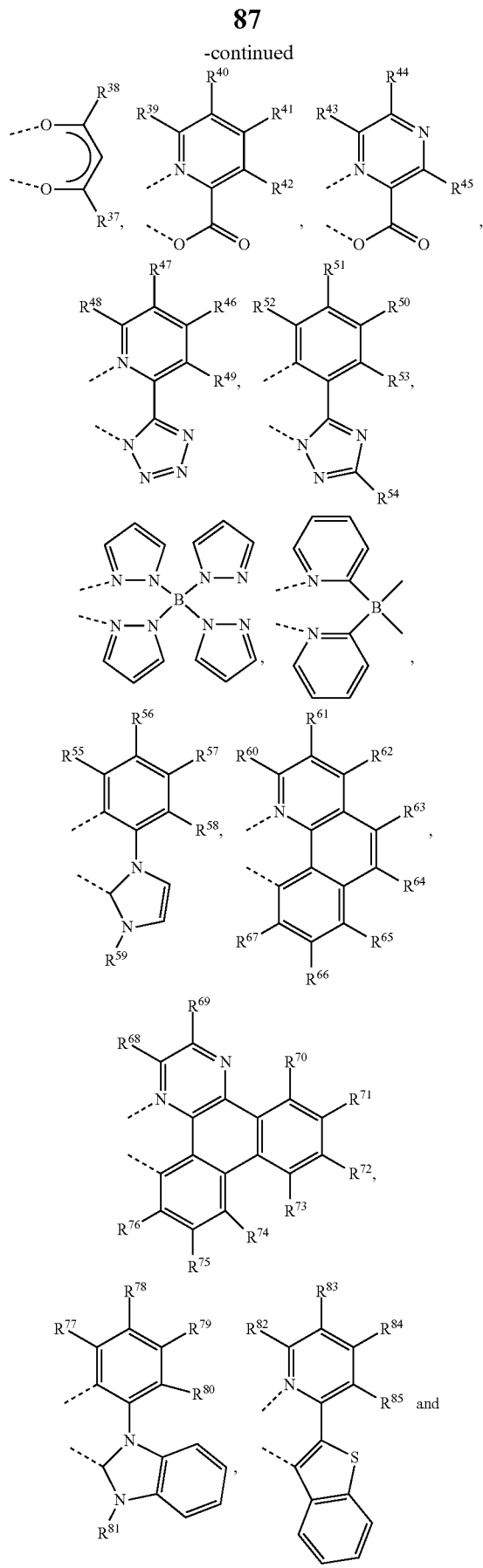

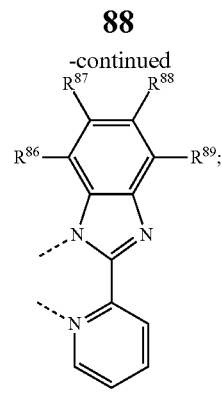

wherein, $R^{20}$ to $R^{89}$ are each selected from one of the group consisting of H, F, Cl, Br, I, D, CN, $NO_2$, $CF_3$, $B(OR^2)_2$, $Si(R^2)_3$, linear alkyl, alkyl ether group, alkyl thioether group containing 1 to 10 carbon atoms, branched alkyl containing 1 to 10 carbon atoms, cyclic alkyl containing 1 to 10 carbon atoms, and aryl containing 6 to 10 carbon atoms; and $R^2$ is selected from one of the group consisting of H, D, aliphatic alkyl, aromatic group, aromatic cyclic group and heteroaromatic group.

8. A formulation comprising the metal organic complex according to claim 1.

9. The formulation according to claim 8, wherein the formulation further comprises organic functional materials selected from at least one of a hole injection material, a hole transport material, a hole blocking material, an electron transport material, an electron injection material, an electron blocking material, a light-emitting material, an organic host material and an organic dye.

10. The formulation according to claim 9, wherein the light-emitting material is selected from one of a singlet emitter, a thermally activated delayed fluorescent material and a triplet emitter.

11. The formulation according to claim 8, wherein the formulation comprises the metal organic complex and an organic functional material, the metal organic complex of the formulation has a mass percentage of 0.01% to 30%.

12. The formulation according to any one of claim 8, wherein the formulation further comprises an organic solvent.

13. The formulation according to claim 12, wherein the formulation further comprises organic functional materials selected from at least one of a hole injection material, a hole transport material, a hole blocking material, an electron transport material, an electron injection material, an electron blocking material, a light-emitting material, an organic host material and an organic dye.

14. An organic electronic device comprising the metal organic complex according to claim 1.

15. The organic electronic device according to claim 14, wherein the organic electronic device is selected from one of the group consisting of an organic light-emitting diode, an organic photovoltaic cell, an organic light-emitting cell, an organic field effect transistor, an organic light-emitting field effect transistor, an organic laser, an organic spintronic device, an organic sensor and an organic plasmon emitting diode.

16. An metal organic complex which has the following general formula:

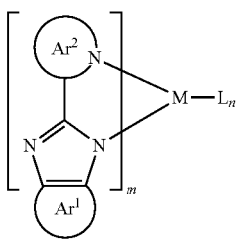

(I)

wherein, Ar² is selected from one of the following groups:

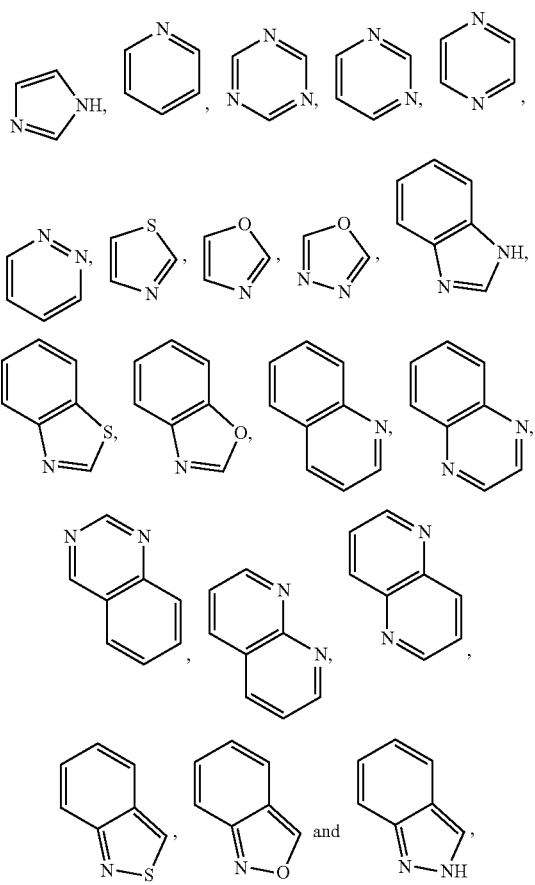

wherein, H in the groups may be further substituted;

Ar¹ is selected from one of the following general formulas:

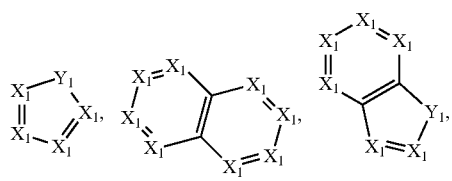

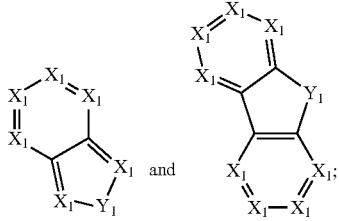

a plurality of $X_1$ are each independently selected from $CR^4$ or N;

$Y_1$ is selected from $CR^4R^5$, $SiR^4R^5$, $NR^4$, $C(=O)$, S or O;

$R^4$ and $R^5$ are each independently selected from at least one of the group consisting of H, D, linear alkyl containing 1 to 20 C atoms, alkoxy containing 1 to 20 C atoms, thioalkoxy containing 1 to 20 C atoms, branched alkyl containing 3 to 20 C atoms, cyclic alkyl containing 3 to 20 C atoms, silyl containing 3 to 20 C atoms, substituted keto containing 1 to 20 C atoms, alkoxycarbonyl containing 2 to 20 C atoms, aryloxycarbonyl containing 7 to 20 C atoms, cyano, carbamoyl, halocarbonyl, formyl, isocyano, isocyanate group, thiocyanate group, isothiocyanate group, hydroxyl, nitryl, $CF_3$ group, Cl, Br, F, crosslinkable group, aromatic cyclic group containing 5 to 40 C atoms, heteroaromatic cyclic group containing 5 to 40 C atoms, aryloxy containing 5 to 40 C atoms and heteroaryloxy containing 5 to 40 C atoms;

wherein, $R^4$ and $R^5$ may form aliphatic or aromatic cyclic groups by bonding with each other, and $R^4$ and $R^5$ may also form aliphatic or aromatic cyclic groups by bonding with themselves, respectively;

M is a transitional metal elemen;

L is selected from one of the group consisting of a monodentate neutral ligand, a monodentate anionic ligand, a bidentate neutral ligand and a bidentate anionic ligand;

m is any integer from 1 to 3; and n is any integer from 0 to 2;

wherein the general formula of the ligand L0 of the metal organic complex is as follows, and the number of C atoms of the substructure Lb of the ligand L0 does not exceed 30:

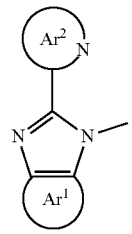

L0

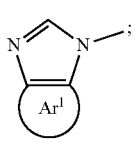

Lb wherein the number of C atoms of the substructure La of the ligand L0 does not exceed 26:
La 5
* * * * *